United States Patent
Arora et al.

(10) Patent No.: US 9,012,784 B2
(45) Date of Patent: Apr. 21, 2015

(54) EXTREMELY STRETCHABLE ELECTRONICS

(71) Applicant: MC10, Inc., Cambridge, MA (US)

(72) Inventors: William J. Arora, Bellevue, WA (US); Roozbeh Ghaffari, Cambridge, MA (US)

(73) Assignee: MC10, Inc., Cambridge, MA (US)

( * ) Notice: Subject to any disclaimer, the term of this patent is extended or adjusted under 35 U.S.C. 154(b) by 0 days.

(21) Appl. No.: 13/767,262

(22) Filed: Feb. 14, 2013

(65) Prior Publication Data

US 2013/0313713 A1 Nov. 28, 2013

Related U.S. Application Data

(63) Continuation of application No. 12/616,922, filed on Nov. 12, 2009, now Pat. No. 8,389,862, and a continuation-in-part of application No. 12/575,008, filed on Oct. 7, 2009.

(60) Provisional application No. 61/113,622, filed on Nov. 12, 2008, provisional application No. 61/103,361, filed on Oct. 7, 2008, provisional application No. 61/113,007, filed on Nov. 10, 2008.

(51) Int. Cl.
*H05K 1/00* (2006.01)
*H05K 1/02* (2006.01)
*H01L 23/00* (2006.01)
*H01L 23/528* (2006.01)
(Continued)

(52) U.S. Cl.
CPC .......... *H01L 23/564* (2013.01); *Y10T 29/4913* (2013.01); *Y10T 29/49204* (2013.01); *Y10T 29/49155* (2013.01); *H05K 1/0283* (2013.01); *A61F 2/958* (2013.01); *H01L 23/528* (2013.01); *H01L 23/52* (2013.01); *H01L 2924/0002* (2013.01)

(58) Field of Classification Search
USPC .................. 174/254; 361/749–751
See application file for complete search history.

(56) References Cited

U.S. PATENT DOCUMENTS

| 3,949,410 A | 4/1976 | Bassous |
| 4,058,418 A | 11/1977 | Lindmayer |

(Continued)

FOREIGN PATENT DOCUMENTS

| CA | 2472809 | 12/2005 |
| CN | 1222758 | 7/1999 |

(Continued)

OTHER PUBLICATIONS

Bachtold et al. (Nov. 9, 2001) "Logic Circuits with Carbon Nanotube Transistors," *Science* 294:1317-1320.

(Continued)

*Primary Examiner* — Jeremy C Norris
(74) *Attorney, Agent, or Firm* — Nixon Peabody LLP

(57) ABSTRACT

In embodiments, the present invention may attach at least two isolated electronic components to an elastomeric substrate, and arrange an electrical interconnection between the components in a boustrophedonic pattern interconnecting the two isolated electronic components with the electrical interconnection. The elastomeric substrate may then be stretched such that the components separate relative to one another, where the electrical interconnection maintains substantially identical electrical performance characteristics during stretching, and where the stretching may extend the separation distance between the electrical components to many times that of the unstretched distance.

24 Claims, 8 Drawing Sheets

(51) Int. Cl.
*H01L 23/52* (2006.01)
*A61F 2/958* (2013.01)

(56) References Cited

U.S. PATENT DOCUMENTS

| | | | |
|---|---|---|---|
| 4,392,451 A | 7/1983 | Mickelsen et al. |
| 4,416,288 A | 11/1983 | Freeman |
| 4,471,003 A | 9/1984 | Cann |
| 4,487,162 A | 12/1984 | Cann |
| 4,663,828 A | 5/1987 | Hanak |
| 4,761,335 A | 8/1988 | Aurichio et al. |
| 4,763,275 A | 8/1988 | Carlin |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,086,785 A | 2/1992 | Gentile et al. |
| 5,118,400 A | 6/1992 | Wollam |
| 5,147,519 A | 9/1992 | Legge |
| 5,178,957 A | 1/1993 | Kolpe et al. |
| 5,204,144 A | 4/1993 | Cann et al. |
| 5,313,094 A | 5/1994 | Beyer et al. |
| 5,316,017 A | 5/1994 | Edwards et al. |
| 5,331,966 A | 7/1994 | Bennett et al. |
| 5,339,180 A | 8/1994 | Katoh |
| 5,403,700 A | 4/1995 | Heller et al. |
| 5,427,096 A | 6/1995 | Bogusiewicz et al. |
| 5,434,751 A | 7/1995 | Cole, Jr. et al. |
| 5,455,178 A | 10/1995 | Fattnger |
| 5,469,845 A | 11/1995 | Delonzor et al. |
| 5,501,893 A | 3/1996 | Laermer et al. |
| 5,525,815 A | 6/1996 | Einset |
| 5,539,935 A | 7/1996 | Rush, III |
| 5,545,291 A | 8/1996 | Smith et al. |
| 5,549,108 A | 8/1996 | Edwards et al. |
| 5,560,974 A | 10/1996 | Langley |
| 5,625,471 A | 4/1997 | Smith |
| 5,648,148 A | 7/1997 | Simpson |
| 5,678,737 A | 10/1997 | White |
| 5,687,737 A | 11/1997 | Branham et al. |
| 5,691,245 A | 11/1997 | Bakhit et al. |
| 5,746,207 A | 5/1998 | McLaughlin et al. |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,783,856 A | 7/1998 | Smith et al. |
| 5,790,151 A | 8/1998 | Mills |
| 5,817,242 A | 10/1998 | Biebuyck et al. |
| 5,824,186 A | 10/1998 | Smith et al. |
| 5,860,974 A | 1/1999 | Abele |
| 5,871,443 A | 2/1999 | Edwards et al. |
| 5,904,545 A | 5/1999 | Smith et al. |
| 5,907,189 A | 5/1999 | Mertol |
| 5,915,180 A | 6/1999 | Hara et al. |
| 5,917,534 A | 6/1999 | Rajeswaran |
| 5,919,155 A * | 7/1999 | Lattin et al. ............ 604/20 |
| 5,928,001 A | 7/1999 | Gillette et al. |
| 5,955,781 A | 9/1999 | Joshi et al. |
| 5,976,683 A | 11/1999 | Liehr et al. |
| 5,978,972 A | 11/1999 | Stewart |
| 5,998,291 A | 12/1999 | Bakhit et al. |
| 6,024,702 A | 2/2000 | Iversen |
| 6,057,212 A | 5/2000 | Chan et al. |
| 6,080,608 A | 6/2000 | Nowak |
| 6,097,984 A | 8/2000 | Douglas |
| 6,121,110 A | 9/2000 | Hong |
| 6,165,391 A | 12/2000 | Vedamuttu |
| 6,165,885 A | 12/2000 | Gaynes et al. |
| 6,171,730 B1 | 1/2001 | Kuroda et al. |
| 6,225,149 B1 | 5/2001 | Gan et al. |
| 6,236,883 B1 | 5/2001 | Ciaccio et al. |
| 6,265,326 B1 | 7/2001 | Ueno |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,284,418 B1 | 9/2001 | Trantolo |
| 6,291,896 B1 | 9/2001 | Smith |
| 6,301,500 B1 | 10/2001 | Van Herk |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,334,960 B1 | 1/2002 | Willson et al. |
| 6,344,616 B1 | 2/2002 | Yokokawa |
| 6,360,615 B1 | 3/2002 | Smela |
| 6,380,729 B1 | 4/2002 | Smith |
| 6,403,397 B1 | 6/2002 | Katz |
| 6,413,790 B1 | 7/2002 | Duthaler et al. |
| 6,414,783 B2 | 7/2002 | Zavracky et al. |
| 6,417,025 B1 | 7/2002 | Gengel |
| 6,420,266 B1 | 7/2002 | Smith et al. |
| 6,433,401 B1 | 8/2002 | Clark et al. |
| 6,451,191 B1 | 9/2002 | Bentsen et al. |
| 6,459,418 B1 | 10/2002 | Comiskey et al. |
| 6,468,638 B2 | 10/2002 | Jacobsen et al. |
| 6,479,395 B1 | 11/2002 | Smith et al. |
| 6,504,105 B1 | 1/2003 | Acocella et al. |
| 6,517,995 B1 | 2/2003 | Jacobsen et al. |
| 6,527,964 B1 | 3/2003 | Smith et al. |
| 6,555,408 B1 | 4/2003 | Jacobsen et al. |
| 6,559,905 B1 | 5/2003 | Akiyama |
| 6,566,744 B2 | 5/2003 | Gengel |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,613,979 B1 | 9/2003 | Miller et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |
| 6,666,821 B2 | 12/2003 | Keimel |
| 6,667,548 B2 | 12/2003 | O'Connor et al. |
| 6,683,663 B1 | 1/2004 | Hadley et al. |
| 6,693,384 B1 | 2/2004 | Vicentini et al. |
| 6,706,402 B2 | 3/2004 | Rueckes et al. |
| 6,720,469 B1 | 4/2004 | Curtis et al. |
| 6,723,576 B2 | 4/2004 | Nozawa et al. |
| 6,730,990 B2 | 5/2004 | Kondo et al. |
| 6,731,353 B1 | 5/2004 | Credelle et al. |
| 6,743,982 B2 | 6/2004 | Biegelsen et al. |
| 6,762,510 B2 | 7/2004 | Fock et al. |
| 6,780,696 B1 | 8/2004 | Schatz |
| 6,784,450 B2 | 8/2004 | Pan et al. |
| 6,787,052 B1 | 9/2004 | Vaganov |
| 6,814,898 B1 | 11/2004 | Deeman et al. |
| 6,816,380 B2 | 11/2004 | Credelle et al. |
| 6,826,509 B2 | 11/2004 | Crisco, III et al. |
| 6,836,744 B1 | 12/2004 | Asphahani et al. |
| 6,844,673 B1 | 1/2005 | Bernkopf |
| 6,848,162 B2 | 2/2005 | Arneson et al. |
| 6,850,312 B2 | 2/2005 | Jacobsen et al. |
| 6,856,830 B2 | 2/2005 | He |
| 6,863,219 B1 | 3/2005 | Jacobsen et al. |
| 6,864,435 B2 | 3/2005 | Hermanns et al. |
| 6,864,570 B2 | 3/2005 | Smith |
| 6,872,645 B2 | 3/2005 | Duan et al. |
| 6,878,871 B2 | 4/2005 | Scher et al. |
| 6,881,979 B2 | 4/2005 | Starikov et al. |
| 6,885,030 B2 | 4/2005 | Onozuka et al. |
| 6,887,450 B2 | 5/2005 | Chen et al. |
| 6,887,792 B2 | 5/2005 | Perlov et al. |
| 6,900,094 B2 | 5/2005 | Hammond et al. |
| 6,917,061 B2 | 7/2005 | Pan et al. |
| 6,936,181 B2 | 8/2005 | Bulthaup et al. |
| 6,949,199 B1 | 9/2005 | Gauzner et al. |
| 6,949,206 B2 | 9/2005 | Whiteford |
| 6,950,220 B2 | 9/2005 | Abramson et al. |

(56) References Cited

U.S. PATENT DOCUMENTS

| | | |
|---|---|---|
| 6,967,362 B2 | 11/2005 | Nam et al. |
| 6,984,934 B2 | 1/2006 | Moller et al. |
| 6,989,285 B2 | 1/2006 | Ball |
| 7,029,951 B2 | 4/2006 | Chen et al. |
| 7,033,961 B1 | 4/2006 | Smart et al. |
| 7,054,784 B2 | 5/2006 | Flentov et al. |
| 7,067,903 B2 | 6/2006 | Tachibana et al. |
| 7,081,642 B2 | 7/2006 | Onozuka et al. |
| 7,116,318 B2 | 10/2006 | Amundson et al. |
| 7,132,313 B2 | 11/2006 | O'Connor et al. |
| 7,148,512 B2 | 12/2006 | Leu et al. |
| 7,158,277 B2 | 1/2007 | Berggren et al. |
| 7,169,546 B2 | 1/2007 | Suzuki et al. |
| 7,169,669 B2 | 1/2007 | Blakers et al. |
| 7,170,164 B2 | 1/2007 | Chen et al. |
| 7,186,624 B2 | 3/2007 | Welser et al. |
| 7,190,051 B2 | 3/2007 | Mech et al. |
| 7,195,733 B2 | 3/2007 | Rogers et al. |
| 7,223,609 B2 | 5/2007 | Anvar et al. |
| 7,223,632 B2 | 5/2007 | Onozuka et al. |
| 7,252,664 B2 | 8/2007 | Nasab et al. |
| 7,253,442 B2 | 8/2007 | Huang et al. |
| 7,255,919 B2 | 8/2007 | Sakata et al. |
| 7,265,298 B2 | 9/2007 | Maghribi et al. |
| 7,291,146 B2 | 11/2007 | Steinke et al. |
| 7,291,540 B2 | 11/2007 | Mech et al. |
| 7,293,353 B2 | 11/2007 | Matsuda |
| 7,337,012 B2 | 2/2008 | Maghribi et al. |
| 7,374,968 B2 | 5/2008 | Kornilovich et al. |
| 7,425,523 B2 | 9/2008 | Ikemizu et al. |
| 7,487,587 B2 | 2/2009 | Vanfleteren et al. |
| 7,491,892 B2 | 2/2009 | Wagner et al. |
| 7,509,835 B2 | 3/2009 | Beck |
| 7,509,869 B2 | 3/2009 | Liu et al. |
| 7,521,292 B2 | 4/2009 | Rogers et al. |
| 7,526,389 B2 | 4/2009 | Greenwald et al. |
| 7,557,367 B2 | 7/2009 | Rogers et al. |
| 7,593,086 B2 | 9/2009 | Jeong et al. |
| 7,616,781 B2 | 11/2009 | Schofield et al. |
| 7,622,367 B1 | 11/2009 | Nuzzo et al. |
| 7,629,691 B2 | 12/2009 | Roush et al. |
| 7,633,761 B2 | 12/2009 | Kim |
| 7,635,755 B2 | 12/2009 | Kaplan et al. |
| 7,674,882 B2 | 3/2010 | Kaplan et al. |
| 7,693,668 B2 | 4/2010 | Vock et al. |
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,199 B2 | 6/2010 | Fernandes et al. |
| 7,727,575 B2 | 6/2010 | Kaplan et al. |
| 7,742,795 B2 | 6/2010 | Stone et al. |
| 7,759,167 B2 | 7/2010 | Vanfleteren et al. |
| 7,764,990 B2 | 7/2010 | Martikka et al. |
| 7,792,329 B2 | 9/2010 | Schofield et al. |
| 7,799,699 B2 | 9/2010 | Nuzzo et al. |
| 7,842,780 B2 | 11/2010 | Kaplan et al. |
| 7,857,781 B2 | 12/2010 | Noda et al. |
| 7,871,661 B2 | 1/2011 | Maghribi et al. |
| 7,884,540 B2 | 2/2011 | Sung et al. |
| 7,932,123 B2 | 4/2011 | Rogers et al. |
| 7,935,056 B2 | 5/2011 | Zdeblick |
| 7,943,491 B2 | 5/2011 | Nuzzo et al. |
| 7,960,246 B2 | 6/2011 | Flamand et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,107,248 B2 | 1/2012 | Shin et al. |
| 8,178,209 B2 | 5/2012 | Qi et al. |
| 8,198,621 B2 | 6/2012 | Rogers et al. |
| 8,207,473 B2 | 6/2012 | Axisa et al. |
| 8,217,381 B2 | 7/2012 | Rogers et al. |
| 8,252,191 B2 | 8/2012 | Qi et al. |
| 8,470,701 B2 | 6/2013 | Rogers et al. |
| 8,552,299 B2 | 10/2013 | Rogers et al. |
| 8,562,095 B2 | 10/2013 | Alleyne et al. |
| 2001/0003043 A1 | 6/2001 | Metspalu et al. |
| 2001/0012918 A1 | 8/2001 | Swanson |
| 2001/0021867 A1 | 9/2001 | Kordis |
| 2002/0021445 A1 | 2/2002 | Bozhevolnyi et al. |
| 2002/0082515 A1 | 6/2002 | Campbell et al. |
| 2002/0094701 A1 | 7/2002 | Biegelsen et al. |
| 2002/0110766 A1 | 8/2002 | Tsai et al. |
| 2002/0151934 A1 | 10/2002 | Levine |
| 2003/0006527 A1 | 1/2003 | Rabolt et al. |
| 2003/0017848 A1 | 1/2003 | Engstrom et al. |
| 2003/0032892 A1 | 2/2003 | Erlach et al. |
| 2003/0082889 A1 | 5/2003 | Maruyama et al. |
| 2003/0087476 A1 | 5/2003 | Oohata et al. |
| 2003/0138704 A1 | 7/2003 | Mei et al. |
| 2003/0149456 A1 | 8/2003 | Rottenberg et al. |
| 2003/0171691 A1 | 9/2003 | Casscells et al. |
| 2003/0178316 A1 | 9/2003 | Jacobs et al. |
| 2003/0222282 A1 | 12/2003 | Fjelstad et al. |
| 2003/0227116 A1 | 12/2003 | Halik et al. |
| 2004/0005723 A1 | 1/2004 | Empedocles et al. |
| 2004/0006264 A1 | 1/2004 | Mojarradi et al. |
| 2004/0026684 A1 | 2/2004 | Empedocles et al. |
| 2004/0061543 A1 | 4/2004 | Nam et al. |
| 2004/0079464 A1 | 4/2004 | Kumakura |
| 2004/0081384 A1 | 4/2004 | Datesman et al. |
| 2004/0092806 A1 | 5/2004 | Sagon |
| 2004/0095658 A1 | 5/2004 | Buretea et al. |
| 2004/0112964 A1 | 6/2004 | Empedocles et al. |
| 2004/0136866 A1 | 7/2004 | Pontis et al. |
| 2004/0146560 A1 | 7/2004 | Whiteford et al. |
| 2004/0155290 A1 | 8/2004 | Mech et al. |
| 2004/0171969 A1 | 9/2004 | Socci |
| 2004/0178390 A1 | 9/2004 | Whiteford |
| 2004/0192062 A1 | 9/2004 | Mikelson |
| 2004/0192082 A1 | 9/2004 | Wagner et al. |
| 2004/0200734 A1 | 10/2004 | Co |
| 2004/0206448 A1 | 10/2004 | Dubrow |
| 2004/0211458 A1 | 10/2004 | Gui et al. |
| 2004/0211459 A1 | 10/2004 | Suenaga et al. |
| 2004/0229830 A1 | 11/2004 | Tachibana et al. |
| 2004/0243204 A1 | 12/2004 | Maghribi et al. |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0021103 A1 | 1/2005 | DiLorenzo |
| 2005/0038498 A1 | 2/2005 | Dubrow et al. |
| 2005/0082526 A1 | 4/2005 | Bedell et al. |
| 2005/0107716 A1 | 5/2005 | Eaton et al. |
| 2005/0113744 A1 | 5/2005 | Donoghue et al. |
| 2005/0124712 A1 | 6/2005 | Anderson et al. |
| 2005/0133954 A1 | 6/2005 | Homola |
| 2005/0171524 A1 | 8/2005 | Stern et al. |
| 2005/0177335 A1 | 8/2005 | Crisco |
| 2005/0203366 A1 | 9/2005 | Donoghue et al. |
| 2005/0214962 A1 | 9/2005 | Daniels et al. |
| 2005/0227389 A1 | 10/2005 | Bhattacharya et al. |
| 2005/0233546 A1 | 10/2005 | Oohata et al. |
| 2005/0238967 A1 | 10/2005 | Rogers et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0038182 A1 | 2/2006 | Rogers et al. |
| 2006/0049485 A1 | 3/2006 | Pan et al. |
| 2006/0056161 A1 | 3/2006 | Shin et al. |
| 2006/0076561 A1 | 4/2006 | Hicki et al. |
| 2006/0084012 A1 | 4/2006 | Nuzzo et al. |
| 2006/0084394 A1 | 4/2006 | Engstrom et al. |
| 2006/0085976 A1 | 4/2006 | Eldridge et al. |
| 2006/0102525 A1 | 5/2006 | Volkel et al. |
| 2006/0106321 A1 | 5/2006 | Lewinsky et al. |
| 2006/0119853 A1 | 6/2006 | Baumberg et al. |
| 2006/0127817 A1 | 6/2006 | Ramanujan et al. |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0159837 A1 | 7/2006 | Kaplan et al. |
| 2006/0169989 A1 | 8/2006 | Bhattacharya et al. |
| 2006/0173364 A1 | 8/2006 | Clancy et al. |

(56) References Cited

U.S. PATENT DOCUMENTS

| | | |
|---|---|---|
| 2006/0177479 A1 | 8/2006 | Giachelli et al. |
| 2006/0178655 A1 | 8/2006 | Santini et al. |
| 2006/0231288 A1 | 10/2006 | Vanfleteren et al. |
| 2006/0244105 A1 | 11/2006 | Forbes et al. |
| 2006/0255341 A1 | 11/2006 | Pinnington et al. |
| 2006/0273279 A1 | 12/2006 | Kaplan et al. |
| 2006/0279191 A1 | 12/2006 | Geohegan et al. |
| 2006/0286488 A1 | 12/2006 | Rogers et al. |
| 2006/0286785 A1 | 12/2006 | Rogers et al. |
| 2007/0009968 A1 | 1/2007 | Cunningham et al. |
| 2007/0027514 A1 | 2/2007 | Gerber |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0123756 A1 | 5/2007 | Kitajima et al. |
| 2007/0187862 A1 | 8/2007 | Kaplan et al. |
| 2007/0212730 A1 | 9/2007 | Vepari et al. |
| 2007/0213616 A1 | 9/2007 | Anderson et al. |
| 2007/0227586 A1 | 10/2007 | Zapalac |
| 2007/0228502 A1 | 10/2007 | Minamio et al. |
| 2007/0233208 A1 | 10/2007 | Kurtz et al. |
| 2007/0257821 A1 | 11/2007 | Son et al. |
| 2008/0000871 A1 | 1/2008 | Suh et al. |
| 2008/0008626 A1 | 1/2008 | Lin et al. |
| 2008/0038236 A1 | 2/2008 | Gimble et al. |
| 2008/0041617 A1 | 2/2008 | Chen et al. |
| 2008/0046080 A1 | 2/2008 | Bulcke et al. |
| 2008/0054875 A1 | 3/2008 | Saito |
| 2008/0055581 A1 | 3/2008 | Rogers et al. |
| 2008/0077225 A1 | 3/2008 | Carlin et al. |
| 2008/0085272 A1 | 4/2008 | Kaplan et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0108942 A1 | 5/2008 | Brister et al. |
| 2008/0140152 A1 | 6/2008 | Imran |
| 2008/0152281 A1 | 6/2008 | Lundquist et al. |
| 2008/0157234 A1 | 7/2008 | Hong |
| 2008/0157235 A1 | 7/2008 | Rogers et al. |
| 2008/0183076 A1 | 7/2008 | Witte et al. |
| 2008/0188912 A1 | 8/2008 | Stone et al. |
| 2008/0203268 A1 | 8/2008 | Hobbs et al. |
| 2008/0203431 A1 | 8/2008 | Garcia et al. |
| 2008/0208268 A1 | 8/2008 | Bartic |
| 2008/0212102 A1 | 9/2008 | Nuzzo et al. |
| 2008/0239755 A1 | 10/2008 | Parker et al. |
| 2008/0257586 A1 | 10/2008 | Chen et al. |
| 2008/0278336 A1 | 11/2008 | Ortega et al. |
| 2008/0280360 A1 | 11/2008 | Kaplan et al. |
| 2008/0287167 A1 | 11/2008 | Caine |
| 2008/0287747 A1 | 11/2008 | Mestrovic et al. |
| 2008/0288037 A1 | 11/2008 | Neysmith et al. |
| 2008/0293919 A1 | 11/2008 | Kaplan et al. |
| 2008/0313552 A1 | 12/2008 | Buehler et al. |
| 2009/0004737 A1 | 1/2009 | Borenstein et al. |
| 2009/0012533 A1 | 1/2009 | Barbagli et al. |
| 2009/0015560 A1 | 1/2009 | Robinson et al. |
| 2009/0028910 A1 | 1/2009 | Desimone et al. |
| 2009/0054742 A1 | 2/2009 | Kaminska et al. |
| 2009/0107704 A1 | 4/2009 | Vanfleteren et al. |
| 2009/0149930 A1 | 6/2009 | Schenck |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208058 A1 | 8/2009 | Schofield et al. |
| 2009/0208555 A1 | 8/2009 | Kuttler et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0247909 A1 | 10/2009 | Mukumoto |
| 2009/0289246 A1 | 11/2009 | Schneider et al. |
| 2009/0293664 A1 | 12/2009 | Aabloo et al. |
| 2009/0294803 A1 | 12/2009 | Nuzzo et al. |
| 2009/0317639 A1 | 12/2009 | Axisa et al. |
| 2010/0002402 A1 | 1/2010 | Rogers et al. |
| 2010/0028451 A1 | 2/2010 | Kaplan et al. |
| 2010/0045797 A1 | 2/2010 | Schofield et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0096763 A1 | 4/2010 | Kaplan et al. |
| 2010/0120116 A1 | 5/2010 | Kaplan et al. |
| 2010/0121420 A1 | 5/2010 | Fiset et al. |
| 2010/0141407 A1 | 6/2010 | Heubel et al. |
| 2010/0152619 A1 | 6/2010 | Kalpaxis et al. |
| 2010/0176705 A1 | 7/2010 | Van Herpen et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0252840 A1 | 10/2010 | Ibbetson et al. |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0317132 A1 | 12/2010 | Rogers et al. |
| 2010/0324455 A1 | 12/2010 | Rangel et al. |
| 2011/0054583 A1 | 3/2011 | Litt et al. |
| 2011/0068672 A1 | 3/2011 | Hasnain |
| 2011/0071439 A1 | 3/2011 | Bach-y-Rita et al. |
| 2011/0129158 A1 | 6/2011 | Sato |
| 2011/0147715 A1 | 6/2011 | Rogers et al. |
| 2011/0168403 A1 | 7/2011 | Patel |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0266561 A1 | 11/2011 | Rogers et al. |
| 2011/0277813 A1 | 11/2011 | Rogers et al. |
| 2011/0316120 A1 | 12/2011 | Rogers et al. |
| 2012/0051005 A1 | 3/2012 | Vanfleteren et al. |
| 2012/0052268 A1 | 3/2012 | Axisa et al. |
| 2012/0065937 A1 | 3/2012 | de Graff |
| 2012/0092178 A1 | 4/2012 | Callsen et al. |
| 2012/0105528 A1 | 5/2012 | Alleyne |
| 2012/0157804 A1 | 6/2012 | Rogers et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0158101 A1 | 6/2012 | Stone et al. |
| 2012/0165759 A1 | 6/2012 | Rogers et al. |
| 2012/0261551 A1 | 10/2012 | Rogers |

FOREIGN PATENT DOCUMENTS

| | | |
|---|---|---|
| CN | 1454045 | 11/2003 |
| CN | 101772348 A | 7/2010 |
| DE | 4241045 C1 | 5/1994 |
| DE | 19748173 | 5/1999 |
| EP | 0929097 | 7/1999 |
| EP | 1357773 | 10/2003 |
| EP | 1 467 224 | 10/2004 |
| EP | 1 477 230 | 11/2004 |
| EP | 1 498 456 | 1/2005 |
| EP | 1 511 096 | 3/2005 |
| EP | 1 558 444 | 8/2005 |
| EP | 1 613 796 | 1/2006 |
| EP | 1746869 | 1/2007 |
| EP | 1 773 240 | 4/2007 |
| EP | 1 915 436 | 4/2008 |
| EP | 1 726 329 | 8/2009 |
| EP | 2 086 749 | 8/2009 |
| EP | 2 101 975 | 9/2009 |
| EP | 2 107 964 | 10/2009 |

(56) References Cited

FOREIGN PATENT DOCUMENTS

| | | |
|---|---|---|
| EP | 2 109 634 | 10/2009 |
| EP | 2 129 772 | 12/2009 |
| EP | 2 206 017 | 7/2010 |
| EP | 2 211 876 | 8/2010 |
| EP | 2 249 886 | 11/2010 |
| JP | 01-223064 | 9/1989 |
| JP | 2005-126595 | 5/1993 |
| JP | 2006118441 | 4/1994 |
| JP | 2006-163365 | 6/1994 |
| JP | 2011-026344 | 1/1999 |
| JP | 2001-332383 | 11/2001 |
| JP | 2001-523631 | 11/2001 |
| JP | 2002092984 | 3/2002 |
| JP | 2003182475 | 7/2003 |
| JP | 2003-289136 | 10/2003 |
| JP | 2003-297974 | 10/2003 |
| JP | 2004-506254 | 2/2004 |
| JP | 2005-085830 | 3/2005 |
| JP | 2005059800 | 3/2005 |
| JP | 2006-504450 | 2/2006 |
| JP | 2006044383 | 2/2006 |
| JP | 2006-186294 | 7/2006 |
| JP | 2007-515391 | 6/2007 |
| JP | 2007-266380 | 10/2007 |
| JP | 2008-502739 | 1/2008 |
| JP | 2008-531137 | 8/2008 |
| JP | 2010-508852 | 3/2010 |
| JP | 2010-509593 | 3/2010 |
| JP | 2010-509644 | 3/2010 |
| JP | 2010-509645 | 3/2010 |
| JP | 2010-522583 | 7/2010 |
| JP | 2010-529230 | 8/2010 |
| KR | 10-2007-0100617 | 10/2007 |
| KR | 10-2008-0069553 | 7/2008 |
| TW | 367570 | 8/1999 |
| TW | 494257 | 7/2002 |
| TW | 200836353 | 9/2008 |
| WO | WO 96/21245 | 7/1996 |
| WO | WO 98/49936 | 11/1998 |
| WO | WO 99/45860 | 9/1999 |
| WO | WO 00/46854 | 8/2000 |
| WO | WO 00/49421 | 8/2000 |
| WO | WO 00/49658 | 8/2000 |
| WO | WO 00/55915 | 9/2000 |
| WO | WO 00/55916 | 9/2000 |
| WO | WO 01/31082 | 5/2001 |
| WO | WO 01/33621 | 5/2001 |
| WO | WO 01/66833 | 9/2001 |
| WO | WO 01/98838 | 12/2001 |
| WO | WO 02/27701 | 4/2002 |
| WO | WO 02/43032 | 5/2002 |
| WO | WO 02/45160 | 6/2002 |
| WO | WO 02/071137 | 9/2002 |
| WO | WO 02/073699 | 9/2002 |
| WO | WO 02/092778 | 11/2002 |
| WO | WO 02/097708 | 12/2002 |
| WO | WO 02/097724 | 12/2002 |
| WO | WO 03/021679 | 3/2003 |
| WO | WO 03/030194 | 4/2003 |
| WO | WO 03/032240 | 4/2003 |
| WO | WO 03/049201 | 6/2003 |
| WO | WO 03/060986 | 7/2003 |
| WO | WO 03/063211 | 7/2003 |
| WO | WO 03/085700 | 10/2003 |
| WO | WO 03/085701 | 10/2003 |
| WO | WO 03/092073 | 11/2003 |
| WO | WO 04/000915 | 12/2003 |
| WO | WO 04/001103 | 12/2003 |
| WO | WO 2004/003535 | 1/2004 |
| WO | WO 2004/016485 | 2/2004 |
| WO | WO 2004/022637 | 3/2004 |
| WO | WO 2004/022714 | 3/2004 |
| WO | WO 2004/023527 | 3/2004 |
| WO | WO 2004/024407 | 3/2004 |
| WO | WO 2004/027822 | 4/2004 |
| WO | WO 2004/032190 | 4/2004 |
| WO | WO 2004/032191 | 4/2004 |
| WO | WO 2004/032193 | 4/2004 |
| WO | WO 2004/034025 | 4/2004 |
| WO | WO 2004/062697 | 7/2004 |
| WO | WO 2004-086530 | 7/2004 |
| WO | WO 2004/086289 | 10/2004 |
| WO | WO 2004/094303 | 11/2004 |
| WO | WO 2004/099536 | 11/2004 |
| WO | WO 2004/100252 | 11/2004 |
| WO | WO 2004/099068 | 12/2004 |
| WO | WO 2004/105456 | 12/2004 |
| WO | WO 2004/107973 | 12/2004 |
| WO | WO 2005/000483 | 1/2005 |
| WO | WO 2005/005679 | 1/2005 |
| WO | WO 2005/012606 | 2/2005 |
| WO | WO 2005/015480 | 2/2005 |
| WO | WO 2005/017962 | 2/2005 |
| WO | WO 2005/022120 | 3/2005 |
| WO | WO-2005/029578 | 3/2005 |
| WO | WO 2005/029578 | 3/2005 |
| WO | WO 2005/033786 | 4/2005 |
| WO | WO 2005/033787 | 4/2005 |
| WO | WO 2005/033789 | 4/2005 |
| WO | WO 2005/054119 | 6/2005 |
| WO | WO 2005/099310 | 10/2005 |
| WO | WO 2005/104756 | 11/2005 |
| WO | WO 2005/106934 | 11/2005 |
| WO | WO 2005/122285 | 12/2005 |
| WO | WO 2005/123114 | 12/2005 |
| WO | WO 2006/028996 | 3/2006 |
| WO | WO 2006/042287 | 4/2006 |
| WO | WO 2006/069323 | 6/2006 |
| WO | WO 2006/076711 | 7/2006 |
| WO | WO 2006/104069 | 10/2006 |
| WO | WO 2006/130721 | 12/2006 |
| WO | WO 2007/000037 | 1/2007 |
| WO | WO-2007/000037 | 1/2007 |
| WO | WO 2007/016524 | 2/2007 |
| WO | WO 2007/028003 | 3/2007 |
| WO | WO 2007/056183 | 5/2007 |
| WO | WO 2007/116344 | 10/2007 |
| WO | WO 2007/126412 | 11/2007 |
| WO | WO 2008/030666 | 3/2008 |
| WO | WO 2008/030960 | 3/2008 |
| WO | WO 2008/036837 | 3/2008 |
| WO | WO 2008/055054 | 5/2008 |
| WO | WO 2008/085904 | 7/2008 |
| WO | WO 2008/103464 | 8/2008 |
| WO | WO 2008/106485 | 9/2008 |
| WO | WO 2008/108838 | 9/2008 |
| WO | WO 2008/118133 | 10/2008 |
| WO | WO 2008/118211 | 10/2008 |
| WO | WO 2008/127401 | 10/2008 |
| WO | WO 2008/127402 | 10/2008 |
| WO | WO 2008/127403 | 10/2008 |
| WO | WO 2008/127404 | 10/2008 |
| WO | WO 2008/127405 | 10/2008 |
| WO | WO 2008/140562 | 11/2008 |
| WO | WO 2008/143635 | 11/2008 |
| WO | WO 2008/150861 | 12/2008 |
| WO | WO 2008/157298 | 12/2008 |
| WO | WO 2009/011709 | 1/2009 |
| WO | WO 2009/023615 | 2/2009 |
| WO | WO 2009/061823 | 5/2009 |
| WO | WO 2009/075625 | 6/2009 |
| WO | WO 2009/076088 | 6/2009 |
| WO | WO 2009/090398 | 7/2009 |
| WO | WO 2009/100280 | 8/2009 |
| WO | WO 2009/111641 | 9/2009 |
| WO | WO 2009/114115 | 9/2009 |
| WO | WO 2009/114689 | 9/2009 |
| WO | WO 2009/118678 | 10/2009 |
| WO | WO 2009/126689 | 10/2009 |
| WO | WO 2009/140588 | 11/2009 |
| WO | WO 2009/155397 | 12/2009 |
| WO | WO 2010/005707 | 1/2010 |
| WO | WO 2010/036807 | 4/2010 |
| WO | WO 2010/036992 | 4/2010 |

(56) References Cited

FOREIGN PATENT DOCUMENTS

| | | |
|---|---|---|
| WO | WO 2010/040528 | 4/2010 |
| WO | WO 2010/042798 | 4/2010 |
| WO | WO 2010/049881 | 5/2010 |
| WO | WO 2010/057142 | 5/2010 |
| WO | WO 2010/065957 | 6/2010 |
| WO | WO 2010/081989 | 7/2010 |
| WO | WO 2010/126640 | 11/2010 |
| WO | WO 2010/132552 | 11/2010 |
| WO | WO 2010/141133 | 12/2010 |
| WO | WO 2011/002931 | 1/2011 |
| WO | WO 2011/005381 | 1/2011 |
| WO | WO 2011/006133 | 1/2011 |
| WO | WO 2011/008842 | 1/2011 |
| WO | WO 2011/011347 | 1/2011 |
| WO | WO 2011/026101 | 3/2011 |
| WO | WO 2011/038401 | 3/2011 |
| WO | WO 2011/041395 | 4/2011 |
| WO | WO 2011/046652 | 4/2011 |
| WO | WO 2011/084450 | 7/2011 |
| WO | WO 2011/112931 | 9/2011 |
| WO | WO 2011/115643 | 9/2011 |
| WO | WO 2012/097163 | 7/2012 |
| WO | WO 2012/158709 | 11/2012 |
| WO | WO 2012/167096 | 12/2012 |
| WO | WO 2013/010113 | 1/2013 |
| WO | WO 2013/149181 | 10/2013 |

OTHER PUBLICATIONS

Bowden et al. (1997) "Self Assembly of Mesoscale Objects into Ordered Two-Dimensional Arrays," Science 276:233-235.
Decision of Refusal corresponding to Japanese Patent Application No. P2007-515549, Issued Sep. 4, 2012.
Decision of Rejection corresponding to Korean Patent Application No. 10-2007-7000216, Issued Sep. 19, 2012—includes English translation.
European Extended Search Report dated Feb. 13, 2014, in Application No. 11766768.3.
Extended European Search Report, Corresponding to European Application No. 10842663.6 dated Jan. 9, 2014.
First Examination Report, Corresponding to India Patent Application No. 7581DELNP, dated Nov. 8, 2013.
International Preliminary Report on Patentability and Written Opinion Corresponding to International Application No. PCT/US2012/053701, mailed Mar. 4, 2014.
Notice of Allowance corresponding to Korean Patent Application No. 10-20102-7010094, dated Feb. 25, 2013—includes English translation.
Notice of Final Rejection for Japanese Patent Application No. 2007-515549, dated Sep. 19, 2012.
Notice of Preliminary Rejection corresponding to Korean Patent Application No. 10-2007-7000216, dated Feb. 21, 2013—includes English translation.
Notice of Preliminary Rejection corresponding to Korean Patent Application No. 10-2012-7030789, dated Feb. 25, 2013—includes English translation.
Notice of Reasons of Rejection corresponding to Japanese Patent Application No. 2009-527564, mailed Jan. 29. 2013.
Notification of Grant of Patent Right and Notice of Registration corresponding to Chinese Patent App. No. 200780041127.6 issued Dec. 26, 2012.
Office Action, Corresponding to Japanese Patent Application No. 2011-536465, dated Jan. 21, 2014.
Office Action, Corresponding to Japanese Patent Application No. JP2011545508, dated Feb. 12, 2014.
Office Action, Corresponding to U.S. Appl. No. 12/616,922, mailed Apr. 9, 2012.
Office Actions and Responses, Corresponding to U.S. Appl. No. 11/981,380, Mailed Beginning Sep. 23, 2010.
Final Office Action mailed Nov. 21, 2012 corresponding to U.S. Appl. No. 12/921,808.
International Search Report and Written Opinion, Corresponding to Inernational Application No. PCT/US12/46930 mailed Dec. 10, 2012.
Office Action, Corresponding to U.S. Appl. No. 12/398,811 mailed Nov. 26, 2012.
Response to Examination Report for Malaysian Divisional Appl. No. PI 20094997 dated Nov. 16, 2012.
Response to Substantive Examination Report for Malaysian Appl. No. PI 20090622 mailed Nov. 23, 2012.
Second Substantive Office Action corrresponding to Chinese Patent Application No. 20100519400.5 issued on Oct. 30, 2012.
U.S. Office Action for U.S. Appl. No. 12/405,475 mailed Jun. 8, 2011.
US Office Action for U.S. Appl. No. 11/851,182 mailed Apr. 1, 2010.
US Office Action for U.S. Appl. No. 11/851,182 mailed Oct. 29, 2010.
US Office Action for U.S. Appl. No. 11/851,182 mailed Jun. 7, 2011.
US Office Action for U.S. Appl. No. 12/636,071 mailed Jan. 3, 2013.
Abbaschian et al. (Dec. 2005) "High Pressure-High Temperature Growth of Diamond Crystals Using Split Sphere Apparatus," Diamond Relat. Mater. 14(11-12): 1916-1919.
Adachi et al (1982) "Chemical Etching of InGaAsP/inP DH Wafer," J. Electrochem. Soc. 129:1053-1062.
Adachi et al. (1983) "Chemical Etching Characteristics of (001) GaAs," J. Electrochem. Soc. 130:2427-2435.
Adrega et al. (2010) "Stretchable Gold Conductors Embedded in PDMS and Patterned by Photolithography: Fabrication and Electromechanical Characterization," J. Micromech. Microeng. 20:055025.
Ago et al. (2005) "Aligned Growth of Isolated Single-Walled Carbon Nanotubes Programmed vby Atomic Arrangement of Substrate Surface," Chem. Phys. Lett. 408:433-438.
Ago et al. (2006) "Synthesis of Horizontally-Aligned Single-Walled Carbon Nanotubes with Controllable Density on Sapphire Surface and Polarized Raman Spectroscopy," Chem. Phys. Lett. 421:399-403.
Ahmed et al. (Web Release Oct. 11,2005) "Extending the 3w-Method to the MHz Range for Thermal Conductivity Measurements of Diamond Thin Films," Diamond Relat. Mater. 15(2-3):389393.
Ahn et al. (2007) "Bendable Integrated Circuits on Plastic Substrates by Use of Printed Ribbons of Single-Crystalline Silicon," Appl. Phys. Lett. 90:213501.
Ahn et al. (Dec. 15, 2006) "Heterogeneous Three-Dimensional Electronics by Use of Printed Semiconductor Nanomaterials," Science 314:1754-1757.
Ahn et al. (Jun. 2006) "High-Speed Mechanically Flexible Single-Crystal Silicon Thin-Film Transistors on Plastic Substrates," IEEE Electron Dev. Lett. 27(6):460-462.
Al-Sarawi et al. (Feb. 1998) "A Review of 3-D Packaging Technology," IEEE Trans. Compo Packag. Manufac. Technol. B 21(1):2-14.
Al-Halhouli et al. (2008) "Nanoindentation Testing of SU-8 Photoresist Mechanical Properties," Microelectronic Eng. 85:942-944.
Aliot, E. M. et al. (2009) "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)," Europace 11:771-817.
Alivisatos et al. (1996) "Semiconductor Clusters, Nanocrystals, and Quantum Dots," Science 271:933-937.
Alivisatos et al. (1998) "From Molecules to Materials: Current Trends and Future Directions," Adv. Mater. 10:1297-1336.
Allen et al. (Feb. 20, 2006) "Nanomaterial Transfer Using Hot Embossing for Flexible Electronic Devices," Appl. Phys. Lett. 88:083112.
Altman et al., "Silk-Based Biomaterials," Biomaterials 2003; 24 (3): 24:401-416.
Amano et al. (Feb. 3, 1986) "Metalorganic Vapor Phase Epitaxial Growth of a High Quality GaN Film Using an AIN Buffer Layer," Appl. Phys. Lett. 48(5):353-355.
Ambrosy et al. (1996) "Silicon Motherboards for Multichannel Optical Modules," IEEE Trans. Compon. Pack. A 19:34-40.

(56) References Cited

OTHER PUBLICATIONS

Amir et al. (2000) "The Influence of Helium-Neon Irradiation on the Viability of Skin Flaps in the Rat," Br. J. Plast. Surg. 53:58-62.
Amsden et al. (Nov. 9, 2009) "Spectral Analysis of Induced Color Change on Periodically Nanopatterned Silk Films," Opt. Express 17(23):21271-21279.
Andersen et al. (2004) "Selecting the Signals for a Brain—Machine Interface," Curr. Opin. Neurobiol. 14:720-726.
Andersson et al. (Oct. 16, 2002) "Active Matrix Displays Based on All-Organic Electrochemical Smart Pixels Printed on Paper," Adv. Mater. 14:1460-1464.
Ando et al. (2004) "Self-Aligned Self-Assembly Process for Fabricating Organic Thin-Film Transistors," Appl. Phys. Lett. 85:1849-1851.
Angadi et al. (Web Release Jun. 1, 2006) "Thermal Transport and Grain Boundary Conductance in Ultrananocrystalline Diamond Thin Films," J. Appl. Phys. 99:114301.
Aoki et al. (2003) "Microassembly of Semiconductor Three Dimensional Photonic Crystals," Nat. Mater. 2:117-121.
Arnold et al. (Web Release Dec. 28, 2002) "Field-Effect Transistors Based on Single Semiconducting Oxide Nanobelts," J. Phys. Chem. B 107(3):659-663.
Ayon et al. (Jan. 1999) "Characterization of a Time Multiplexed Inductively Coupled Plasma Etcher," J. Electrochem. Soc. 146(1):339-349.
Baca et al. (2008) "Semiconductor Wires and Ribbons for High-Performance Flexible Electronics," Angew. Chern. Int. Ed. 47:5524-5542.
Bae et al. (Jul. 1, 2002) "Single-Crystalline Gallium Nitride Nanobelts," Appl. Phys. Lett. 81: 126-128.
Ball et al. (2004) "Towards an Implantable Brain-Machine Interface Based on Epicortical Field Potentials," Biomed. Tech. 49:756-759.
Balmer et al. (2005) "Diffusion of Alkanethiols in PDMS and Its Implications on Microcontact Printing (IJCP)," Lanqmuir 21(2):622-632.
Banerjee et al. (May 2001) "3-D ICs: A Novel Chip Design for Improving Deep-Submicrometerinterconnect Performance and Systems-on-Chip Integration," Proc. IEEE 89(5):602-633.
Bao et al. (1997) "High-Performance Plastic Transistors Fabricated by Printing Techniques," Chem. Mater. 9:1299-1301.
Bao et al. (1999) "Printable Organic and Polymeric Semiconducting Materials and Devices," J. Mater. Chern. 9:1895-1904.
Barquins, M. (1992) "Adherence, Friction and Wear of Rubber-Like Materials," Wear 158:87-117.
Bates, F.S. (1991) "Polymer-Polymer Phase Behavior," Science 251:898-905.
Battaglia et al. (2003) "Colloidal Two-Dimensional Systems: CdSe Quantum Shells and Wells," Angew. Chem. Int. Ed. 442:5035-5039.
Bauer et al. (2004) "Biological Applications of High Aspect Ratio Nanoparticles," J. Mater. Chem. 14:517-526.
Berg et al. (2003) "Tailored Micropatterns Through Weak Polyelectrolyte Stamping," Langmuir 19:2231-2237.
Bernard et al. (1998) "Printing Patterns of Proteins," Langmuir 14(9):2225-2229.
Bett et al. (Aug. 1999) "III-V Compounds for Solar Cell Applications," Appl. Phys. A. Mater. Sci. 69(2):119-129.
Bhunia et al. (2004) "Free-Standing and Vertically Aligned InP Nanowires Grown by Metalorganic Vapor Phase Epitaxy," Physica E 21:583-587.
Bhushan et al. (2004) "Multiwalled Carbon Nanotube AFM Probes for Surface Characterization of Micro/Nanostructures," Microsyst. Technol. 10:633-639.
Bioflex—Biocompatible Flexible Electronic Circuits. Available at http:/tfcg.elis. Ugent.be/projects. Accessed Feb. 8, 2012.
Bietsch et al. (2000) "Conformational Contact and Pattern Stability of Stamps Used for Soft Lithography," J. Appl. Phys. 88:4310-4318.
Bishay et al. (2000) "Temperature Coefficient of the Surface Resistivity of Two-Dimensional Island Gold Films," J. Phys. D. Appl. Phys. 33(18):2218-2222.

Blanchet et al. (2003) "Large Area, High Resolution, Dry Printing of Conducting Polymers for Organic Electronics," Appl. Phys. Lett. 82:463-465.
Blanchet et al. (2003) "Printing Techniques for Plastic Electronics," J. Imag. Sci. Tech. 47(4):296-303.
Blazdell et al. (Nov. 1999) "Preparation of Ceramic Inks for Solid Freeforming Using a Continuous Jet Printer," J. Mat. Syn. Process. 7(6):349-356.
Boltau et al. (1998) "Surface-Induced Structure Formation of Polymer Blends on Patterned Substrates,"Nature 391:877-879.
Boncheva et al. (Mar. 15, 2005) "Magnetic Self-Assembly of Three-Dimensional Surfaces from Planar Sheets," Proc. Natl. Acad. Sci. USA 102(11):3924-3929.
Boncheva et al. (Mar. 18, 2005) "Templated Self-Assembly: Formation of Folded Structures by Relaxation of Pre-Stressed, Planar Tapes. The Path to Ubiquitous and Low-cost Organic Electronic Appliances on Plastic,"Ad. Mater. 17(5):553-557.
Bourzac, K. (May/Jun. 2010) "TR10: Implantable Electronics," Technology Review, Published by MIT, http://www.technologyreview.com/biomedicine/25086/?a=f.
Bowden et al. (1998) "Spontaneous Formation of Ordered Structures in Thin Films of Metals Supported on an Elastomeric Polymer," Nature 393:146-149.
Bowden et al. (2001) "Molecule-Mimetic Chemistry and Mesoscale Self-Assembly," Ace. Chem. Res. 34:231-238.
Bracher et al. (2009) "Shaped Films of Ionotropic Hydrogels Fabricated Using Templates of Patterns Paper," Adv. Mater. 21:445-450.
Bradley et al. (2003) "Flexible Nanotube Electronics," Nano Lett., vol. 3, No. 10, pp. 1353-1355.
Braun et al. (1999) "Electrochemically Grown Photonic Crystals," Nature 402:603-604.
Britton et al. (Web Release Oct. 25, 2005) "Microstructural Defect Characterization of a Si:H Deposited by Low Temperature HW-CVD on Paper Substrates," Thin Solid Films 501(1-2):79-83.
Brown et al. (2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," Biomaterials 26:3123-3129.
Brown et al. (Dec. 19, 2001) "Heterogeneous Materials Integration: Compliant Substrates to Active Device and Materials Packaging," Mater. Sci. Eng. B 87(3):317-322.
Brown, H.R. (1991) "The Adhesion Between Polymers," Ann. Rev. Mater. Sci. 21:463-489.
Bruschi et al. (2001) "Micromachined Silicon Suspended Wires With Submicrometric Dimensions," Microelectron. Eng. 57-58:959-965.
Buma et al. (2001) "High-Frequency Ultrasound Array Element Using Thermoelastic Expansion in an Elastomeric Film," Appl. Phys. Lett. 79:548-550.
Burdinski et al. (2005) "Single Etch Patterning of Stacked Silver and Molybdenum Alloy Layers on Glass Using Microcontat Wave Printing," J. Am. Chem. Soc. 127(31):10786-10787.
Burdinski, D. (non-dated) "Soft Lithography and Microcontact Wave Printing," htt,Q:/iINWW.research.Q,hili,Qs.comitechnologies/light deY microsys/softlitho/index.html, Downloaded May 23, 2007.
Burge et al. (Jun. 25, 1997) "X-Ray Holography for VLSI Using Synthetic Bilevel Holograms," Proc. Int. Soc. Opt. Eng. 3183:2-13.
Burgin et al. (2000) "Large Area Submicrometer Contact Printing Using a Contact Aligner," Langmuir 16:5371-5375.
Burns et al. (2003) "Printing of Polymer Thin-Film Transistors for Active-Matrix-Display Applications," J. Soc. Int. Display 11:599-604.
Campbell et al. (2000) "Fabrication of Photonic Crystals for the Visible Spectrum by Holographic Lithography," Nature 404:53-56.
Cao et al. (2006) "Highly Bendable,Transparent Thin-Film Transistors That Use Carbon-Nanotube-Based Conductors and Semiconductors with Elastomeric Delectrics," Adv. Mater. 18(3):304-309.
Cao et al. (2006) "Bilayer Organic-Inorganic Gate Dielectrics for High-Performance, Low-Voltage, Single-Walled Carbon Nanotube Thin-Film Transistors, Complementary Logic Gates, and p-n Diodes on Plastic Substrates," Adv. Funct. Mater. 16:2355-2362.
Cao et al. (2006) "Transparent flexible organic thin-film transistors that use printed single-walled carbon nanotube electrodes," Applied Physics Letters 88:113511.

(56) References Cited

OTHER PUBLICATIONS

Cao et al. (Jan. 5, 2009) "Ultrathin Films of Single-Walled Carbon Nanotubes for Electronics and Sensors: A Review of Fundamental and Applied Aspects," Adv. Mater. 21(1):29-53.

Cao et al. (Jul. 24, 2008) "Medium-Scale Carbon Nanotube Thin-Film Integrated Circuits on Flexible Plastic Substrates," Nature 454:495-500.

Carr et al. (1998) "Measurement of Nanomechanical Resonant Structures in Single-Crystal Silicon," J. Vac. Sci. Technol. B. 16:3821-3824.

Chadhury et al. (1991) "Direct Measurement of Interfacial Interactions Between Semispherical Lenses and Flat Sheets of Poly(dimethylsiloxane) and their Chemical Derivatives," Langmuir 7: 1013-1025.

Chang et al. (1994) "Process Techniques, Lithography and Device-Related Physics and Principles," In; GaAs High-Speed Devices: Physics, Technology and Circuit Application, John Wiley and Sons, New York, pp. 115-278.

Chen et al. (2003) "Characterization of Pd-GaAs Schottly Diodes Prepared by the Electrodes Plating Technique," Semiconductor. Sci. Technol. 18:620-626.

Chen et al. (2003) "Electronic Paper: Flexible Active-Matrix Electronics Ink Display," Nature 423: 136.

Chen et al. (2004) "Herringbone Buckling Patterns of Compresses Thin Films on Comlliant Substrates," J. Appl. Mech. 71 :597.

Chen et al. (2005) "InGaN Nanorings and Nanodots by Selective Area Epitaxy," Appl. Phys. Lett. 87:143111.

Chen et al. (2005) "The Role of Metal-Nanotube Caontact in the Performance of Carbon Nanotube Field-Effect Transistors," Nano Lett. 5(7):1497-1502.

Chen et al. (Feb. 27, 2006) "Complementary Carbon Nanotube-Gated Carbon Nanotube Thin-Fim Transistor," Appl. Phys. Lett. 88:093502.

Chen et al. (Jun. 2002) Effect of Process Parameters on the Surface Morphology and Mechanical Performance of Silicon Structures After Deep Reactive Ion Etching (DRIE) J. Microelectromech. Syst. 11 (3):264-2775.

Chen et al. (Mar. 2004) "A Family of Herringbone Patterns in Thin Films," Scr. Mater. 50(6):797-801.

Chen et al. (Mar. 24, 2006) "An Integrated Logic Circuit Assembled on a Single Carbon Nanotube," Science 311:1735.

Chen et al. (Sep. 2004) "Herringbone Buckling Patterns of Compressed Thin Films on Compliant Substrates," J. Appl. Mech. 71:597-603.

Cheng et al. (2005) "Ink-Jet Printing, Self-Assembled Polyelectrolytes, and Electroless Plating: Low Cost Fabrication of Circuits on a Flexible Substrate at Room Temperature," Macromol. Rapid Commun. 26:247-264.

Childs et al. (2002) "Decal Transfer Microlithography: A New Soft-Lithographic Patterning Method,"J. Am. Chern. Soc. 124:13583-13596.

Childs et al. (2005) "Masterless Soft-Lithography: Patterning UV/Ozone-Induced Adhesion on Poly(dimethylsiloxane) Surfaces," Langmuir 21:10096-10105.

Childs et al. (Aug. 14, 2004) "Patterning of Thin-Film Microstructures on Non-Planar Substrate Surfaces Using Decal Transfer lithography," Adv. Mater. 16(15):1323-1327.

Choi et al. (2007) "Biaxially Stretchable 'Wavy' Silicon Nanomembranes," Nano Lett. 7(6): 1655-1663.

Choi et al. (Web Release Jan. 25, 2005) "Simple Detachment Patterning of Organic Layers and Its Applications to Organic light-Emitting Diodes," Adv. Mater. 17(2):166-171.

Chou et al. (2004) "An Orientation-Controlled Pentacene Film Aligned by Photoaligned Polyimide for Organic Thin-Film Transistor Applications," Adv. Func. Mater. 14:811-815.

Chou et al. (Jun. 8, 1999) "Micromachining on (111 )-Oriented Silicon," Sens. Actuators A 75(3):271-277.

Chu et al. (2005) "High-Performance Organic Thin-Film Transistors with Metal Oxide/Metal Bilayer Electrode," Appl. Phys. Lett. 87: 193508.

Chung et al. (2000) "Silicon Nanowire Devices," Appl. Phys. Lett. 76(15):2068-2070 Chung et al. (Jul. 1,2003) "A Study on Formation of Al and Al2O3 on the Porous Paper by DC Magnetron Sputtering," Surf. Coat. Technol. 171(1-3):65-70.

Chung et al. (Jul. 1, 2003) "A Study on Formation of Al and Al2O3 on the Porous Paper by DC Magnetron Sputtering," Surf. Coat. Technol. 171(1-3):65-70.

Ciesinski, Michael, "Flexible Electronics: Why the Interest? Where are the Markets? What's Next?" *Flextech Alliance* Apr. 14, 2010, [retrieved online Apr. 29, 2011] http://www.avsusergroups.org/tfug_pdfs/tfug2010_4ciesinski.pdf.

Clerc, L. (1976) "Directional Differences of Impulse Spread in Trabecular Muscle from Mammalian Heart," J. Physiol. 255:335-346.

Cohen-Karni et al. (2009) "Flexible Electrical Recording from Cells Using Nanowire Transistor Arrays," Proc. Natl. Acad. Sci. USA 106:7309-7313.

Cole et al. (2008) "Patterned Growth and Transfer of ZnO Micro- and Nanocrystals with Size and Location Control," Adv. Mater. 20:1474-1478.

Collins et al. (Apr. 27, 2001) "Engineering Carbon Nanotubes and Nanotube Circuits Using Electrical Breakdown," Science 292:706-709.

Corazza et al. (2007) "Photobiomodulation on the Angiogenesis of Skin Wounds in Rats Using Different Light Sources," Photomedicine Laser Surg. 25:102-106.

Cox, H. L. (1952) "The Elasticity and Strength of Paper and Other Fibrous Materials," Br. J. Appl. Phys. 3:72-79.

Creagh et al. (2003) "Design and Performance of Inkjet Print Heads for Non-Graphic-Arts Applications," MRS Bull. 28:807-811.

Crone et al. (Feb. 3, 2000) "Large-Scale Complementary Integrated Circuits Based on Organic Transistors," Nature 403:521-523.

Crowder et al. (1998) "Low-Temperature Single-Crystal Si TFTs Fabricated on Si Films Processed via Sequential Lateral Solidification," IEEE Electron. Dev. Lett. 19:306-308.

Cui et al. (2001) "Nanowire Nanosensors for Highly Sensitive and Selective Detection of Biological and Chemical Species," Science 293:1289-1292.

Dai et al. (2002) "Gallium Oxide Nanoribbons and Nanosheets," J. Phys. Chem. B 106(5):902-904.

Dai et al. (2003) "Novel Nanostructures of Functional Oxides Synthesized by Thermal Evaporation," Adv. Funct. Mater. 13:9-24.

Dai et al. (Web Release Jan. 15, 2002) "Gallium Oxide Nanoribbons and Nanosheets," J. Phys. Chem. B 106(5):902-904.

Davidson et al. (2004) "Supercritical Fluid-liquid-Solid Synthesis of Gallium Arsenide Nanowires Arsenide Nanowires Seeded by Alkanethiol-Stabalized Gold Nanocrystals," Adv. Mater. 16:646-649.

de Gans (2004) "Inkjet Printing of Polymers: State of the Art and Future Developments," Adv. Mater. 16(3):203-213.

De Sio et al. (Web Release May 18, 2005) "Electro-Optical Response of a Single-Crystal Diamond Ultraviolet Photoconductor in Transverse Configuration," Appl. Phys. Lett. 86:213504.

DeBoer et al. (2004) "Organic Single-Crystal Field-Effect Transistors," *Phys. Stat. Sol.* 201 :1302-1331.

Deen et al. (2004) "Electrical Characterization of Polymer-Based FETs Fabricated by Spin-Coating Poly(3-alkythiophene)s," IEEE Trans. Electron Devices 51: 1892-1901.

Delmerche et al. (1997) "Stability of Molded Polydimethylsiloxane Microstructures," Adv. Mat. 9:741-746.

Deruelle et al. (1995) "Adhesion at the Solid-Elastomer Interface: Influence of Interfacial Chains," Macromol. 28:7419-7428.

Derycke et al. (Sep. 2001) "Carbon Nanotube Inter- and Intramolecular Logic Gates," Nano Lett. 1(9):453-456.

Desai et al. (Feb. 1999) "Nanopore Technology for Biomedical Applications," *Biomed. Microdevices* 2(1):11-40.

Dick et al. (2004) "Synthesis of Branched 'Nanotrees' by Controlled Seeding of Multiples Branching Events," Nat. Mater. 3:380-38.

Dimroth et al. (Mar. 2007) "High-Efficiency Multijunction Solar Cells," *MRS Bull.* 32:230-235.

Ding et al. (Oct. 4, 2004) "Self Catalysis and Phase Transformation in the Formation of CdSe Nanosaws," Adv. Mater. 16(19):1740-1743.

(56) References Cited

OTHER PUBLICATIONS

Dinsmore et al. (2002) "Colloidosomes: Selectively Permeable Capsules Composed of Colloidal Particles," Science 298:1006-1009.
Dinyari et al., (2008) "Curving Monolithic Silicon for Nonplanar Focal Plane Aarray Applications," Appl Phys Lett, 92:091114.
Divliansky et al. (2003) "Fabrication of Three-Dimensional Polymer Photonic Crystal Structures Using Single Diffraction Element Interference Lithography," Appl. Phys. Lett. 82(11):1667-1669.
Dodabalapur A. (Apr. 2006) "Organic and Polymer Transistors for Electronics," *Mater Today* 9(4):24-30.
Dodabalapur et al. (1995) "Organic Transistors: Two-Dimensional Transport and mproved Electrical Characteristics," Science 268:270-27.
Duan et al. (2000) "General Synthesis of Compound Semiconductor Nanowires," *Adv. Mater.* 12:298-302.
Duan et al. (2003) "High-performance Thin-Film Transistors Using Semiconductor Nanowires and Nanoribbons," Nature 425:274-278.
Duan X, (2003) "Semiconductor Nanowires: From Nanoelectronics to Macroelectronics," Abstract from a presentation given at the 11th Foresight Conference on Molecular Nanotechnology, Oct. 10-20, Burlingame, CA.
Duboz et al. (1998) "Transistors and Detectors Based on GaN-Related Materials," In; Group III Nitride Semiconductor Compounds, Gill, B. Ed., Clarendon, Oxford, pp. 343-387.
Duesberg et al. (2000) "Polarized Raman Spectroscopy on Isolated Single-Wall Carbon Nanotubes,"Phys. Rev. Lett., vol. 85, No. 25, pp. 5436-5439.
Duffy et al. (1998) "Rapid Prototyping of Microfluidic Systems in Poly(dimethylsiloxane)," Anal. Chern. 70(23):4974-4984.
Dupuis et al. (2008) "History, Development, and Applications of High-Brightness Visible Light-Emitting Diodes," IEEE J. Lightwave Tech. 26:1154-1171.
Durkop et al. (2004) "Extraordinary Mobility in Semiconducting Carbon Nanotube," *Nano Lett.* 4(1):35-39.
Eder et al. (Apr. 5, 2004) "Organic Electronics on Paper,"*Appl. Phys. Lett.* 84(14):2673-2675.
Edrington et al. (2001)"Polymer-Based Photonic Crystals," *Adv. Mater.* 13:421-425.
Efimenko et al. (Oct. 15, 2002) "Surface Modification of Sylgard-184 Poly(dimethyl Siloxane) Networks by Ultraviolet and UltravioleUOzone Treatment," J. Colloid Interface Sci. 254(2):306-315.
Eftekhari, G. (1993) "Variation in the Effective Richardson Constant of Metal-GaAs and Metal-InP Contacta Due to the Effect of Processing Parameters," Phys. Status Solid A—Appl. Res. 140:189-194.
Ensell, G. (1995) "Free Standing Single-Crystal Silicon Microstructures," *J.Micromech. Microeng.* 5: 1-4.
European Extended Search Report dated Feb. 9, 2012 in Application No. 09826745.3.
Examination Report, Clear Report, Corresponding to Malaysian Patent Application No. PI 20062672, issued May 13, 2011.
Examination Report, Corresponding to European Application No. EP 05 756 327.2, Dated Jan. 20, 2010.
Examination Report, Corresponding to Malaysian Patent Application No. PI20052553, Issued Feb. 27, 2009.
Examination Report, Corresponding to Malaysian Patent Application No. PI20092343, Issued May 26, 2012.
Examination Report, Corresponding to Malaysian Patent Application No. PI 20062672, Mailed Aug. 28, 2009.
Examination Report, Corresponding to Malaysian Patent Application No. PI20092343, Mailed Jun. 15, 2010.
Examination Report, Corresponding to Malaysian Patent Publication No. PI20052553, Mailed Mar. 13, 2009.
Examination Report, Corresponding to Singapore Patent Application No. 200608359-6, Completed on Aug. 27, 2008.
Faez et al. (1999) "An Elastomeric Conductor Based on Polyaniline Prepared by Mechanical Mixing," Polymer 40:5497-5503.
Felgner et al. (1996) "Flexural Rigidity of Microtubules Measured with the Use of Optical Tweezers," J. Cell Sci. 109:509-516.
Final Office Action, Corresponding to U.S. Appl. No. 12/575,008, mailed Oct. 17, 2011.
Final Office Action, Corresponding to U.S. Appl. No. 11/851,182, Mailed Oct. 29, 2010.
Fink et al. (1999) "Block Copolymers as Photonic Bandgap Materials," *J. Lightwave Tech.* 17:1963-1969.
Flewitt et al. (2005) "Low-Temperature Deposition of Hydrogenated Amorphous Silicon in an Electron Cyclotron Resonance Reactor for Flexible Displays," Proc. IEEE 93: 1364-1373.
Folch et al. (1999) "Wafer-Level In-Registry Microstamping," *J. Microelectromech. Syst.* 8:85-89.
Forment et al. (2004) "Influence of Hydrogen Treatment and Annealing Processes Upon the Schottky Barrier Height of Au/n-GaAs and Ti/n-GaAs Diodes," Semicond. Sci. Technol. 19:1391-1396.
Forrest et al. (2004) "The Path to Ubiquitous and Low-Cost Organic Electronic Appliances on Plastic," Nature 428:911-918.
Fortunato et al. (2005) "Flexible a-Si: H Position-Sensitive Detectors," *Proc. IEEE* 93:1281-1286.
Fortunato et al. (Sep. 2008) "High-Performance Flexible Hybrid Field-Effect Transistors Based on Cellulose Fiber Paper," IEEE Electron. Dev. Lett. 29(9):988-990.
Freeman et al. (2000) "Spatial Spectral Analysis of Human Electrocardiograms Including the Alpha and Gamma Bands," J. Neurosci. Methods 95:111-121.
Freire et al. (1999) "Thermal Stability of Polyethylene Terephthalate (PET): Oligomer Distribution and Formation of Volatiles," Packag. Technol. Sci. 12:29-36.
Freund, L.B. (2000) "The Mechanics of Electronic Materials," *Int. J. Solids Struct.* 37:185-196.
Friedman et al. (2005) "Nanotechnology: High-Speed Integrated Nanowire Circuits," Nature 434:1085.
Fu et al. (Jan. 10, 2003) "Patterning of Diamond Microstructures on Si Substrate by Bulk and Surface Micromachining," J. Mater. Process. Technol. 132(1-3):73-81.
Furneaux et al. (1989) "The Formation of Controlled-Porosity Membranes from Anodically Oxidized Aluminum," Nature 337:147-149.
Gan et al. (2002) "Preparation of Thin-Film Transistors with Chemical Bath Deposited CdSe and CdS Thin Films," IEEE Trans. Electron. Dev. 49:15-18.
Gao et al. (Sep. 9, 2005) "Conversion of Zinc Oxide Nanobelts into Superlattice-Structures Nanohelices," Science 309: 1700-1704.
Garcia et al. (Oct. 2004) "Etchant Anisotropy Controls the Step Bunching Instability in KOH Etching of Silicon," Phys. Rev. Lett. 93(16):166102.
Gardner et al. (1965) "Physical Aspects of the Internal Water Relations of Plant Leaves," Plant Physiol. 40:705-710.
Garnier et al. (1994) "All-Polymer Field-Effect Transistor Realized by Printing Techniques," Science 265:1684-1686.
Geim et al. (Mar. 2007) "The Rise of Graphene," *Nature Mater.* 6:183-191.
Geissler et al. (2003) "Fabrication of Metal Nanowires Using Microcontact Printing," Langmuir 19(15):6301-6311.
Geissler et al. (Jun. 2003) "Selective Wet-Etching of Microcontact-Printed Cu Substrates with Control Over the Etch Profile," Microelec. Eng. 67-68:326-332.
Gelinck et al. (2000) "High-Performance All-Polymer Integrated Circuits," *Appl. Phys. Lett.* 77:1487-1489.
Gelinck et al. (2004) "Flexible Active-Matrix Displays and Shift Registers Based on Solution-Processed Organic Transistors," Nat. Mater. 3: 106-110.
Georgakilas et al. (2002) "Wafer-Scale Integration of GaAs Optoelectronic Devices with Standard Si Integrated Circuits Using a Low-Temperature Bonding Procedure," Appl. Phys. Lett. 81:5099-5101.
Givargizov, E.I. (1991) "Applications," In; *Oriented Crystallization on Amorphous Substrates*, Plenum Press, New York, pp. 341-363.
Goetting et al. (1999) "Microcontact Printing of Alkanephosphonic Acids on Aluminum: Pattern Transfer by Wet Chemical Etching," *Langmuir* 15:1182-1191.
Goldman et al. (1996) "Correlation of Buffer Strain Relaxation Modes with Transport Properties of Two-Dimensional Electron Gases," *J. Apple. Phys.* 80:6849-6854.

(56) References Cited

OTHER PUBLICATIONS

Goldmann et al. (2004) "Hole Mobility in Organic Single Crystals Measured by a "Flip Crystal"Field-Effect Technique," *J. Appl. Phys.* 96:2080-2086.
Goldsmith, T.H. (Sep. 1990) "Optimization, Constraint, and History in the Evolution of Eyes," *Quart. Rev. Biol.* 65(3):281-322.
Gratz et al. (1991) "Atomic Force Microscopy of Atomic-Scale Ledges and Etch Pits Formed During Dissolution of Quartz," *Science*, 251:1343-1346.
Gray et al. (2004) "High-Conductivity Elastomeric Electronics," *Adv. Mater.* 16:393 397.
Gray et al. (Dec. 2001) "Screen Printed Organic Thin Film Transistors (OTFTs) on a Flexible Substrate," *Proc. SPIE* 4466:89-94.
Grayson, T. (2002) "Curved Focal Plane Wide Field of View Telescope Design," *Proc. SPIE* 4849:269-274.
Gruen et al. (Mar. 21, 1994) "Fullerenes as Precursors for Diamond Film Growth Without Hyrdogen or Oxygen Additions," *Appl. Phys. Lett.* 65(12):1502-1504.
Gudiksen et al. (Web Release Apr. 18, 2001) "Synthetic Control of the Diameter and Length of Single Crystal Semiconductor Nanowires," *J. Phys. Chem.* B 105:4062-4064.
Guo et al. (Aug. 19, 2002) "Metal-Insulator-Semiconductor Electrostatics of Carbon Nanotubes," *Appl. Phys. Lett.* 81(8):1486-1488.
Gur et al. (2005) "Air-Stable All-Inorganic Nanocrystal Solar Cells Processed from Solution," *Science* 310:462-465.
Gurbuz et al. (Jul. 2005) "Diamond Semiconductor Technology for RF Device Applications." *Solid State Electron*. 49(7): 1055-1070.
Haisma et al. (2002) "Contact Bonding, Including Direct-Binding in a Historical and Recent Context of Materials Science and Technology, Physics and Chemistry—Historical Review in a Broader Scope and Comparative Outlook," *Mater. Sci. Eng.* R 37:1-60.
Halik et al. (2004) "Low-Voltage Organic Transistors with an Amorphous Molecular Gate Dielectric," *Nature* 431 :963-966.
Hamedi et al. (May 2007) "Towards Woven Logic from Organic Electronic Fibres," *Nat. Mater.* 6:357-362.
Hamilton et al. (2004) "Field-Effect Mobility of Organic Polymer Thin-Film Transistors," *Chem. Mater.* 16:4699-4704.
Han et al. (2005) "Template-Free Directional Growth of Single-Walled Carbon Nanotues on a-and r-Plane Sapphire," *J. Am. Chem. Soc.* 127:5294-5295.
Harada et al. (2001) "Catalytic Amplification of the Soft Lithographic Patterning of Si. Nonelectrochemical Orthogonal Fabrication of Photoluminescent Porous Si Pixel Arrays," *J. Am. Chem. Soc.* 123:8709-8717.
Harkonen et al. (Jun. 8, 2006) "4 W Single-Transverse Mode VECSEL Utilizing Intra-Cavity Diamond Heat Spreader," *Electron Lett.* 42(12):693-694.
Hayase et al. (2001) "Photoangioplasty with Local Motexafin Lutetium Delivery Reduces Macrophages in a Rabbit Post-Balloon Injury Model," *Cardiovascular Res.* 49:449-455.
He et al. (2005) "Si Nanowire Bridges in Microtrenches: Integration of Growth into Device Fabrication," *Adv. Mater.* 17:2098-2102.
Heffelfinger et al. (1997) "Steps and the structure of the (0001) α-alumina surface," *Surf. Sci.*, 370:L168-L172.
Hillbrog et al. (Web Release Dec. 30, 2003) "Nanoscale Hydrophobic Recovery: Chemical Force Microscopy Study of UV/Ozone-Treated Cross-Linker Poly(dimethylsiloxane)," *Langmuir* 20(3):785-794.
Hines et al. (2005) "Nanotransfer Printing of Organic and Carbon Nanotube Thin-Film Transistors on Plastic Substrates," *Appl. Phys. Lett.* 86:163101.
Hollenberg et al. (2006) "A MEMS Fabricated Flexible Electrode Array for Recording Surface Field Potentials," *J. Neurosci. Methods* 153:147-153.
Holmes et al. (Feb. 25, 2000) "Control of Thickness and Orientation of Solution—Grown Silicon Nanowires," *Science* 287:1471-1473.
Horan et al. (Jun. 2005) "In Vitro Degradation of Silk Fibroin," *Biomaterials* 26(17):3385-3393.
Horn et al. (1992) "Contact Electrification and Adhesion Between Dissimilar Materials," *Science* 256:362-364.
Hoyer, P. (1996) "Semiconductor Nanotube Formation by a Two-Step Template Process," *Adv. Mater.* 8:857-859.
Hsia et al. (2005) "Collapse of Stamps for Soft Lithography Due to Interfacial Adhesion," *Appl. Phys. Lett.* 86:154106.
Hsu et al. (2002) "Amorphous Si TFTs on Plastically Deformed Spherical Domes," *J. Non-Crystalline Solids* 299-302: 1355-1359.
Hsu et al. (2003) "Nature of Electrical Contacts in a Metal-Molecule-Semiconductor System," *J. Vac. Sci. Technol.* B 21(4):1928-1935.
Hsu et al. (2004) "Effects of Mechanical Strain on TFTs on Spherical Domes," *IEEE Trans. Electron. Dev.* 51 :371-377.
Hsu et al. (Jan. 15,2004) "Spherical Deformation of Compliant Substrates with Semiconductor Device Islands," *J. Appl. Phys.* 95(2):705-712.
Hsu et al. (Mar. 2004) "Effects of Mechanical Strain on TFT's on Spherical Domes," IEEE Trans. Electron Dev. 51(3):371-377.
Hu et al. (1997) "Using Soft Lithography to Fabricate GaAs/AlGaAs Heterostructure Field Effect Transistors," *Appl. Phys. Lett.* 71 :2020-2022.
Hu et al. (1999) "Chemistry and Physics in One Dimension: Synthesis and Properties of Nanowires and Nanotubes," *Ace. Chem. Res.* 32:435-445.
Hu et al. (2004) "Percolation in Transparent and Conducting Carbon Nanotube Networks," Nano Lett., vol. 4, No. 12, pp. 2513-2517.
Hu et al. (2009) "Highly Conductive Paper for Energy-Storage Devices," Proc. Natl. Acad. Sci. USA 106:21490-21494.
Hu et al. (2010) "Stretchable, Porous, and Conductive Energy Textiles," Nano Lett. 10:708-714.
Huang et al. (2001) "Directed Assembly of One-Dimensional Nanostructures into Functional Networks," *Science* 291 :630-633.
Huang et al. (2001) "Room-Temperature Ultraviolet Nanowire Nanolasers," Science 292:1897-1899.
Huang et al. (2003) "Growth of Millimeter-Long and Horizontally Aligned Single-Walled Carbon Nanotubes on Flat Substrates," J. Am. Chem. Soc., 125:5636-5637.
Huang et al. (2004) "Long and Oriented Single-Walled Carbon Nanotubes Grown by Ethanol Chemical Vapor Deposition," J. Phys. Chem. B. 108:16451-16456.
Huang et al. (2004) "Self-Organizing High-Density Single-Walled Carbon Nanotube Arrays from Surfactant Suspensions," Nanotechnol. 15:1450-1454.
Huang et al. (2005) "Nanomechanical Architecture of Strained Bilayer Thin Films: From Design Principles to Experimental Fabrication," *Adv. Mater.* 17(23):2860-2864.
Huang et al. (2005) "Nanowires for Integrated Multicolor Nanophotonics," *Small* 1(1):142-147.
Huang et al. (2005) "Nonlinear Analyses of Wrinkles in a Film Bonded to a Compliant Substrate," *J. Mech. Phys. Solids* 53:2101-2118.
Huang et al. (2005) "Stamp Collapse in Soft Lithography," *Langmuir* 21 :8058-8068.
Huang et al. (Jan. 16, 2001) "Catalytic Growth of Zinc Oxide Nanowires by Vapor Transport," *Adv. Mater.* 13(2):113-116.
Huck et al. (2000) "Ordering of Spontaneously Formed Buckles on Planar Surfaces," *Langmuir* 16:3497-3501.
Huie, J.C. (2003) "Guided Molecular Self-Assembly: A Review of Recent Efforts," *Smart Mater. Struct.* 12:264-271.
Huitema et al. (2001) "Plastic Transistors in Active-Matrix Displays," *Nature* 414:599.
Hur et al. (2005) "Organic Nanodelectrics for Low Voltage Carbon Nanotube Thin Film Transistors and Complementary Logc Gates," *J. Am. Chem. Soc.* 127:13808-13809.
Hur et al. (2005) "Printed thin-film transistors and complementary logic gates that use polymer-coated single-walled carbon nanotube networks," J. Appl. Phys., 98, 114302.
Hur et al. (Dec. 2004) "Nanotransfer Printing by Use of Noncovalent Surface Forces: Applications to Thin-Film Transistors that Use Single-Walled Carbon Nanotube Networks and Semiconducting Polymers," *Appl. Phys. Lett.* 85(23):5730-5732.
Hur et al. (Jun. 13,2005) "Extreme Bendability of Single Walled Carbon Nanotube Networks Transferred From High-Temperature Growth Substrates to Plastic and Their Use in Thin-Film Transistors," *Appl Phys. Lett.* 243502.

(56) References Cited

OTHER PUBLICATIONS

Hutchinson et al. (1992) "Mixed Mode Cracking in Layered Materials," *Adv. Appl. Mech.* 29:63-191.

Imparato et al. (2005) "Excimer Laser Induced Crystallization of Amorphous Silicon on Flexible Polymer Substrates," *Thin Solid Films* 487:58-62.

International Preliminary Report on Patentability for PCT Application PCT/US2009/067670, mailed Jun. 14, 2011.

International Preliminary Report on Patentability for PCT Application PCT/US2010/051196, mailed Apr. 12, 2012.

International Search Report and Written Opinion, Corresponding to International Application No. PCT/2005/014449, Mailed Jul. 3, 2008.

International Search Report and Written Opinion, Corresponding to International Application No. PCT/US07/77759, Mailed Apr. 11, 2008.

International Search Report and Written Opinion, Corresponding to International Application No. PCT/US10/50468, Mailed Jan. 6, 2011.

International Search Report and Written Opinion, Corresponding to International Application No. PCT/US10/60425, Mailed May 25, 2011.

International Search Report and Written Opinion, Corresponding to International Application No. PCT/US07/74293, Mailed Jul. 24, 2008.

International Search Report and Written Opinion, Corresponding to International Application No. PCT/US07/77217, Mailed Jun. 3, 2008.

International Search Report and Written Opinion, Corresponding to International Application No. PCT/US07/82633, Mailed May 16, 2008.

International Search Report and Written Opinion, Corresponding to International Application No. PCT/US09/47442, Mailed Sep. 21, 2009.

International Search Report and Written Opinion, Corresponding to International Application No. PCT/US2006/032125, Mailed Mar. 21, 2008.

International Search Report and Written Opinion, Corresponding to International Application No. PCT/US2009/036192, Mailed Jul. 6, 2009.

International Search Report and Written Opinion, Corresponding to International Application No. PCT/US2009/058231, Mailed Nov. 17, 2009.

International Search Report and Written Opinion, Corresponding to International Application No. PCT/US2010/027209, Mailed Nov. 11, 2010.

International Search Report and Written Opinion, Corresponding to International Application No. PCT/US2010/034520, Mailed Sep. 24, 2010.

International Search Report and Written Opinion, Corresponding to International Application No. PCT/US2010/042585, Mailed May 25, 2011.

International Search Report and Written Opinion, Corresponding to International Application No. PCT/US2011/028094, Mailed Jul., 14, 2011.

International Search Report and Written Opinion, Corresponding to International PCT Application No. PCT/US2006/021161, Mailed Feb. 28, 2008.

International Search Report and Written Opinion, Corresponding to International PCT Application No. PCT/US2007/077759, Mailed Apr. 11, 2008.

International Search Report and Written Opinion, Corresponding to International PCT Application No. PCT/US2007/079070, Mailed Apr. 23, 2008.

International Search Report and Written Opinion, Corresponding to International PCT US2010/061151.

International Search Report and Written Opinion, Corresponding to International PCT Application No. PCT/US05/19354 Mailed Apr. 18, 2007.

International Search Report Corresponding to International Application No. PCT/US2009/036956, mailed Jun. 29, 2009.

International Search Report, Corresponding to International Application No. PCT/US2009/059892, mailed Jan. 7, 2010.

International Search Report, Corresponding to International Application No. PCT/US2009/064199, mailed May 20, 2011.

International Search Report, Corresponding to International Application No. PCT/US2009/065806, mailed Jun. 1, 2010.

International Search Report, Corresponding to International Application No. PCT/US2009/067670, mailed Aug. 4, 2010.

International Search Report, Corresponding to International Application No. PCT/US2010/020742, mailed Sep. 14, 2010.

International Search Report, Corresponding to International Application No. PCT/US2010/051196, mailed Dec. 1, 2010.

International Search Report Corresponding to International Application No. PCT/US2011/031648, mailed Dec. 15, 2011.

Isberg et al. (Sep. 6, 2002) "High Carrier Mobility in Single-Crystal Plasma-Deposited Diamond," *Science* 297:1670-1672.

Islam et al. (Jan. 16, 2003) "High Weight Fraction Surfactant Solubilization of Single-Wall Carbon Nanotubes in Water," *Nano Lett.* 3(2):269-273.

Ismach et al. (2004) "Atomic-Step-Templated Formation or a Single Wall Carbon Nanotube Patterns," *Angew. Chem. Int. Ed.* 43:6140-6143.

Itoh et al. (1991) "Cathodoluminescence Properties of Undoped and Zn-Doped $Al_xGa_{1-x}N$ Grown by Metaloganic Vapor Phase Epitaxy," *Jap. J. Appl. Phys.* 30: 1604-1608.

Jabbour et al. (2001) "Screen Printing for the Fabrication of Organic Light-Emitting Devices," *IEEE J. Select. Top. Quantum. Electron.* 7(5):769-773.

Jackman et al. (Aug. 4, 1995) "Fabrication of Submicrometer Features on Curved Substrates by Microcontact Printing," *Science* 269:664-666.

Jacobs et al. (2001) "Submicrometer Patterning of Charge in Thin-Film Electrets," *Science* 291:1763-1766.

Jacobs et al. (2002) "Fabrication of a Cylindrical Display by Patterned Assembly," *Science* 296:323-325.

Jain et al. (2000) "Ill-Nitrides: Growth, Characterization, and Properties," *J. Appl. Phys.* 87:965-1006.

Jain et al. (2005) "Flexible Electronics and Displays: High-Resolution, Roll-to-Roll, Projection Lithography and Photoblation processing Technologies for Hiogh—Throughput Production," *Proc. IEEE* 93:1500-1510.

James et al. (1998) "Patterned Protein Layers on Solid Substrates by This Stamp Microcontact Printing," *Langmuir* 14:742-744.

Jang et al. (2003) "Lateral Growth of Aligned Multiwalled Carbon Nanotubes Under Electric Fiels," Solid State Commun. 126:305-308.

Jang et al. (2006) "Low-Voltage and High-Field-Effect Mobility Organic Transistors with a Polymer Insulator," *Appl. Phys. Lett.* 88:072101.

Javey et al. (2002) "High-K Dielectrics for Advanced Carbon-Nanotube Transistors and Logic Gates," *Nature Mater.* 1:241-246.

Javey et al. (2005) "High Performance n-Type Carbon Nanotube Field-Effect Transistors with Chemically Doped Contacts," *Nano Lett.*, vol. 5, No. 2, pp. 345-348.

Javey et al. (Aug. 7, 2003) "Ballistic Carbon Nanotube Field-Effect Transistors," *Nature* 424:654-657.

Jenkins et al. (1994) "Gallium Arsenide Transistors: Realization Through a Molecularly Designed Insulator," *Science* 263:1751-1753.

Jeon et al. (1995) "Patterning of Dielectric Oxide Thin Layers by Microcontact Printing of Self-Assembled Monolayers," *J. Mater. Res* 10:2996-2999.

Jeon et al. (2003) "Structural and Mechanical Properties of Woven Fabrics Employing Peirce's Model," Textile Res. J. 73:929-933.

Jeon et al. (2004) "Fabricating Complex Three-Dimensional Nanostructures with High Resolution Comfortable Phase Masks," *Proc. Nat!. Acad. Sci. USA* 101:12248-12433.

Jeon et al. (2004) "Three Dimensional Nanofabrication with A rubber Stamps and Comformable Photomasks," Adv. Mater. 16:593-600.

Jeon et al. (Aug. 4, 2004) "Three Dimensional Nanofabrication with Rubber Stamps and Conformable Photomasks," *Adv. Mater.* 16(15):1369-1373.

(56) References Cited

OTHER PUBLICATIONS

Jiang et a. (Oct. 2, 2007) "Finite Deformation Mechanics in Buckled Thin Films on Compliant Supports," *Proc. Natl. Acad. Sci. USA* 104(40):15607-15612.

Jiang et al. (1999) "Preparation of Macroporous Metal Films from Colloidal Crystals," *J. Am. Chem. Soc.* 121:7957-7958.

Jiang et al. (2002) "Polymer-on-Polymer Stamping: Universal Approaches to Chemically Patterned Surfaces," *Langmuir* 18:2607-2615.

Jiang et al. (2007) "Mechanical Properties of Robust Ultrathin Silk Fibroin Films," Adv. Funct. Mater. 17:2229-2237.

Jin et al. (2004) "Scalable Interconnection and Integration of Nanowire Devices Without Registration," *Nano Lett.* 4:915-919.

Jin et al. (2004) "Soft Lithographic Fabrication of an Image Senbsor Array on a Curved Subsrate," *J. Vac. Sci. Technol.* B 22:2548-2551.

Jin et al. (Aug. 2005) "Water-Stable Silk Films with Reduced β-Sheet Content," Adv. Funct. Mater. 15(8):1241-1247.

Jin et al. (Web Release Jan. 23, 2004) "Biomaterial Films of Bornbyx mori Silk Fibroin with Poly(ethyleneoxide)," Biomacromolecules 5(3):711-717.

Jiyun, C.H. (2003) "Guided Molecular Self-Assembly: A Review of Recent Efforts," Smart Mater. Struct. 12:264-271.

Joachim et al. (Nov. 30, 2000) "Electronics Using Hybrid-Molecular and Mono-Molecular Devices," *Nature* 408:541-548.

Johnson et al. (1999) "Ordered Mesoporous Polymers of Tunable Pore Size from Colloidal Silica Templates," *Science* 283:963-965.

Jones et al. (Jul./Aug. 2004) "Stretchable Wavy Metal Interconnects," *J. Vac. Sci. Technol. A.* 22(4):1723-1725.

Joo et al. (2006) "Low-Temperature Solution-Phase Synthesis of Quantum Well Structures CdSe Nanoribbons," *J. Am. Chem. Soc.* 128(17):5632-5633.

Jortner et al. (2002) "Nanostructured Advanced Materials Perspectives and Directions," *Pure Appl. Chern.* 74(9):1491-1506.

Joselevich (2002) "Vectorial Growth of Metallic and Semiconducting Single-Wall Carbon Nanotubes," Nano Lett., vol. 2, No. 10, pp. 1137-1141.

Kadish et al. (1988) "Interaction of Fiber Orientation and Direction of Impulse Propagation with Anatomic Barriers in Anisotropic Canine Myocardium," Circulation. 78:1478-1494.

Kagan (1999) "Organic-Inorganic Hybrid Materials as Semiconducting Channels in Thin-Film Field-Effect Transistors," *Science* 286:945-947.

Kagan et al. (2001) "Patterning Organic-Inorganic Thin-Film Transistors Using Microcontact Printed Templates," *Appl. Phvs Lett.* 79(21):3536-3538.

Kagan et al. (2003) "Thin Film Transistors—A Historical Perspective," In; *Thin Film Transistors*, Dekker, New York, pp. 1-34.

Kane et al. (2000) "Analog and Digital Circuits Using Organic Thin-Film Transistors on Polyester Substrates," *IEEE Electron. Dev. Lett.* 21 :534-536.

Kang et al. (2007) "High-Performance Electronics Using Dense, Perfectly Aligned Arrays of Single-Walled Carbon Nanotubes," *Nat. Nanotechnol.* 2:230-236.

Kang et al. (2007) "Printed Multilayer Superstructures of Aligned Single-Walled Carbon Nanotubes for Electronic Applications," Nano Lett. 7(11):3343-3348.

Kar et al. (Web Release Feb. 18,2006) "Shape Selective Growth of CdS One-Dimensional Nanostructures by a Thermal Evaporation Process," *J. Phys. Chern.* B. 110(10):4542-4547.

Kar et al. (Web Release Feb. 8, 2005) "Controlled Synthesis and Photoluminescence Properties of ZnS Nanowires and Nanoribbons," *J. Phys. Chem.* B 109(8):3298-3302.

Kar et al. (Web Release Sep. 28, 2005) "Synthesis and Optical Properties ofCdS Nanoribbons," *J. Phys. Chem* B. 109(41):19134-19138.

Karnik et al. (2003) "Lateral Polysilicon $p^+$-p-$n^+$ and $p^+$-n-$n^+$ Diodes," *Solid-State Electronics* 47:653-659.

Karnik et al. (2003) "Multiple Lateral Polysilicon Diodes as Temperature Sensors for Chemical Microreaction Systems," *Jpn. J. Appl. Phys.* 42:1200-1205.

Kato et al. (2004) "The Characteristic Improvement of Si(111) Metal-Oxide-Semiconductor Field-Effect Transistor by Long-Time Hydrogen Annealing," *Jpn. J. Appl. Phys.* 43(10):6848-6853.

Katz et al. (2001) "Synthetic Chemistry for Ultrapure, Processable, and High-Mobility Organic Transistor Semiconductors," *Ace. Chem. Res.* 34:359-369.

Katz, H.E. (2004) "Recent Advances in Semiconductor Performance and Printing Processes for Organic Transistor-Based Electronics," *Chem. Mater.* 16:4748-4756.

Kawata et al. (2001) "Finer Features for Functional Microdevices," *Nature* 412:697-698.

Kellis et al. (2009) "Human Neocortical Electrical Activity Recorded on Nonpenetrating Microwire Arrays: Applicability for Neuroprostheses," Neurosurg. Focus 27(1):E9.

Kendall, D.L. (1979) "Vertical Etching of Silicon at Very High Apect Ratios," *Ann. Rev. Mater. Sci.* 9:373-403.

Khakani et al. (2006) "Lateral Growth of Single Wall Carbon Nanotubes on Various Substrates by Means of an 'All-Laser' Synthesis Approach," Diamond Relat. Mater. 15:1064-1069.

Khan et al. (1993) "High Electron Mobility Transistor Based on a GaN-$Al_xGa_{1-x}$N Heterojunction," *Appl. Phys. Lett.* 63:1214-1215.

Khang et al. (2006) "A Stretchable Form of Single-Crystal Silicon for High-Performance Electronics on Rubber Substraights," *Science* 311 :208-212.

Kilby, J.S. (1976) "Invention of the Integrated Circuit," *IEEE Trans. Electron. Dev* 23:648-654.

Kim et al. (2000) "Field Emission from Carbon Nanotubes for Displays," *Diamond and Related Mater* 9(3-6): 1184-1189.

Kim et al. (2002) "Nanolithography Based on Patterned Metal Transfer and its Application to Organic Electronic Devices," *Appl. Phys. Lett.* 80:4051-4053.

Kim et al. (2003) "Epitaxial self-assembly of block copolymers on lithographically defined nanopatterned substrates," *Nature* 424:411-414.

Kim et al. (2008) "Materials and Noncoplanar Mesh Designs for Integrated Circuits with Linear Elastic Responses to Extreme Mechanical Deformations," *Proc. Natl. Acad. Sci. USA* 105(48):18675-18680.

Kim et al. (2008) "Stretchable and Foldable Silicon Integrated Circuits," *Science* 320:507-511.

Kim et al. (2008) "Stretchable Electronics: Materials Strategies and Devices," Adv. Mater. 20:4887-4892.

Kim et al. (2009) "Integrated Wireless Neural Interface Based on the Utah Electrode array," Biomed. Microdevices 11:453-466.

Kim et al. (2009) "Optimized Structural Designs for Stretchable Silicon Integrated Circuits," Small 5(24):2841-2847.

Kim et al. (Dec. 2, 2008) "Materials and Noncoplanar Mesh Designs for Integrated Circuits with Linear Elastic Responses to Extreme Mechanical Deformations," Proc. Natl. Acad. Sci. USA 105(48):18675-18680.

Kim et al. (Jan. 2008) "Complementary Logic Gates and Ring Oscillators Plastic Substrates by Use of Printed Ribbons Single-Crystalline Silicon," *IEEE Electron. Dev. Lett.* 29(1):73-76.

Kim et al. (Nov. 15, 1999) "Direct Observation of Electron Emission Site on Boron—Doped Polycrystalline Diamond Thin Films Using an Ultra-High-Vacuum Scanning Tunneling Microscope," *Appl. Phys. Lett.* 75(20):3219-3221.

Kim et al. (Oct. 17, 2010) "Waterproof AllnGaP optoelectronics on stretchable substrates with applications in biomedicine and robotics," Nature Materials 9:929-937.

Kim et al. (Oct. 2004) "Organic TFT Array on a Paper Substrate," *IEEE Electron. Dev.Lett.* 25(10):702-704.

Kim et al. (Web Release Apr. 18, 2010) "Dissolvable Films of Silk Fibroin for Ultrathin Conformal Bio-Integrated Electronics," Nature Materials 9:511-517.

Kim et al. (Web Release Feb. 29, 2008) "Highly Emissive Self-Assembled Organic Nanoparticles Having Dual Color Capacity for Targeted Immunofluorescence Labeling," *Adv. Mater.* 20(6):1117-1121.

Kim et al. (Web Release Jul. 31, 2008) "Complementary Metal Oxide Silicon Integrated Circuits Incorporating Monolithically Integrated Stretchable Wavy Interconnects," Appl. Phys. Lett. 93(4):044102.

(56) References Cited

OTHER PUBLICATIONS

Kim et al. (Web Release Jul. 6, 2009) "Ultrathin Silicon Circuits with Strain-Isolation Layers and Mesh Layouts for High-Performance Electronics on Fabric, Vinyl, Leather and Paper," *Adv. Mater.* 21(36):3703-3707.
Kim et al. (Web Release Sep. 29, 2009) "Silicon Electronics on Silk as a Path to Bioresorbable, Implantable Devices," Appl. Phys. Lett. 95:133701-133703.
Kim et al., (2008) "Complimentary Metal Oxide Silicon Integrated Circuits Incorporating Monolithically Integrated Stretchable Wavy Interconnects," Appl Phys Lett, 93:044102.
Kim, Y.S. (Web Release Aug. 9, 2005) "Microheater-Integrated Single Gas Sensor Array Chip Fabricated on Flexible Polyimide Substrate," *Sens. Actuators* B 114(1):410-417.
Klauk et al. (2002) "High-Mobility Polymer Gate Dielectric Pentacene Thin Film Transistors," *J. Appl. Phys.* 92:5259-5263.
Klein-Wiele et al. (2003) "Fabrication of Periodic Nanostructures by Phase-Controlled Multiple-Beam Interference," *Appl. Phys. Lett.* 83(23):4707-4709.
Knipp et al. (2003) "Pentacine Thin Film Transistors on Inorganic Dielectrics: Morphology, Structural Properties, and Electronic Transport," *J Appl. Phys.* 93:347-355.
Ko et al. (2006) "Bulk Quantities of Single-Crystal Silicon Micro-/Nanoribbons Generated from Bulk Wafers," *Nano Lett.* 6(10):2318-2324.
Ko et al. (2008) "A Hemispherical Electronic Eye Camera Based on Compressible Silicon Optoelectronics," *Nature* 454:748-753.
Ko et al. (2010) "Flexible Carbon Nanofiber Connectors with Anisotropic Adhesion Properties," *Small* 6:22-26.
Ko et al. (Web Release Oct. 28, 2009) "Curvilinear Electronics Formed Using Silicon Membrane Circuits and Elastomeric Transfer Elements," *Small* 5(23):2703-2709.
Kocabas et al. (2004) "Aligned Arrays of Single-Walled Carbon Nanotubes Generated from Random Networks by Orientationally Selective Laser Ablation," Nano Lett., vol. 4, No. 12, pp. 2421-2426.
Kocabas et al. (2005) "Guided Growth of Large-Scale, Horizontally Aligned Arrays of Single-Walled Carbon Nanotubes and Their Use in Thin-Film Transstors," *Small* 1(11): 111 0-1116.
Kocabas et al. (2006) "Spatially Selective Guided Growth of High-Coverage Arrays and Random Networks of Single-Walled Carbon Nanotbes and Thir Integration into Electronic Devices," *J. Am. Chem. Soc.* 128:4540-4541.
Kocabas et al. (2006) "Large Area Aligned Arrays of SWNTs for High Performance Thin Film Transistors," American Physical Society, APS March Meeting, Mar. 13-17, Abstract # W31.004.
Kocabas et al. (2007) "Experimental and Theoretical Studies of Transport Through Large Scale, Partially Aligned Arrays of Single-Walled Carbon Nanotubes ni Thin Film Type Transistors," Nano Lett. 7(5):1195-1202.
Kocabas et al. (Feb. 5, 2008) "Radio Frequency Analog Electronics Based on Carbon Nanotube Transistors," *Proc. Natl. Acad. Sci. USA* 105(5):1405-1409.
Kodambaka et al. (2006) "Control of Si Nanowire Growth by Oxygen," *Nano Lett.* 6(6):1292-1296.
Koide et al. (2000) "Patterned Luminescence of Organic Light-Emitting Diodes by Hot Microcontact Printing (H1JCP) of Self-Assembled Monolayers," *J. Am. Chem. Soc.* 122:11266-11267.
Konagai et al. (1978) "High Efficiency GaAs Thin Film Solar Cells by Peeled Film Technology," *J. Cryst. Growth* 45:277-280.
Kong et al. (2004) "Single-Crystal Nanorings Formed by Epitaxial Self-Coiling of Polar Nanobelts," *Science* 303: 1348-1351.
Kong et al. (Jan. 28, 2000) "Nanotube Molecular Wires as Chemical Sensors," *Science* 287:622-625.
Kong et al. (Oct. 2003) "Structure of Indium Oxide Nanobelts," *Solid State Commun.* 128(1):1-4.
Kong et al. (Oct. 29, 1998) "Synthesis of Individual Single-Walled Carbon Nanotubes on Patterned Silicon Wafers," *Nature* 395:878-881.

Kudo et al. (Web Release Jun. 13, 2006) "A Flexible and Wearable Glucose Sensor Based on Functional Polymers with Soft-MEMS Techniques," *Biosens. Bioelectron.* 22:558-562.
Kulkarni et al. (2002) "Mesoscale Organization of Metal Nanocrystals," *Pure Appl. Chem* 74(9):1581-1591.
Kumar et al. (1993) "Features of Gold Having Micrometer to Centimeter Dimensions can be Formed Through a Combination of Stamping with an Elastomeric Stamp and an Alkanethiol "Ink" Followed by Chemical Etching," *Appl. Phys. Lett.* 63(14):2002-2004.
Kumar et al. (1994) "Patterning Self-Assembled Monolavers: Applications in Material Science," *Langmuir* 10:1498-1511.
Kumar et al. (2002) "Thermally-Stable Low-Resistance Ti/Al/Mo/Au Multilayer Ohmic Contacts on n-GaN," *J. Appl. Phys.* 92:1712-1714.
Kumar et al. (2005) "Percolating in Finite Nanotube Networks," Phys. Rev. Lett., 95, 066802.
Kuo et al. (1985) "Effect of Mismatch Strain on Band Gap in III-V Semiconductors," *J. Appl. Phys.* 57:5428-5432.
Kuykendall et al. (Aug. 2004) "Crystallographic Alignment of High Density Gallium Nitride Nanowire Arrays," *Nat. Mater.* 3:524-528.
Lacour et al. (2003) "Stretchable Gold Conductors on Elastomeric Substrates," *Appl. Phys. Lett.* 82(15):2404-2406.
Lacour et al. (2005) "Stretchable Interconnects for Elastic Electronic Surfaces," *Proc.IEEE* 93(8):1459-1467.
Lacour et al. (2010) "Flexible and Stretchable Micro-Electrodes for in Vitro and n Vivo Neural Interfaces," Med. Biol. Eng. Comput. 48:945-954.
Lacour et al. (Apr. 2004) "Design and Performance of Thin Metal Film Interconnects for Skin-Like Electronic Circuits," *IEEE Electron. Dev. Lett.* 25(4):179-181.
Lacour et al. (Dec. 2004) "An Elastically Stretchable TFT Circuit," *IEEE Electron Dev. Lett.* 25(12):792-794.
Lacour et al. (Web Release Jul. 14,2006) "Stiff Subcircuit Islands of Diamondlike Carbon for Stretchable Electronics," *J. Appl. Phys.* 100:014913.
Lacour et al. (Web Release May 16, 2006) "Mechanisms of Reversible Stretchability of Thin Metal Films on Elastomeric Substrates," *Appl. Phys. Lett.* 88:204103.
Laimer et al. (Mar. 1997) "Diamond Growth in a Direct-Current Low-Pressure Supersonic Plasmajet," *Diamond Relat. Mater.* 6:406-410.
Lambacher et al. (2004) "Electrical Imaging of Neuronal Activity by Multi-Transistor-Array (MTA) Recording at 7.8 μm Resolution," *Appl. Phys. A* 79:1607-1611.
Landes et al. (2002) "Some Properties of Spherical and Rod-Shaped Semiconductorand Metal Nanocrystals," *Pure Appl. Chem.* 74(9):1675-1692.
Law et al. (2004) "Semiconductor Nanowires and Nanotubes," *Ann. Rev. Mater. Res.*34:83-122.
Law et al. (Aug. 27, 2004) "Nanoribbon Waveguides for Subwavelength PhotonicsIntegration," *Science* 305:1269-1273.
Lawrence et al. (2008) "Bioactive Silk Protein Biomaterial Systems for Optical Devices," Biomacromolecules 9:1214-1220.
Lay et al. (2004) "Simple Route to Large-Scale Ordered Arrays of Liquid-Deposited Carbon Nanotubes," Nano Lett., vol. 4, No. 4, pp. 603-606.
Leclercq et al. (1998) "II I-V Micromachined Devices for Microsystems," *Microelectronics J.* 29:613-619.
Lecomte et al. (Apr. 2006) "Degradation Mechanism of Diethylene Glycol Units in aTerephthalate Polymer," *Polym. Degrade. Stab.* 91(4):681-689.
Lee et al. (2000) "Thin Film Transistors for Displays on Plastic Substrates," *Solid State Electron.* 44:1431-1434.
Lee et al. (2003) "High-Performance Poly-Si TFTs on Plastic Substrates Using a Nano-Structured Separation Layer Approach," *IEEE Elec. Dev. Lett.* 24: 19-21.
Lee et al. (2004)"Organic Light-Emitting Diodes Formed by Soft Contact Lamination," *Proc. Natl. Acad. Sci. USA* 101(2):429-433.
Lee et al. (2005) "A Printable Form of Single-Crystalline Gallium Nitride for Flexable Optoelectronic Systems," *Small* 1:1164-1168.

(56) References Cited

OTHER PUBLICATIONS

Lee et al. (2005) "Large-Area, Selective Transfer of Microstructured Silicon (μs-Si): A Printing-Based Approach to High-Performance Thin-Film Transistors Supported on Flexible Substraights," *Adv. Mater.* 17:2332-2336.

Lee et al. (2006) "Micron and Submicron Patterning of Polydimethylsiloxane Resists on Electronics Materials by Decal Transfer Lithography and Reactive Ion-Beam Etching: Application to the Fabrication of High-Mobility, Thin-Film Transistors," Journal of Applied Physics 100. 0894907 (2006).

Lee et al. (Apr. 2005) "Fabrication of Stable Metallic Patterns Embedded in Poly(dimethylsiloxane) and Model Applications in Non-Planar Electronic and Lab-on-a-Chip Device Patterning," *Adv. Funct. Mater.* 15(4):557-566.

Lee et al. (Dec. 1999) "The Surface/Bulk Micromachining (SBM) Process: A New Method for Fabricating Released MEMS in Single Crystal Silicon," *J. Microelectromech. Syst.* 8(4):409-416.

Lee et al. (Feb. 2001) "Application of Carbon Nanotubes to Field Emission Displays," *Diamond and Related Mater.* 10(2):265-270.

Lee et al. (Feb. 2005) "Weave Patterned Organic Transistors on Fiber for E-Textiles," *IEEE Trans. Electron. Dev.* 52(2):269-275.

Leong et al. (2009) "Tetherless Thermobiochemicall Actuated Microgrippers," Proc. Natl. Acad. Sci. USA 106:703-709.

Létant et al. (Jun. 2003) "Functionalized Silicon Membranes for Selective Bio-Organisms Capture," Nat. Mater. 2:391-395.

Li et al. (2002) "High-Resolution Contact Printing with Dendrimers," Nano Lett. 2(4):347-349.

Li et al. (2003) "Ultrathin Single-Crystalline-Silicon Cantilever Resonators: Fabrication Technology and Significant Specimen Size Effect on Young's Modulus," *Appl. Phys. Lett.* 83:3081-3083.

Li et al. (2004) "Electrospinning of Nanofibers: Reinventing the Wheel," *Adv. Mater.* 16(14):1151-1170.

Li et al. (2006) "Catalyst-Assisted Formation of Nanocantilever Arrays on ZnS Nanoribbons by Post-Annealing Treatment," J. Phys. Chem. B 110(13):6759-6762.

Li et al. (Dec. 2005) "Compliant Thin Film Patterns of Stiff Materials as Platforms for Stretchable Electronics," *J. Mater. Res.* 20(12):3274-3277.

Li et al. (Jul. 1, 2002) "ZnO Nanobelts Grown on Si Substrate," *Appl. Phys. Lett.* 81 (1): 144-146.

Li et al. (Web Release Mar. 16, 2006) "Catalyst-Assisted Formation of Nanocantilever Arrays on ZnS Nanoribbons by Post-Annealing Treatment," *J. Phys. Chem.* 8 110(13):6759-6762.

Lieber, C. (2001) "The Incredible Shrinking Circuit," *Sci. Am.* 285(3)58-64.

Lieber, C.M. (2003) "Nanoscale Science and Technology: Building a Bog Future from Small Things," *MRS. 8ull.* 28:486-491.

Lim et al. (2005) "Flexible Membrane Pressure Sensor," *Sens. Act. A* 119:332-335.

Lima et al. (2007) "Creating Micro- and Nanostructures on Tubular and Spherical Surfaces,"J. Vac. Sci. Technol. 825(6):2412-2418.

Lin et al. (2005) "High-Performance Carbon Nanotube Field-Effect Transistor with Tunable Polarities," *IEEE Trans. Nano* 4(5):481-489.

Linder et al. (1994) "Fabrication Technology for Wafer Through-Hole Interconnections and Three-Dimensional Stacks of Chips and Wafers," *Proc. IEEE Micro. Electro Mech. Syst.* 349-354.

Ling et al. (2004) "Thin Film Deposition, Patterning, and Printing in Organic Thin Film Transistors," *Chem. Mater.* 16:4824-4840.

Liu et al. (1999) "Controlled deposition of individual single-walled carbon nanotubes on chemically functionalized templates," Chem. Phys. Lett., 303:125-129.

Long et al. (1990) "Heterostructure FETs and Bipolar Transistors," in; *Gallium Arsenide Digital Integrated Circuit Design*, McGraw-Hill, New York, pp. 58-69.

Loo et al. (2002) "Additive, Nanoscale Patterning of Metal Films with a Stamp and a Surface Chemistry Mediated Transfer Process: Applications in Plastic Electronics,"*Appl. Physics Lett.* 81 :562-564.

Loo et al. (2002) "High-Resolution Transfer Printing on GaAs Surfaces Using Alkane Dithiol Monolayers," *J. Vac. Sci. Technol.* B 20(6):2853-2856.

Loo et al. (2002) "Interfacial Chemistries for Nanoscale Transfer Printing," *J. Am. Chem. Soc.* 124:7654-7655.

Loo et al. (2002) "Soft, Conformable Electrical Contacts for Organic Semiconductors: High-Resolution Plastic Circuits by Lamination," *Proc. Natl. Acad. Sci. USA* 99(16): 10252-1 0256.

Loo et al. (2003) "Electrical Contacts to Molecular Layers by Nanotransfer Printing," *Nano Lett.* 3(7):913-917.

Lopes et al. (Sep. 2004) "Thermal Conductivity of PET/(LDPE/AI) Composites Determined by MDSC," *Polym. Test.*23(6):637-643.

Lu et al. (Apr. 2010) "Water-Insoluble Silk Films with Silk I Structure," Acta Biomater. 6(4):1380-1387.

Lu et al. (Dec. 2006) "Electronic Materials-Buckling Down for Flexible Electronics," *Nat. Nanotechnol.* 1: 163-164.

Lu et al. (Jul. 19,2005) "One Dimensional Hole Gas in Germanium/Silicon Nanowire Heterostructures," *Proc. Nat. Acad. Sci. USA* 102(29):10046-10051.

Lu et al. (Nov. 2008) "Nanowire Transistor Performance Limits and Applications," *IEEE Trans Electron Dev*. 55(11 ):2859-2876.

Luan et al. (1992) "An Experimental Study of the Source/Drain Parasitic Resistance Effects in Amorphous Silicon Thin Film Transistors," *J. Appl. Phys.* 72:766-772.

Ma et al. (2004) "Single-Crystal CdSe Nanosaws," *J. Am. Chem. Soc.* 126(3):708-709.

Mack et al. (2006) "Mechanically Flexible Thin-Film Transistors that Use Ultrathin Ribbons of Silicon Derived from Bulk Wafers," *Appl. Phys. Lett.* 88:213101.

Madou, M. (1997) "Etch-Stop Techniques," In; *Fundamentals of Microfabrication*, CRC Press, New York, pp. 193-199.

Maikap et al. (2004) "Mechanically Strained-Si NMOSFETs," *IEEE Electron. Dev. Lett*. 25:40-42.

Maldovan et al. (2004) "Diamond-Structured Photonic Crystals," *Nature Materials* 3:593-600.

Mandlik et al. (Aug. 2006) "Fully Elastic Interconnects on Nanopatterned Elastomeric Substrates," *IEEE Electron Dev. Lett.* 27(8):650-652.

Manna et al. (Web Release May 25, 2003) "Controlled Growth of Tetrapod-Branched Inorganic Nanocrystals," *Nat. Mater.* 2:382-385.

Markovich et al. (1999) "Architectonic Quantum Dot Solids," *Ace. Chem. Res.* 32:415-423.

Marquette et al. (2004) "Conducting Elastomer Surface Texturing: A Path to Electrode Spotting Application to the Biochip Production," *Biosens. Bioelectron.* 20:197-203.

Martensson et al. (2004) "Nanowire Arrays Defined by Nanoimprint Lithography," *Nano Lett.* 4:699-702.

Martin, C.R. (1995) "Template Synthesis of Electronically Conductive Polymer Nanostructures," *Ace. Chem. Res.* 28:61-68.

Mas-Torrent et al. (2006) "Large Photoresponsivity in High-Mobility Single-Crystal Organic Field-Effect Phototransistors," *ChemPhysChem* 7:86-88.

Masuda et al. (2000) "Fabrication of Ordered Diamonds/Metal Nanocomposite Structures," *Chern. Lett.* 10:1112-1113.

Matsunaga et al. (2003) "An Improved GaAs Device Model for the Simulation of Analog Integrated Circuit," *IEEE Trans. Elect. Dev.* 50:1194-1199.

McAlpine et al. (2003) "High-Performance Nanowire Electronics and Photonics on Glass and Plastic Substrates," *Nano Lett*. 3:1531-1535.

McAlpine et al. (2005) "High-Performance Nanowire Electronics and Photonics and Nanoscale Patterning on Flexible Plastic Substrates," *Proc. IEEE* 93:1357-1363.

McCaldin et al. (1971) "Diffusivity and Solubility of Si in the Al Metallization of Integrated Circuits," *Appl. Phys. Lett.* 19:524-527.

Mehring C. et al. (2003) Inference of hand movements from local field potentials in monkey motor cortex. Nature Neurosci. 6, 1253-1254.

Meisel et al. (2004) "Three-Dimensional Photonic Crystals by Holographic Lithography Using the Umbrella Configuration: Symmetries and Complete Photonic Band Gaps," *Phys. Rev.* B. 70:165101:1-10.

Meitl et al. (2004) "Solution Casting and Transfer Printing Single-Walled Carbon Nanotube Films," *Nano Lett.* 4(9):1643-1947.

Meitl et al. (2006) "Transfer Printing by Kinetic Control of Adhesion to an Elastomeric Stamp," *Nat. Mater.* 5:33-38.

(56) References Cited

OTHER PUBLICATIONS

Meitl et al. (Web Release Feb. 22, 2007) "Stress Focusing for Controlled Fracture in Microelectromechanical Systems," Appl. Phys. Lett. 90:083110.
Melosh et al. (2003) "Ultrahigh-Density Nanowire Lattices and Circuits," *Science* 300:112-115.
Menard et al. (2004) "A Printable Form of Silicon for High Performance Thin Film Transistors on Plastic Substrates," Appl. Phys. Lett. 84:5398-5400.
Menard et al. (2004) "High-Performance n- and p-Type Single-Crystal Organic Transistors with Free-Space Gate Dielectrics," Adv. Mat. 16:2097-2101.
Menard et al. (2004) "Improved Surface Chemistries, Thin Film Deposition Techniques, and Stamp Designs for Nanotransfer Printing," Langmuir 20:6871-6878.
Menard et al. (2005) Bendable Single Crystal Silicon Thin Film Transistors Formed by Printing on Plastic Substrates Appl. Phys. Lett. 86:093507.
Menard et al. (2007) Micro- and Nanopatterning Techniques for Organic Electronic and Optoelectronic Systems, Chem. Rev. 107:1117-1160.
Miao et al. (2003) "Micromachining of Three-Dimensional GaAs Membrane Structures Using High-Energy Nitrogen Implantation," J. Micromech. Microenq. 13:35-39.
Michalske et al. (1985) "Closure and Repropagation of Healed Cracks in Silicate Glass," J. Am. Ceram. Soc. 68:586-590.
Michel et al. (2001) Printing Meets Lithography: Soft Approaches to High-Resolution Patterning, IBM J. Res. Dev. 45(5):697-719.
Miller et al. (2002) "Direct Printing of Polymer Microstructures on Flat and Spherical Surfaces Using a Letterpress Technique," J. Vac. Sci. Technol. B 20(6):2320-2327.
Milliron et al. (2004) "Colloidal Nanocrystal Heterostructures with Linear and Branched Topoloqy," Nature 430:190-195.
Min, G. (Apr. 4, 2003) "Plastic Electronics and Their Packaging Technologies," *Syn. Metals.* 135:141-143.
Minev et al. (2010) "Impedance Spectroscopy on Stretchable Microelectrode Arrays," Appl. Phys. Lett. 97:043707.
Mirkin et al. (Jul. 2001) "Emerging Methods for Micro—and Nanofabrication," *MRS Bull.* 26(7):506-507.
Misewich et al. (May 2,2003) "Electronically Induced Optical Emission from a Carbon Nanotube FET," Science 300:783-786.
Mishra et al. (2002) "AlGaN/GaN HEMTs—an Overview of Device Operation and Applications," Proc. IEEE 90:1022-1031.
Mitzi et al. (2004) "High-Mobility Ulltrathin Semiconducting Films Prepared by Spin Coating," Nature 428:229-303.
Moon et al. (2002) "Ink-Jet Printing of Binders for Ceramic Compinents," *J. Am. Ceram. Soc.* 85(4):755-762.
Moore et al. (Sep. 9, 2003) "Individually Suspended Single-Walled Carbon Nanotubes in Various Surfacants," Nano Lett. 3(10):1379-1382.
Morales et al. (Jan. 9, 1998) "A Laser Ablation Method for the Synthesis of Crystalline Semiconductor Nanowires," Science 279:208-211.
Morent et al. (2007) "Adhesion Enhancement by a Dielectric Barrier Discharge of PDMS used for Flexible and Stretchable Electronics," J. Phys. D. Appl. Phys. 40:7392-7401.
Mori et al. (1978) "A New Etching Solution System, H3P04-H202-H20, for GaAs and Its Kinetics," J. Electrochem. Soc. 125:1510-1514.
Morkoc et al. (1995) "High-Luminosity Blue and Blue-Green Gallium Nitride Light-Emitting Diodes," Science 267:51-55.
Morkved et al. (1994) "Mesoscopic Self-Assembly of Gold Islands on Diblock-Copolymer Films," Appl. Phys. Lett. 64:422-424.
Morra et al. (1990) "On the Aging of Oxygen Plasma-Treated Polydimethylsiloxane Surfaces," J. Colloid Interface Sci. 137:11-24.
Murakami et al. (2005) "Polarization Dependence of the Optical Absorption of Single-Walled Carbon Nanotubes," Phys. Rev. Lett., 94, 087402.
Murphy et al. (2008) "Modification of Silk Fibroin Using Diazonium Coupling Chemistry and the Effects on hMSC Proliferation and Differentiation," Biomaterials 29:2829-2838.
Namazu et al. (2000) "Evaluation of Size Effect on Mechanical Properties of Single Crystal Silicon by Nanoscale Bending Test Using AFM," J. MEMS 9:450-459.
Nath et al. (2002) "Nanotubes of the Disulfides of Groups 4 and 5 Metals," *Pure Appl. Chem.* 74(9):1545-1552.
Nathan et al. (2000) "Amorphous Silicon Detector and Thin Film Transistor Technology for Large-Area Imaging of X-Rays,." Microelectron J. 31 :883-891.
Nathan et al. (2002) "Amorphous Silicon Technology for Large Area Digital X-Ray and Optical Imaging," Microelectronics Reliability 42:735-746.
Newman et al. (2004) "Introduction to Organic Thin Film Transistors and Design of n-Channel Organic Semiconductors," Chem. Mater. 16:4436-4451.
Nirmal et al. (1999) "Luminescence Photophysics in Semiconductor Nanocrystals," Ace. Chem. Res. 32:407-414.
Noda et al. (1996) "New Realization Method for Three-Dimensional Photonic Crystal in Optical Wavelength Region," Jpn. J. Appl. Phys. 35:L909-L912.
Nomura et al. (2004) "Room-Temperature Fabrication of Transparent Flexible Thin-Film Transistors Using Oxide Semiconductors," Nature 432:488-492.
Notice of Allowance, Corresponding to U.S. Appl. No. 11/423,287, Mailed Jan. 12, 2009.
Notice of Allowance, Corresponding to U.S. Appl. No. 12/723,475, mailed on Oct. 14, 2011.
Notice of Allowance, U.S. Appl. No. 11/851,182, mailed Feb. 16, 2012.
Notice of Allowance, U.S. Appl. No. 12/405,475, mailed Mar. 1, 2012.
Notification Concerning Transmittal of International Preliminary Report on Patentability, Corresponding to International Application No. PCT/US2009/059892, mailed Jan. 7, 2011.
Notification Concerning Transmittal of International Preliminary Report on Patentability, Corresponding to International Application No. PCT/US2009/064199, mailed May 17, 2011.
Novoselov et al. (Oct. 22, 2004) "Electric Field Effect in Atomically Thin Carbon Films," Science 306:666-669.
O'Riordan et al. (2004) "Field Configured Assembly: Programmed Manipulation and Self-Assembly at the Mesoscale," Nano Lett. 4:761-765.
O'Connell et al. (Jul. 26, 2002) "Band Gap Fluorescence from Individual Single-Walled Caarbon Nanotubes," Science 297:593-596.
Odom et al. (2002) "Improved Pattern Transfer in Soft Lithography Using Compasite Stamps," Langmuir 18:5314-5320.
Office Action and Response, Corresponding to Malaysian Patent Publication No. PI 20052553, Mailed Mar. 13, 2009 and Dec. 8, 2009.
Office Action and Response, Corresponding to U.S. Appl. No. 11/423,287, Mailed Feb. 13, 2008.
Office Action and Response, Corresponding to U.S. Appl. No. 11/421,654, Mailed Sep. 29, 2009.
Office Action and Response, Corresponding to U.S. Appl. No. 11/858,788, Mailed Beginning Jan. 28, 2011.
Office Action Corresponding to Chinese Patent Application No. 200780041127.6, issued Apr. 8, 2011.
Office Action Corresponding to Chinese Patent Application No. 200780049982.1, Issued May 12, 2010.
Office Action Corresponding to European Patent Application No. 05755193.9, issued Jul. 12, 2011.
Office Action, Corresponding to Chinese Paten Application No. 200580013574.1, Issued May 11, 2010.
Office Action, Corresponding to Taiwan Patent Application No. 095121212, Issued May 7, 2010.
Office Action, Corresponding to U.S. Appl. No. 11/423,287, Mailed Feb. 13, 2008.
Office Action, Corresponding to U.S. Appl. No. 11/851,182, Mailed Apr. 1,2010.
Office Action, Corresponding to U.S. Appl. No. 11/851,182, Mailed Jun. 7,2011.

(56) References Cited

OTHER PUBLICATIONS

Office Action, Corresponding to U.S. Appl. No. 11/421,654, Mailed Sep. 23, 2010.
Office Action, Corresponding to U.S. Appl. No. 11/981,380, Mailed Sep. 23, 2010.
Office Actions, Corresponding to Chinese Patent Application No. 200580018159.5, Issued Jan. 23, 2009 and Feb. 12, 2010.
Office Actions, Corresponding to U.S. Appl. No. 11/145,542, Mailed between Apr. 5, 2007 and Dec. 23, 2008.
Office Action, Corresponding to U.S. Appl. No. 12/636,071, mailed Jun. 6, 2012.
Ohzono et al. (Web Release Jul. 7, 2005) "Geometry-Dependent Stripe Rearrangement Processes Induced by Strain on Preordered Microwrinkle Patterns," Langmuir 21(16):7230-7237.
Omenetto et al. (2008) "A New Route for Silk," Nature Photon. 2:641-643.
Ong et al. (2004) "High-Performance Semiconducting Poolythiophenes for Organic Thin-Film Transistors," J. Am. Chem. Soc. 126:3378-3379.
Ong et al. (2005) "Design of High-Performance Regioreular Polythiophenes for Organic Thin-Film Transistors," Proc. IEEE 93:1412-1419.
Origin Energy (May 2004) "Fact Sheet—Sliver Cells," www.oriqinenergY.com.au/sliver Ouyang et al. (2002) "High-Performance, Flexible Polymer Light-Emitting Diodes Fabricated by a Continuous Polymer Coating Process," Adv. Mat. 14:915-918.
Ouyang et al. (2002) "High-Performance, Flexible Polymer Light-Emitting Diodes Fabricated By a Continuous Polymer Coating Process," Adv. Mat. 14:915-918.
Ouyang et al. (2008) "High Frequency Properties of Electro-Textiles for Wearable Antenna Applications," IEEE Trans. Antennas Propaq. 56(2):381-389.
Ouyang et al. (Web Release Mar. 20, 2000) "Conversion of Some Siloxane Polymers to Silicon Oxide by UV/Ozone Photochemical Processes," Chem. Mater. 12(6): 1591-1596.
Overholt et al. (2005) "Photodynamic Therapy for Esophageal Cancer using a 180° Windowed Esophageal Balloon," Lasers in Surg. Med. 14:27-33.
Pan et al. (2001) "Nanobelts of Semiconducting Oxides," Science 291: 1947-1949.
Panev et al. (2003) "Sharp Exciton Emission from Single InAs Quantum Dots in GaAs Nanowires," Appl. Phys. Lett. 83:2238-2240.
Pardo et al. (2000) "Application of Screen Printing in the Fabrication of Organic Ligh-Emitting Devices," Adv. Mater. 12(17):1249-1252.
Park et al. (1997) "Block Copolymer Lithography: Periodic Arrays of -10 Holes in 1 Square Centimeter," Science 276:1401-1404.
Park et al. (1998) "Fabrication of Three-Dimensional Macroporous Membranes with Assemblies of Microspheres as Templates," Chem. Mater. 10:1745-1747.
Park et al. (Aug. 2009) "Printed Assemblies of Inorganic Light-Emitting Diodes for Deformable And Semitransparent Displays," Science 325:977-981.
Park et al. (Web Release Feb. 22, 2009) "Biodegradable Luminescent Porous Silicon Nanoparticles for in Vivo Applications," Nature Mater. 8:331-336.
Parker et al. (2009) "Biocompatible Silk Printed Optical Waveguides," Adv. Mater. 21:2411-2415.
Patolsky et al. (2006) "Detection, Stimulation, and Inhibition of Neuronal Signals with High-Density Nanowire Transistor Arrays," Science 313:1100-1104.
Patton et al. (Mar. 1998) "Effect of Diamond like Carbon Coating and Surface Topography on the Performance of Metal Evaporated Magnetic Tapes," IEEE Trans Magn. 34(2):575-587.
Paul et al. (Apr. 2003) "Patterning Spherical Surfaces at the Two Hundred Nanometer Scale Using Soft Lithography," Adv. Func. Mater. 13(4):259-263.
Pearton et al. (1999) "GaN: Processing, Defects, and Devices," J. Appl. Phys. 86:1-78.
Peng et al. (Mar. 2, 2000) "Shape Control of CdSe Nanocrystals," Nature 404:59-61.

Perry et al. (2008) "Nano—and Micropatterning of Optically Transparent, Mechanically Robust, Biocompatible Silk Fibroin Films," Adv. Mater. 20:3070-3072.
Piazza et al. (2005) "Protective Diamond-Like Carbon Coatings for Future Optical Storage Disks," Diamond Relat. Mater. 14:994-999.
Pimparkar et al. (Feb. 2007) "Current-Voltage Characteristics of Long-Channel Nanobundle Thin-Film Transistors: A 'Bottom-Up' Perspective," IEEE Electron Dev. Lett. 28(2):157-160.
Podzorov et al. (2005) "Hall Effect in the Accumulation Layers on the Surface of Orgaic Semiconductors," Phys. Rev. lett. 95:226601.
Pushpa et al. (2002) "Stars and Stripes. Nanoscale Misfit Dislocation Patterns on Surfaces," Pure Appl. Chem. 74(9):1663-1671.
Qian et al. (2006) "Scaling Effects of Wet Adhesion in Biological Attachment Systems," Acta Biomaterialia 2:51-58.
Quake et al (2000) "From Micro- to Nanofabrication with Soft Materials," Science 290: 1536-1540.
Radtke et al. (Feb. 5, 2007) "Laser-Lithography on Non-Planar Surfaces," Opt. Exp. 15(3):1167-1174.
Raman et al. (1989) "Study of Mesa Undercuts Produced in GaAs with $H_3PO_4$-Based Etchants," J. Electrochem. Soc. 136:2405-2410.
Randall et al. (2005) "Permeation-driven flow in poly(dimethylsiloxane) microfluidic devices," Proc. Nat. Acad. Sci. USA 102(31):10813-10818.
Rao et al. (2003) "Large-scale assembly of carbon nanotubes," Nature, 425:36-37.
Razavi et al. (2009) "Three Dimensional Nanopillar Array Photovoltaics on Low Cost and Flexible Substrates," Nature Materials 8:648-653.
Razeghi et al. (1994) "High-Power Laser Diodes Based on InGaAsP Alloys," Nature 369:631-633.
Razouk et al. (Sep. 1979) "Dependence of Interface State Density on Silicon Thermal Oxidation Process Variables," J. Electrochern. Soc. 126(9):1573-1581.
Reuss et al. (2005) "Microelectronics: Perspectives on Technology and Applications," Proc. IEEE 93:1239-1256.
Reuss et al. (Jun. 2006) "Microelectronics," MRS Bull. 31 :447-454.
Ribas et al. (1998) "Bulk Micromachining Characterization of 0.2 μm HEMT MMIC Technology for GaAs MEMS Design," Mater. Sci. Eng. B 51 :267-273.
Ridley et al. (1999) "All-Inorganic Field Effect Transistors Fabricated by Printing," Science 286:746-749.
Roberts et al. (1979) "Looking at Rubber Adhesion," Rubber Chem. Technol. 52:23-42.
Roberts et al. (May 2006) "Elastically Relaxed Free-Standing Strained-Silicon Nanomembranes," Nat. Mater. 5:388-393.
Robinson et al. (1983) "GaAs Readied for High-Speed Microcircuits," Science 219:275-277.
Roelkens et al. (Dec. 2005) "Integration of InP/InGaAsP Photodetectors onto Siliconon-Insulator Waveguide Circuits," Optics Express 13(25):10102-10108.
Rogers et al. (1997) "Using an Elastomeric Phase Mask for Sub-100 nm Photolithography in the Optical Near Field," Appl. Phys. Lett. 70:2658-2660.
Rogers et al. (1998) "Generating ~90 Nanometer Features Using Near Field Contact Mode Photolithography with an Elastomeric Phase Mask," J. Vac. Sci. Technol. 16(1 ):59-68.
Rogers et al. (1998) "Quantifying Distortions in Soft Lithography," J. Vac. Sci. Technol. 16:88-97.
Rogers et al. (1998) "Using Printing and Molding Techniques to Produce Distributed Feedback and Bragg Reflector Resonators for Plastic Lasers," Appl. Phys. Lett. 73: 1766-1768.
Rogers et al. (1999) Printing Process Suitable for Reel-to-Reel Production of High-Performance Organic Transistors and Circuits, Adv. Mater. 11 (9):741-745.
Rogers et al. (2000) "Organic Smart Pixels and Complementart Inverter Circuits Formed on Plastic Substrates by Casting and Rubber Stamping," IEEE Electron Dev. Lett. 21 (3): 100-103.
Rogers et al. (2001) "Paper-Like Electronic Displays: Large-Area Rubber-Stamped Plastic Sheets of Electronics and Microencapsulated Electrophoretic Inks," Proc. Nat/Acad. Sci. USA 98:4835-4840.
Rogers et al. (2002) "Printed Plastic Electronics and Paperlike Displays," J. Polym. Sci. Part A. Polym. Chem. 40:3327-3334.

(56) References Cited

OTHER PUBLICATIONS

Rogers, J. (Jul. 9, 2010) "Farewell to Flatland," Science 329:138139.
Rogers, JA (2001) "Rubber Stamping for Plastic Electronics and Fiber Optics," MRS Bulletin 26(7):530-534.
Rogers, JA (2001) "Toward Paperlike Displays," Science 291: 1502-1503.
Rosenblatt et al. (2002) "High Performance Electrolyte Gated Carbon Nanotube Transistors,"Nano Lett. 2(8):869-872.
Rotkin et al. (2003) "Universal Description of Channel Conductivity for Nanotube and Nanowire Transistors," Appl. Phys. Lett. 83:1623-1625.
Roundy et al. (2003) "Photonic Crystal Structure with Square Symetry within EachLayer and a Three-Dimensional Band Gap," Appl. Phys Lett. 82:3835-3837.
Rubehn et al. (2009) "A MEMS based Flexible Multichannel ECoG-Electrode Array," J. Neural Eng. 6:036003.
Ruchehoeft et al. (2000) "Optimal Strategy for Controlling Linewidth on Spherical Focal Surface Arrays," J. Vac. Sci. Technol. B 18(6):3185-3189.
Ryu et al. (2009) "Human Cortical Prostheses: Lost in Translation?" Neurosurg Focus 27(1):E5.
Samuelson et al. (2004) "Semiconductor Nanowires for Novel One-Dimensional Devices," Physica E 21 :560-567.
Sangwal et al. (1997) "Nature of multilayer steps on the {100} cleavage planes of MgO single crystals," Surf. Sci., 383:78-87.
Santin et al. (1999) "In vitro Evaluation of the Inflammatory Potential of the Silk Fibroin," J. Biomed. Mater. Res. 46:382-389.
Sanyal et al. (2002) "Morphology of Nanostructures Materials," Pure Appl. Chem. 74(9): 1553-1570.
Sazonov et al. (2005) "Low-Temperature Materials and Thin-Film Transistors for Flexible Electronics," Proc. IEEE 93:1420-1428.
Scherlag et al. (1969) "Catheter Technique for Recording His Bundle Activity in Man," Circulation 39:13-18.
Schermer et al. (2005) "Thin-Film GaAs Epitaxial Lift-Off Solar Cells for Space Applications," Prog. Photovolt. Res. Appl. 13:587-596.
Schermer et al. (2006) "Photon Confinement in High-Efficiency, Thin Film II I-V Solar Cells Obtained by Epitaxial Lift-Off," Thin Solid Films 211-512:645-653.
Schindl et al. (2003) "Direct Stimulatory Effect of Low-Intensity 670-nm Laser Irradiation on Human Endothelial Cell Proliferation," Br. J. Dermatol. 148:334-336.
Schlegel et al. (2002) "Structures of quartz (1010)- and (1011)-water interfaces determined by X-ray reflectivity and atomic force microscopy of natural growth surfaces," Geochim. Cosmochim. Acta, vol. 66, No. 17, pp. 3037-3054.
Schmid et al. (2003) "Preparation of Metallic Films on Elastomeric Stamps and Their Application for Contact Processing and Contact Printing," Adv. Funct. Mater. 13:145-153.
Schmid et al. (Mar. 25, 2000) "Siloxane Polymers for High-Resolution, High-Accuracy Soft Lithography," Macromolecules 33(8):3042-3049.
Schmid et al. (May 11, 1998) "Light- Coupling Masks for Lensless, Sub-wavelength Optical Lithography," Appl. Phys. Lett. 72(19):2379-2381.
Schmidt et al. (Mar. 8, 2001) "Thin Solid Films Roll up into Nanotubes," Nature 410:168.
Schnable et al. (1969) "Aluminum Metallization; Advantages and Limitations for Integrated Circuit Applications," IEEE 57: 1570-1580.
Schneider et al. (2008) "Mechanical Properties of Silicones for MEMS," J. Micromech. Microeng. 18:065008.
Schon et al. (1995) "Ambipolar Pentacene Field-Effect Transistors and Inverters," Science 287: 1022-1 023.
Schrieber et al. (1998) "The Effectiveness of Silane Adhesion Promotors in the Performance of Polyurethane Adhesives," J. Adhesion 68:31-44.
Scorzoni et al. (Oct. 4, 2004) "On the Relationship Between the Temperature coefficient of Resistance and the Thermal Conductance of Integrated Metal Resistors," Sens Actuators A 116(1): 137-144.

Search and Examination Report, Corresponding to Singapore Patent Application No. 200607372-0, Mailed Oct. 17, 2007.
Search Report and Examination Report Corresponding to Singapore Patent Application No. 200901178-4, completed Mar. 13, 2010.
Search Report Corresponding to Singapore Patent Application No. SG 200607372-0, Mailer Oct. 17, 2007.
Search Report Corresponding to Taiwanese Application No. 095121212, completed Oct. 8, 2010.
Search Report, Corresponding to Republic of China (Taiwan) Patent Application No. 094118507, Dated Feb. 24, 2007.
Seidel et al. (2004) "High-Current Nanotube Transistors," Nano Lett., vol. 4, No. 5, pp. 831-834.
Sekitani et al. (2005) "Bending Experimant on Pentacene Field-Effect Transistors on Plastic Films," Appl. Phys. Lett. 86:073511.
Sekitani et al. (2009) "Stretchable Active-Matrix Organic Light-Emitting Diode Display Using Printable Elastic Conductors," Nature Mater. 8:494-499.
Sekitani et al. (Sep. 12,2008) "A Rubberlike Stretchable Active Matrix Using Elastic Conductors," Science 321 :1468-1472.
Sen et al. (2002) "Nonequilibrium Processes for Generating Silicon Nanostructures in Single-Crystalline Silicon," Pure Appl. Chem. 74(9):1631-1641.
Serikawa et al. (May 1, 2000) "High-Mobility Poly-Si Thin Film Transistors Fabricated on Stainless-Steel Foils by Low-Temperature Processes Using Sputter-Depositions," Jpn. J. Appl. Phys. 39:L393-L395.
Servanti et al. (2005) "Functional Pixel Circuits for Elastic AMOLED displays," Prac. IEEE 93:1257-1264.
Service, R.F. (Aug. 15,2003) "Electronic Textiles Charge Ahead," Science 301 :909-911.
Shan et al. (2004) "From Si Source Gas Directly to Positioned, Electrically Contacted Si Nanowires: The Self-Assembling 'Grow-in-Place' Approach," Nano Lett. 4(11):2085-2089.
Sharp et al. (2003) "Holographic Photonic Crystals with Diamond Symmetry," Phys. Rev. B 68:205102/1-205102/6.
Sheraw et al. (2002) "Organic Thin-Film Transistor-Driven Polymer-Dispersed Liquid Crystal Displays on Flexible Polymeric Substrates," Appl. Phys. Lett. 80: 1088-1 090.
Shetty et al. (2005) "Formation and Characterization of Silicon Films on Flexible Polymer Substrates," Mater. Lett. 59:872-875.
Shi et al. (2001) "Free-Standing Single Crystal Silicon Nanoribbons," J. Am. Chem. Soc. 123(44):11095-11096.
Shi et al. (Sep. 2000) "Synthesis of Large Areas of Highly Oriented, Very Long Silicon Nanowires," Adv. Mater. 12(18):1343-1345.
Shi et al. (Web Release Oct. 11, 2001) "Free-Standing Single Crystal Silicon Nanoribbons," J. Am. Chem. Soc. 123(44):11095-11096.
Shin et al. (2003) "PDMS-Based Micro PCR Chip with Parylene Coating," J. Micromech. Microeng. 13:768-774.
Shtein et al. (Oct. 15, 2004) "Direct Mask-Free Patterning of Molecular Organic Semiconductors Using Organic Vapor Jet Printing," J. Appl. Phys. 96(8):4500-4507.
Shull et al. (1998) "Axisymmetric Adhesion Tests of Soft Materials," Macramol. Chem. Phys. 1999:489-511.
Siegel et al. (2009) "Thin, lightweight, Foldable Thermochromic Displays on Paper," Lab Chip 9:2775-2781.
Siegel et al. (2010) "Foldable Printed Circuit Boards on Paper Substrates," Adv. Funct. Mater. 20:28-35.
Siegel et al. (Web Release Feb. 7, 2007) "Microsolidics: Fabrication of Three-Dimensional Metallic Microstructure in Poly(dimethylsiloxane)," Adv. Mater. 19(5):727-733.
Sim et al. (1993) "An Analytical Back-Gate Bias Effect Model for Ultrathin SOI CMOS Devices," IEEE Trans. Elec. Dev. 40:755-765.
Sirringhaus et al. (2003) "Inkjet Printing of Functional Materials," MRS Bull. 28:802-806.
Sirringhaus et al. (Dec. 15, 2000) "High-Resolution Inkjet Printing of All-Polymer Transistor Circuits," Science 290:2123-2126.
Sirringhaus, H. (2005) "Device Physics of Solution-Processed Organic Field-Effect Transistors,"Adv. Mater. 17:2411-2425.
Smay et al. (2002) "Colloidal Inks for Directed Assembly of 3-D Periodic Structures," Langmuir 19:5429-5437.
Smith et al. (2000) "Electric-Field Assisted Assembly and Alignment of Metallic Nanowires," Appl. Phys. Lett. 77(9):1399-1401.

(56) References Cited

OTHER PUBLICATIONS

Snow et al. (2003) "Random networks of carbon nanotubes as an electronic material," Appl. Phys. Lett., vol. 82, No. 13, pp. 2145-2147.
Snow et al. (2005) "High-mobility carbon-nanotube transistors on a polymeric substrate," Appl. Phys. Lett., 86, 033105.
So et al. (2008) Organic Light-Emitting Devices for Solid-State Lighting, MRS Bull. 33:663-669.
Sofia et al. (2001) "Functionalized Silk-Based Biomaterials for Bone Formation," J. Biomed. Mater. Res. 54:139-148.
Someya et al. (2005) "Conformable, Flexible, Large-Area Networks of Pressure and Thermal Sensors with Organic Transistor Active Matrixes," Proc. Nat. Acad. Sci. USA 102:12321-12325.
Someya et al. (2005) "Integration of Organic FETs with Organic Photodiodes for a Large Area, Flexible, and Lightweight Sheet Image Scanners," IEEE Trans. Electron Devices 52:2502-2511.
Someya et al. (Jul. 6,2004) "A Large-Area, Flexible Pressure Sensor Matrix With Organic Field-Effect Transistors for Artificial Skin Applications," Proc. Nat. Acad. Sci. USA 101 (27):9966-9970.
Someya, T. (Aug. 7, 2008) "Electronic Eyeballs," Nature 454:703-704.
Soole et al. (Mar. 1991) "InGaAs Metal-Semiconductor-Metal Photodetectors for Long Wavelength Optical Communications," IEEE J. Quantum Electron. 27(3):737-752.
Soong et al. (1984) "Adverse Reactions to Virgin Silk Sutures in Cataract Surgery," Ophthalmology 91:479-483.
Srinivasan et al. (Web Release Mar. 26, 2007) "Piezoelectric/ Ultrananocrystalline Diamond Heterostructures for High-Performance Multifunctional Micro/Nanoelectromechanical Systems," Appl. Phys. Lett. 90: 1341 01.
Stafford et al. (2004) "A Buckling-Based Metrology for Measuring the Elastic Moduli of Polymeris Thin Films," Nature Mater. 3:545-550.
Star et al. (2004) "Nanotube Optoelectric Memory Devices," Nano Lett., vol. 4, No. 9, pp. 1587-1591.
Stella Newsletter IV, Stretchable Electronics for Large Area Applications [online: Apr. 29, 2011] http://www.stella-project.de/Portals/0/Stella_Newsletter_6.pdf.
Storm et al. (Web Release Jul. 13, 2003) "Fabrication of Solid-State Nanopores with Single-Nanometre Precision," Nat. Mater. 2:537-540.
Streetman et al. (2000) "Intrinsic Material," In; Solid State Electronic Devices, 5th Ed., Prentice Hall; Upper Saddle River, NJ; pp. 74-75.
Strukov et al. (2005) "CMOL FPGA: A Reconfigurable Architecture for Hybrid Digital Circuits with Two-Terminal Nanodevices," Nanotechnology 16:888-900.
Su et al. (2000) "Lattice-Oriented Growth of Single-Walled Carbon Nanotubes," J. Phys. Chem. B 104(28):6505-6508.
Sum et al. (2009) "Near-Infrared Spectroscopy for the Detection of Lipid Core Coronary Plaques," Curr. Cardiovasc. Imag. Rep. 2:307-315.
Sumant et al. (Apr. 2005) "Toward the Ultimate Tribological Interface: Surface Chemistry and Nanotribology of Ultrananocrystalline Diamond," Adv. Mater 17(8):1039-1045.
Sun et al. (2004) "Fabricating Semiconductor Nano/Microwires and Transfer Printing Ordered Arrays of them onto Plastic Substrates," Nano Lett. 4: 1953-1959..
Sun et al. (2005) "Advances in Organic Field-Effect Transistors," *J. Mater. Chem.*15:53-65.
Sun et al. (2005) "Bendable GaAs Metal-Semiconductor Field-Effect Transistors Formed with a Printed GaAs Wire Arrays on Plastic Substrates," Appl. Phys. Lett. 87:083501.
Sun et al. (2005) "Photolithographic Route to the Fabrication of Micro/Nanowires of II I-V Semiconductors," Adv. Funct. Mater. 15:30-40.
Sun et al. (2007) "Inorganic Semiconductors for Flexible Electronics," *Adv. Mater.* 19:1897-1916.
Sun et al. (2007) "Structural Forms of Single Crystal Semiconductor Nanoribbons for High-Performance Stretchable Electronics," J. Mater Chem. 17:832-840.
Sun et al. (2007) "Controlled Buckling of Semiconductor Nanoribbons for Stretchable Electronics," Nat. Nanotechnol. 1:201-207.
Sun et al. (2007) "Inorganic Semiconductors for Flexible Electronics," Adv. Mater. 19:1897-1916,
Sun et al. (Nov. 2006) "Buckled and Wavy Ribbons of GaAs for High-Performance Electronics on Elastomeric Substrates," Adv. Mater. 18(21):2857-2862.
Sun et al. (Web Release Dec. 5, 2006) "Controlled Buckling of Semiconductor Nanoribbons for Stretchable Electronics," Nature Nanotech. 1:201-207.
Sundar et al. (2004) "Elastomeric Transistor Stamps: Reversible Probing of Charge Transport in Organic Crystals," Science 303: 1644-1646.
Suo et al. (Feb. 22, 1999) "Mechanics of Rollable and Foldable Film-on-Foil Electronics," Appl. Phys. Lett. 74(8):11771179.
Supplemental European Search Report for European Application 07 84 1968, completed Mar. 31, 2011.
Supplementary European Search Report, Corresponding to European Application No. 04 81 2651, Completed Oct. 19, 2010.
Supplementary European Search Report, Corresponding to European Application No. EP 05 75 6327, Completed Sep. 25, 2009.
Swain et al. (2004) "Curved CCD Detector Devices and Arrays for Multi-Spectral Astrophysical Application and Terrestrial Stereo Panoramic Cameras,"Proc. SPIE 5499:281-301.
Sweet: Stretchable and Washable Electronics for Embedding Textiles. Available at http://tfcg.elis.ugent.be/projects/sweet. Access Feb. 8, 2012.
Sze et al. (1985) *Semiconductor Devices, Physics and Technology*, $2^{nd}$ ed., Wiley, New York, pp. 190-192.
Sze, S. (1985) "Lithography and Etching," In; *Semiconductor Devices: Physics and Technology, New York: Wiley, pp. 428-467*.
Sze, S. (1985) Semiconductor Devices: Physics and Technology, New York: Wiley, pp. 428-467.
Sze, S. (1988) VLSI Technology, Chapter 8, ION Implantation, Mcgraw-Hill, 327-374, 566-611.
Sze, S. (1994) "Semiconductor Sensor Technologies," In; *Semiconductor Sensors*,John Wiley and Sons: New York pp. 17-95.
Takamoto et al. (Jan. 20, 1997) "Over 30% Efficient InGaP/GaAs Tandem Solar Cells," Appl. Phys Lett. 70(3):381-383.
Talapin et al. (Oct. 7, 2005) "PbSe Nanocrystal Solids for n- and p-Channel Thin Film Field-Effect Transistor," Science 310:86-89.
Tan et al. (Apr. 12, 2004) "Performance Enhancement of InGaN Light Emitting Diodes by Laser-Lift-off and Transfer from Sapphire to Cooper Substrate," Appl. Phys. Lett. 84(15):2757-2759.
Tanase et al. (2002) "Magnetic Trapping and Self-Assembly of Multicomponent Nanowires," J. Appl. Phys. 91 :8549-8551.
Tang et al. (2005) "One-Dimensional Assemblies of Nanoparticles: Preparation,Properties, and Promise," Adv. Mater. 17:951-962.
Tao et al. (2003) "Langmuir-Blodgett Silver Nanowire Monolayers for Molecular Sensing Using Surface-Enhanced Raman Spectroscopy," Nano Lett. 3:1229-1233.
Tate et al. (2000) "Anodization and Microcontact Printing on Elotroless Silver: Solution-Based Fabrication Procedures for Low-Voltage Electronic Systems with Organic Active Components," Langmuir 16:6054-6060.
Teshima et al. (2001) "Room-Temperature Deposition of High-Purity Silicon Oxide Films by RF Plasma-Enhanced CVD," Surf. Coat. Technol. 146-147:451-456.
Theiss et al. (1998) "PolySilicon Thin Film Transistors Fabricated at 100 ° C. on a Flexible Plastic Substrate," IEDM 98:257-260.
Thornwood et al. (Oct. 1, 1990) "Utilizing Olptical Lithography in the Sub-Micron Dimensional Regime," IBM Tech. Disc. Bull. 33(5):187-188.
Timko et al. (2009) "Electrical Recording from Hearts with Flexible Nanowire Device Arrays," Nano Lett. 9:914-918.
Toader et al. (2004) "Photonic Band Gap Architectures for Holographic lithography," Phy. Rev. Lett. 043905/1-043905/4.
Toader et al. (2004) "Photonic Band Gaps Based on Tetragonal Lattices of Slanted Pores," Phys. Rev. Lett. 90:233901/1-233901/4.
Tong (1999) "Stresses in Bonded Wafers," In; Semiconductor Wafer Bonding: *Science and Technology,* John Wiley; New York, pp. 187-221.

(56) References Cited

OTHER PUBLICATIONS

Tong (1999) Semiconductor Wafer Bonding: Science and Technology, John Wiley; New York, pp. 187-221.
Trau et al. (1997) "Microscopic Patterning of Orientated Mesoscopic Silica Through Guided Growth," Nature 390:674-676.
Trentler et al. (1995) "Solution-liquid-Solid Growth of Crytalline III-V Semiconductors: An Analogy to Vapor-liquid-Solid Growth," Science 270:1791-1794.
Tseng et al. (Web Release Dec. 19,2003) "Monolithic Integration of Carbon Nanotube Devices with Silicon MOS Technology" Nano Lett. 4(1):123-127.
Ucjikoga, S. (2002) "Low-Temperature Polycrystalline Silicon Thin-Film Transistor Technologies of System-on-Glass Displays," MRS Bull. 27:881-886.
Urruchi et al. (2000) "Etching of DLC Films Using a Low Intensity Oxygen Plasma Jet," Diamond Relat. Mater. 9:685-688.
U.S. Appl. No. 11/423,287, filed Jun. 9, 2006.
U.S. Appl. No. 11/851,182, filed Sep. 6, 2006.
U.S. Appl. No. 12/398,811, filed Mar. 5, 2009.
U.S. Appl. No. 12/723,475, filed Mar. 12, 2010.
U.S. Appl. No. 12/575,008, filed Oct. 7, 2008.
U.S. Appl. No. 12/616,922, filed Nov. 12, 2009.
U.S. Appl. No. 12/625,444, filed Nov. 24, 2009.
U.S. Appl. No. 12/636,071, filed Dec. 11, 2009.
U.S. Appl. No. 12/686,076, filed Jan. 12, 2010.
U.S. Appl. No. 12/972,073, filed Dec. 17, 2010.
U.S. Appl. No. 12/976,607, filed Dec. 22, 2010.
U.S. Appl. No. 12/976,814, filed Dec. 22, 2010.
U.S. Appl. No. 12/976,833, filed Dec. 22, 2010.
U.S. Appl. No. 13/082,388, filed Apr. 7, 2010.
US Office Action for U.S. Appl. No. 12/575,008 mailed Feb. 17, 2011.
Vanhollenbeke et al. (2000) "Compliant Substrate Technology: Integration of Mismatched Materials for Opto-Electronic Applications," Prog. Cryst. Growth Charact. Mater. 41(1-4):1-55.
Velev et al. (1997) "Porous silica via colloidal crystallization," Nature 389:447-448.
Vepari et al. (Aug. Sep. 2007) "Silk as a Biomaterial," Prog. Polym. Sci. 32(8-9):991-1007.
Vilan et al. (2000) "Molecular Control Over Au/GaAs Diodes," Nature 404:166-168.
Vinck et al. (2003) "Increased Fibroblast Proliferation Induced by Light Emitting Diode and Low Power Laser Irradiation," Lasers Med. Sci. 18:95-99.
Viventi et al. (Mar. 2010) "A Conformal, Bio-Interfaced Class of Silicon Electronics for Mapping Cardiac Electrophysiology," Sci. Trans. Med. 2(24):24ra22.
Vlasov et al. (2001) "On-Chip Natural Assembly of Silicon Photonic Bandgap Crystals," Nature 414:289-293.
Voss, D. (2000) "Cheap and Cheerful Circuits," Nature 407:442-444.
Wagner et al. (2003) "Silicon for Thin-Film Transistors," Thin Solid Films 430: 15-19.
Wagner et al. (2005) "Electronic Skin: Architecture and Components," Physica E 25:326-334.
Wagner et al. (Mar. 1, 1964) "Vapor-liquid-Solid Mechanism of Single Crystal Growth," Appl. Phys. Lett. 4(5):89-90.
Waksman et al.(2008) "Photopoint Photodynamic Therapy Promotes Stabilization of Atherosclerotic Plaques and Inhibits Plaque Progression," J. Am. Coll. Cardiol. 52:1024-1032.
Wang et al. (2003) "A Solution-Phase, Precursor Route to Polycrystalline $SnO_2$ Nanowores That Can Be Used for Gas Sensing under Ambient Conditions," J. Am. Chem. Soc. 125:16176-16177.
Wang et al. (2005) "Oxidation Resistant Germanium Nanowires: Bulk Synthesis, Long Chain Alkanethiol Functionalization, and Langmuir-Blodgett Assembly," J. Am. Chem. Soc. 127(33):11871-11875.
Wang et al. (2005) "Electronically Selective Chemical Functionalization of Carbon Nanotubes: Correlation between Rama Spectral and Electrical Responses," J. Am. Chem. Soc., 127:11460-11468.
Wang et al. (2006) "Direct Synthesis and Characterization of CdS Nanobelts," Appl. Phys. Lett. 89:033102.
Wang et al. (Aug-Sep. 2008) "In Vivo Degradation of Three-Dimensional Silk Fibroin Scaffolds," Biomaterials 29(24-25):3415-3428.
Waxman et al. (2009) "In vivo Validation of a Catheter-Based Near-Infrared Spectroscopy System for Detection of Lipid Core Coronary Plaques: Initial Results of the Spectacl Study," J. Am. Coll. Cardiol. Img. 2:858-868.
Waxman, S. (2008) "Near-Infrared Spectroscopy for Plaque Characterization," J. Interv. Cardiol. 21:452-458.
Weber et al. (Jan. 2004) "A Novel Low-Cost, High Efficiency Micromachined Silicon Solar Cell," IEEE Electron Device Lett. 25(1):37-39.
Wen et al. (Web Release Dec. 4, 2004) "Controlled Growth of Large-Area, Uniform, Vertically Aligned Arrays of a-Fe2O2 Nanobelts and Nanowires," J. Phys. Chem. B 109(1):215-220.
Whang et al. (2003) "Large-Scale Hierarchical Organization of Nanowire Arrays for Integrated Nanosystems," Nano Lett. 3(9): 1255-1259.
Williams et al. (Oct. 2006) "Growth and Properties of Nanocrystalline Diamond Films," Phys. Stat. Sol. A 203(13):3375-3386.
Williams et al. (Web Release Jan. 23, 2006) "Comparison of the Growth and Properties of Ultranocrystalline Diamond and Nanocrystalline Diamond," Diamond Relat. Mater. 15:654-658.
Willner et al. (2002) "Functional Nanoparticle Architectures for Senoric, Optoelectronic, and Bioelectronic Applications," Pure Appl. Chem. 74(9): 1773-1783.
Wilson et al. (2006) "ECoG Factors Underlying Multimodal Control of a Brain—Computer Interface," IEEE Trans. Neural Syst. Rehabil. Eng. 14:246-250.
Wind et al. (May 20, 2002) "Vertical Scaling of Carbon Nanotube-Field-Effect Transitors Using Top Gate Electrodes," Appl. Phys. Lett. 80(20):3871-3819.
Wise et al. (Jul. 2008) "Microelectrodes, Microelectronics, and Implantable Neural Microsystems," Proc. IEEE 96(7):1184-1202.
Won et al. (2004) "Effect of Mechanical and Electrical Stresses on the Performance of an a-Si:H TFT on Plastic Substrate," J. Electrochem. Soc. 151:G167-G170.
Wong-Riley et al. (2005) "Photobiomodulation Directly Benefits Primary Neurons Functionally Inactivated by Toxins," J. Biol. Chem. 280:4761-4771.
Woodburn et al. (1996) "Phototherapy of Cancer and Atheromatous Plaque with Texaphyrins," J. Clin. Laser Med. Surg. 14:343-348.
Written Opinion of the International Search Authority Corresponding to International patent Application No. PCT/US05/19354 Issued Apr. 18, 2007.
Wu et al. (2001) "Amorphous Silicon Crystallization and Polysilicon Thin Film Transistors on SiO2 Passivated Steel Foil Substrates," Apple. Surf. Sci 175-176:753-758.
Wu et al. (2001) "Thermal Oxide of Polycrystalline Silicon on Steel Foil as a Thin-Film Transistor Gate Dielectric," Appl. Phys. Lett. 78:3729-3731.
Wu et al. (2001) "Direct Observation of Vapor-Liquid-Solid Nanowire Growth", J. Am. Chem. Soc. 123(13):3165-3166.
Wu et al. (2002) "Growth of Au-Catalyzed Ordered GaAs Nanowire Arrays by Molecular-Beam Epitaxy," Appl. Phys. Lett. 81 :5177-5179.
Wu et al. (2002) "Inorganic Semiconductor Nanowires: Rational Growth, Assembly, and Novel Properties," Chem. Eur. J. 8(6):1261-1268.
Wu et al. (2002) "Block-by-Block Growth of Single-Crystalline Si/SiGe Superlattice Nanowires," Nano Lett. 2(2):83-86.
Wu et al. (2002) "Growth of Au-Catalyzed Ordered GaAs Nanowire Arrays by Molecular-Beam Epitaxy," Appl. Phys. Lett. 81:5177-5179.
Wu et al. (2003) "Growth, Branching, and Kinking of Molecular-Beam Epitaxial (110) GaAs Nanowires," Appl. Phys. Lett. 83:3368-3370.
Wu et al. (Jul. 1, 2004) "Single-Crystal Metallic Nanowires and Metal/Semiconductor Nanowire Heterostructures," Nature 430:61-65.

(56) References Cited

OTHER PUBLICATIONS

Wu et al. (Nov. 2002) "Complementary Metal-Oxide-Semiconductor Thin-Film Transistor Circuits from a High-Temperature Polycrystalline Silicon Process on Steel Foil Substrates," IEEE Trans. Electr. Dev. 49(11):1993-2000.
Wu et al. (Web Release Jan. 19, 2002) "Block-by-Block Growth of Single Crystalline Si/SiGe Superlattice Nanowires," Nano Lett. 2(2):83-86 Si/SiGe Superlattice Nanowires, Nano Lett. 2(2):83-86.
Wu et al. (Web Release Mar. 13, 2001) "Direct Observation of Vapor-Liquid-Solid Nanowire Growth," J. Am. Chem. Soc. 123(13):3165-3166.
Xia (1998) "Soft Lithography" Angew. Chem. Int. Ed. 37:551-575.
Xia et al. (1996) "Shadowed Sputtering of Gold on V-Shaped Microtrenches Etched in Silicon and Applications in Microfabrication," Adv. Mater. 8(9):765-768.
Xia et al. (1998) "Soft Lithography," Annu. Rev. Mater. Sci. 28:153-184.
Xia et al. (1999) "Unconventional Methods for Fabricating and Patterning Nanostructures," Chem. Rev. 99:1834-1848.
Xia et al. (2003) "One-Dimensional Nanostructures: Synthesis, Characterization and Applications," Adv. Mater. 15:353-389.
Xia et al. (Jul. 19, 1996) "Complex Optical Surfaces Formed by Replica Molding Against Elastomeric Masters," Science 273:347-349.
Xiang et al. (Mar. 25, 2006) "Ge/Si Nanowire Heterostructures as High-Performance Field-Effect Transistors," Nature 441:489-493.
Xiao et al. (2003) "High-mobility thin-film transistors based on aligned carbon nanotubes," Appl. Phys. Lett., vol. 83, No. 1, pp. 150-152.
Xie et al. (May 2003) "Polymer-Controlled Growth of $Sb_2Se_3$ Nanoribbons Via a Hyrdothermal Process" J. Cryst. Growth 252(4):570-574.
Xin et al. (Jun. 2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," Biornaterials 26(16):3123-3129.
Yang et al. (1997) "Mesoporous Silica with Micrometer-Scale Desgns," Adv. Mater. 9:811-814.
Yang et al. (2000) "Stability of Low-Temperature Amorphous Silicon Thin Film Transistors Formed on Glass and Transparent Plastic Substrates," J. Vac. Sci. Technol. B 18:683-689.
Yang et al. (2002) "Creating Periodic Three-Dimensional Structures by Multibeam Interface of Visible Laser," Chem. Mater. 14:2831-2833.
Yang et al. (Dec. 2007) "RFID Tag and RF Structures on a Paper Substrate Using Inkjet-Printing Technology," IEEE Trans. Microw. Theory Tech. 55(12):2894-2901.
Yang, P. (2005) "The Chemistry and Physics of Semiconductor Nanowires," MRS Bull. 30:85-91.
Yanina et al. (2002) "Terraces and ledges on (001) spinel surfaces," Surf. Sci., 513:L402-L412.
Yao et al. (2008) "Seeing Molecules by Eye: Surface Plasmon Resonance Imaging at Visible Wavelengths with High Spatial Resolution and Submonolayer Sensitivity,"Angew. Chem. 47:5013-5017.
Yao et al. (2010) "Functional Nanostructured Plasmonic Materials," Adv. Mater. 22:1102-1110.
Yao et al. (Mar. 2000) "High-Field Effect Electrical Transport in Single-Walled Carbon Nanotubes," Phys. Rev. Lett. 84(13):2941-2944.
Yeager et al. (Aug. 30, 2008) "Characterization of Flexible ECoG Electrode Arrays for Chronic Recording in Awake Rats," J. Neurosci. Methods 173(2):279-285.
Yeh et al. (1994) "Fluidic Self-Assembly for the Integration of GaAs light-Emitting Diodes on Si Substrates," IEEE Photon. Technol. Lett. 6:706-708.
Yin et al. (2000) "A Soft lithography Approach to the Fabrication of Nanostructures of Single Crystalline Silicon with Well-Defined Dimensions and Shapes," Adv. Mater. 12:1426-1430.
Yin et al. (2005) "Colloidal Nanocrystal Synthesis and the Organic-Inorganic Interface," Nature 437:664-670.
Yoon et al. (2005) "Low-Voltage Organic Field-Effect Transistors and Inverters Enabled by Ultrathin Cross-linked Polymers as Gate Dielectrics," J. Am. Chern. Soc. 127: 10388-10395.
Yu et al. (2000) "Silicon Nanowires: preparation, Device Fabrication, and Transport Properties," J. Phys. Chem. B 104(50):11864-11870.
Yu et al. (2003) "Solution-liquid-Solid Growth of Soluble GaAs Nanowires," Adv. Mater. 15:416-419.
Yu et al. (2003) "Two-Versus Three-Dimensional Quantum Confinement in Indium Phosphide Wires and Dots," Nat. Mater. 2:517-520.
Yu et al. (2004) "The Yield Strength of Thin Copper Films on Kapton," J. Appl. Phys. 95:2991-2997.
Yuan et al. (2006) "High-Speed Strained-Single-Crystal-Silicon Thin-Film Transistors on Flexible Polymers," J. Appl. Phys. 100:013708.
Yurelki et al. (Jul. 24, 2004) "Small-Angle Neutron Scattering from Surfactant-Assisted Aqueous Dispersions of Carbon Nanotubes," J. Am. Chem. Soc. 126(32):9902-9903.
Zakhidov et al. (1998) "Carbon Structure with Three-Dimensional Periodicity at Optical Wavelengths," Science 282:897-901.
Zaumseil et al. (2003) "Nanoscale Organic Transistors that use Source/Drain Electrodes Supported by High Resolution Rubber Stamps," Appl. Phys. Lett. 82(5):793-795.
Zaumseil et al. (2003) "Three-Dimensional and Multilayer Nanostructures Formed by Nanotransfer Printing," Nano Lett. 3(9):1223-1227.
Zhang et al. (2001) "Electric-field-directed growth of aligned single-walled carbon nanotubes," Appl. Phys. Lett., vol. 79, No. 19. pp. 3155-3157.
Zhang et al. (2005) "Low-Temperature Growth and Photoluminescence Property of ZnS Nanoribbons," J. Phys. Chem. B 109(39):18352-18355.
Zhang et al. (2006) "Anomalous Coiling of SiGe/Si and SiGe/Si/Cr Helical Nanobelts," Nano Lett. 6(7):1311-1317.
Zhang et al. (Apr. 2003) "Oxide-Assisted Growth of Semiconducting Nanowires," Adv. Mater. 15(7-8):635-640.
Zhang et al. (Apr. 5, 2004) "Structure and Photoiluminescence of ZnSe Nanoribbons Grown by Metal Organic Chemical Vapor Deposition," Appl. Phys. Lett. 84(14):2641-2643.
Zhang et al. (Feb. 9, 2006) "Electronic Transport in Nanometre-Scale Silicon-on-Insulator Membranes,"Nature 439:703-706.
Zhang et al. (Jun. 6, 2006) "Anomalous Coiling of SiGe/Si and SiGe/Si/Cr Helical Nanobelts," Nano Lett. 6(7):1311-1317.
Zhao et al. (Mar. 2007) "Improved Field Emission Properties from Metal-Coated Diamond Films," Diamond Relat Mater. 16(3):650-653.
Zheng et al. (1998) "Sudden Cardiac Death in the United States, 1989 to 1998," Circulation 104, 2158-2163.
Zheng et al. (2004) "Shape-and Solder-Directed Self-Assembly to Package Semiconductor Device Segments," Appl. Phys. Lett. 85:3635-3637.
Zheng et al. (Aug. 31, 2004) "Sequential Shape-and-Solder-Directed Self Assembly of Functional Microsystems," Proc. Natl. Acad. Sci. USA 101(35):12814-12817.
Zhou et al. (2002) "An Efficient Two-Photon-Generated Photoacid Applied to Positive-Tone 3D Microfabrication," Science 296:1106-1109.
Zhou et al. (2004) "p-Channel, n-Channel Thin Film Transistor and p-n Diodes Based on Single Wall Carbon Nanotube Networks," Nano Lett. 4:2031-2035.
Zhou et al. (2005) "Band Structure, Phonon Scattering, and the Performance Limit of Single-Walled Carbon Nanotube Transistors," Phys. Rev. Lett. 95:146805.
Zhou et al. (2005) "Mechanism for Stamp Collapse in Soft Lithography," Appl. Phys.Lett. 87:251925.
Zhu et al. (2005) "Spin on Dopants for High-Performance Single Crystal Silicon Transistors on Flexible Plastic Substrates," Applied Physics Letters 86, 133507 (2005).
Zipes et al. (2006) "ACC/AHA/ESC 2006 Guidelines for Management of Patients With Ventricular Arrhythmias and the Prevention of

(56) References Cited

OTHER PUBLICATIONS

Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death," Circulation 114:385-484.

* cited by examiner

US 9,012,784 B2

EXTREMELY STRETCHABLE ELECTRONICS

CROSS-REFERENCE TO RELATED APPLICATIONS

This application is a continuation of U.S. Non-Provisional application Ser. No. 12/616,922, entitled "Extremely Stretchable Electronics," filed on Nov. 12, 2009, which claims the benefit of the U.S. Provisional Application No. 61/113,622 entitled "Extremely Stretchable Interconnects" filed on Nov. 12, 2008, the entirety of which is incorporated herein by reference. U.S. Non-Provisional application Ser. No. 12/616,922 also is a continuation-in-part of, and claims the benefit of U.S. Non-Provisional application Ser. No. 12/575,008, entitled "Catheter Balloon Having Stretchable Integrated Circuitry and Sensor Array" filed on Oct. 7, 2009, the entirety of which is incorporated herein by reference. application Ser. No. 12/575,008 claimed priority of U.S. Provisional Application Nos. 61/103,361, filed Oct. 7, 2008 and 61/113,007, filed Nov. 10, 2008 the entirety of each of which is incorporated herein by reference.

FIELD OF THE INVENTION

The present invention relates to systems, apparatuses, and methods utilizing expandable or stretchable integrated circuitry, and more particularly to extremely stretchable integrated circuitry.

BACKGROUND OF THE INVENTION

The field of stretchable electronics continues to grow due to the demand of high performance and mechanically unconstrained applications of the future. However, stretchable electronics have been thus far limited in stretchability. This has limited the ability of stretchable electronics to accommodate applications that require more extreme stretchability. Therefore a need exists for extremely stretchable electronics.

SUMMARY OF THE INVENTION

This invention is for extremely stretchable electrical interconnects and methods of making the same. In embodiments, the invention comprises a method of making stretchable electronics, which in some embodiments can be out of high quality single crystal semiconductor materials or other semiconductor materials, that are typically rigid. For example, single crystal semiconductor materials are brittle and cannot typically withstand strains of greater than about +/−2%. This invention describes a method of electronics that are capable of stretching and compressing while withstanding high translational strains, such as in the range of −100,000% to +100,000%, and/or high rotational strains, such as to an extent greater than 180°, while maintaining electrical performance found in their unstrained state.

In embodiments, the stretching and compressing may be accomplished by fabricating integrated circuits (ICs) out of thin membrane single crystal semiconductors, which are formed into "islands" that are mechanically and electrically connected by "interconnects," and transferring said ICs onto an elastomeric substrate capable of stretching and compressing. The islands are regions of non-stretchable/compressible ICs, while the interconnects are regions of material formed in a way to be highly stretchable/compressible. The underlying elastomeric substrate is much more compliant than the islands, so that minimal strain is transferred into the islands while the majority of the strain is transferred to the interconnects, which only contain electrical connections and not ICs. Each interconnect attaches one island to another island, and is capable of accommodating strain between the two aforementioned islands, including translation, rotation, or a combination of translation with rotation of one island relative to another. Even though the interconnects may be made of a rigid material, they act like weak springs rather than rigid plates or beams. This configuration thereby allows for the making of extremely stretchable electronics.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE DRAWINGS

The invention and the following detailed description of certain embodiments thereof may be understood by reference to the following figures.

While the invention has been described in connection with certain preferred embodiments, other embodiments would be understood by one of ordinary skill in the art and are encompassed herein.

All documents referenced herein are hereby incorporated by reference.

DETAILED DESCRIPTION OF THE INVENTION

The present invention accomplishes extremely stretchable electronics by forming the electronics on discrete islands 102 of silicon.

With reference to the present invention, the term "stretchable", and roots and derivations thereof, when used to modify circuitry or components thereof is meant to encompass circuitry that comprises components having soft or elastic properties capable of being made longer or wider without tearing or breaking, and it is also meant to encompass circuitry having components (whether or not the components themselves are individually stretchable as stated above) that are configured in such a way so as to accommodate and remain functional when applied to a stretchable, inflatable, or otherwise expandable surface. The term "expandable", and roots and derivations thereof, when used to modify circuitry or components thereof is also meant to have the meaning ascribed above. Thus, "stretch" and "expand", and all derivations thereof, may be used interchangeably when referring to the present invention.

In embodiments, the discrete islands mention above are discrete operative (in embodiments, arranged in a "device island" arrangement) and are themselves capable of performing the functionality described herein, or portions thereof. In embodiments, such functionality of the operative devices can include integrated circuits, physical sensors (e.g. temperature, pH, light, radiation etc), biological and/or chemical sensors, amplifiers, A/D and D/A converters, optical collectors, electro-mechanical transducers, piezo-electric actuators, light emitting electronics which include LEDs, and combinations thereof. The purpose and advantage of using standard ICs (in embodiments, CMOS, on single crystal silicon) is to have and use high quality, high performance, and high functioning circuit components that are also already commonly mass-produced with well known processes, and which provide a range of functionality and generation of data far superior to that produced by a passive means.

Figure 1:
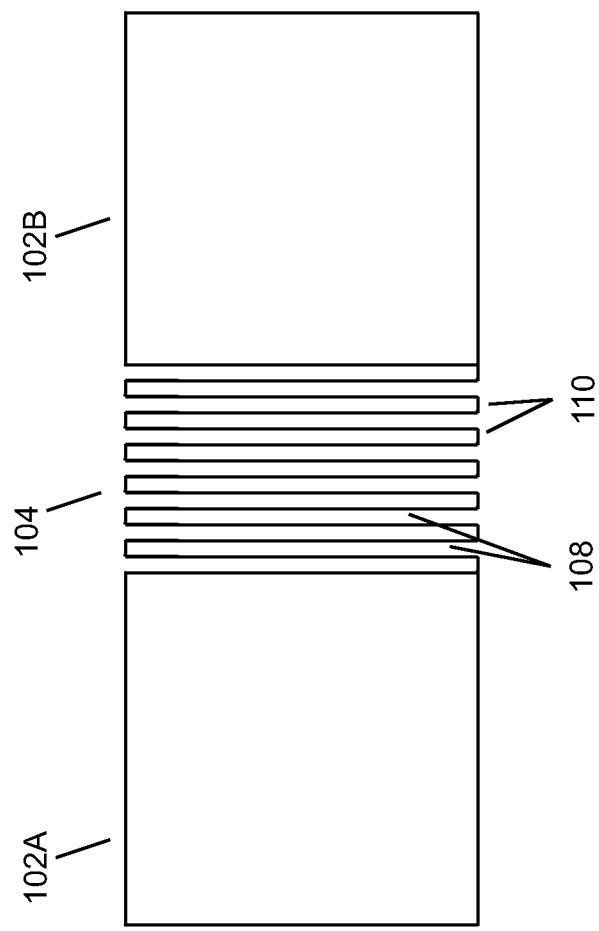
FIG. 1 depicts an overhead view of an embodiment of the present invention showing two device islands connected edge-to-edge by a monolithically formed extremely stretchable interconnect, prior to being stretched.

In an example, the discrete islands 102 may range from about, but not limited to, 10-100 µm in size measured on an edge or by diameter, and connecting said islands 102A-B with one or more extremely stretchable interconnects 104. The novel geometry of the interconnects 104 is what makes them extremely compliant. Each interconnect 104 is patterned and etched so that its structural form has width and thickness dimensions that may be of comparable size (such as their ratio or inverse ratio not exceeding about a factor of 10); and may be preferably equal in size. In embodiments, the dimensions may not be greater than about 5 um (e.g. where both dimensions are about 1 µm or less). The interconnect 104 may be formed in a boustrophedonic style such that it effectively comprises long bars 108 and short bars 110 as shown in FIG. 1. This unique geometry minimizes the stresses that are produced in the interconnect 104 when subsequently stretched because it has the effective form of a wire, and behaves very differently than interconnect form factors having one dimension greatly exceeding the other two (for example plates). Plate type structures primarily relieve stress only about a single axis via buckling, and withstand only a slight amount of shear stress before cracking. This invention may relieve stress about all three axes, including shears and any other stress.

Figure 2:
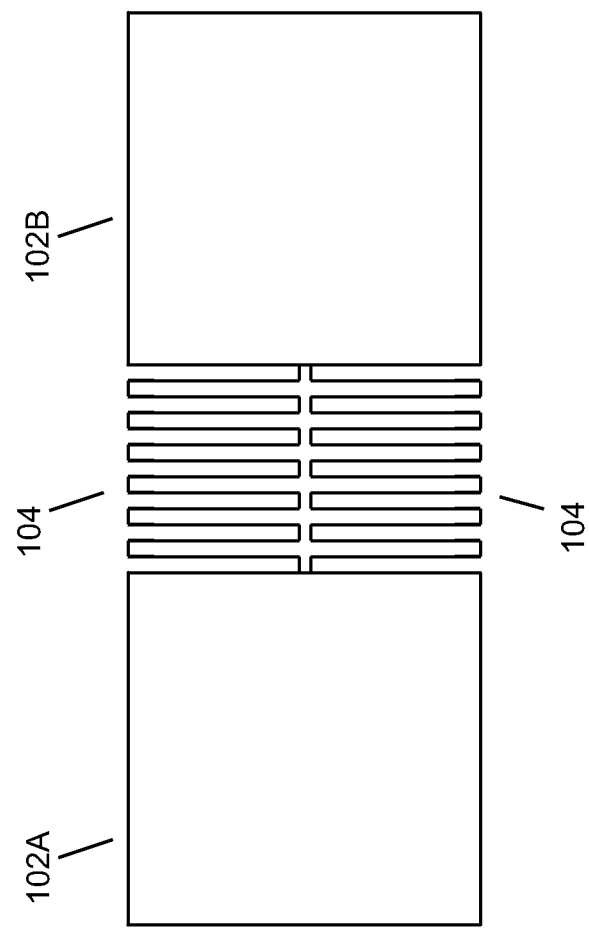
FIG. 2 depicts an overhead view of an embodiment of the present invention showing two device islands connected edge-to-edge by two extremely stretchable interconnects.
Figure 3:
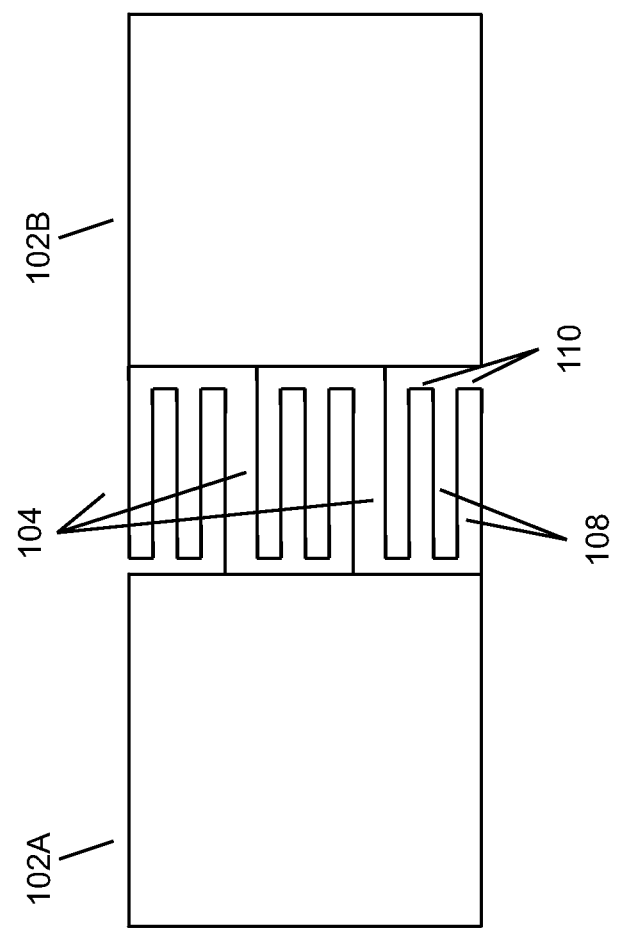
FIG. 3 depicts an overhead view of an embodiment of the present invention showing two device islands connected edge-to-edge by three extremely stretchable interconnects; in this case, the long bars of the interconnects are rotated by 90° which allows them to be longer than if they were not rotated.
Figure 4:
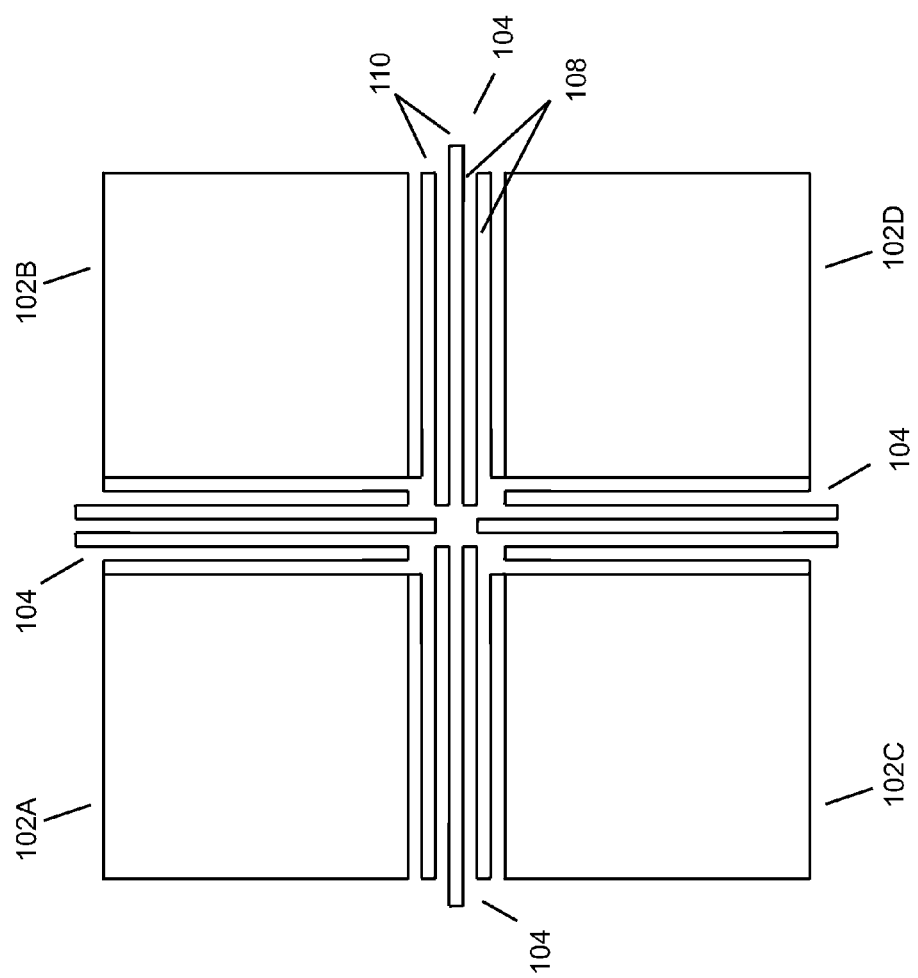
FIG. 4 depicts four device islands arranged in a square matrix in an embodiment of the present invention, with each edge connected by an extremely stretchable interconnect to its nearest neighbors island edge, and the interconnects are formed so as to maximize the amount of chip area that is used for either an island or interconnect.
Figure 5:
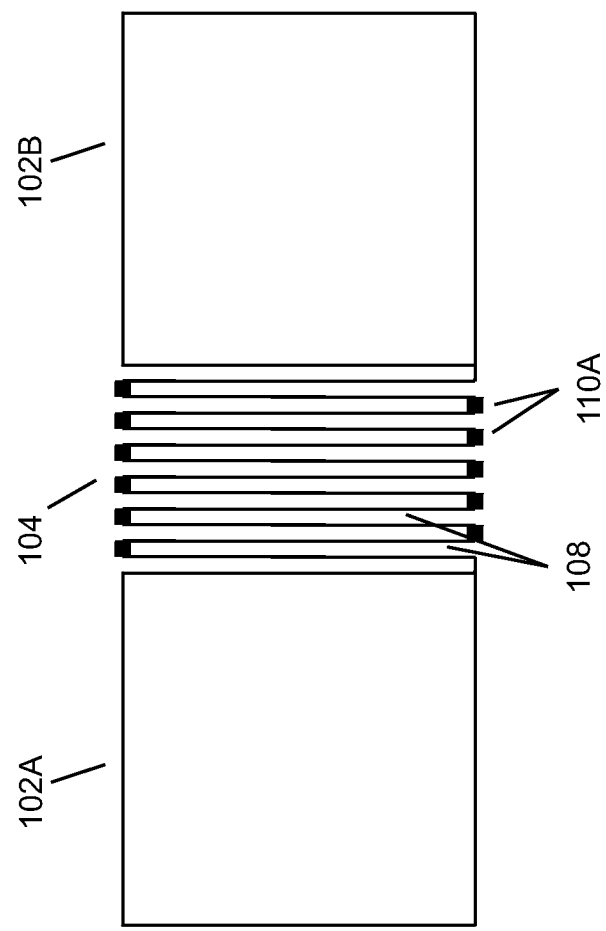
FIG. 5 depicts the case of FIG. 1, with the short bars widened for extra mechanical strength at those locations.

In addition, because the interconnect 104 may be formed out of rigid materials, after being stretched it may have a restorative force which helps prevent its wire-like form from getting tangled or knotted when re-compressing to the unstretched state. Another advantage of the boustrophedonic geometry is that it minimizes the initial separation distance between the islands 102A-B. This is illustrated in FIG. 1. One or more interconnects 104 may be formed in various ways, as shown in FIGS. 2-4. The parts of the interconnect 104 where the majority of stresses build up during stretching may be the short linking bars. To minimize cracking here, the short linking bars 110A may be made several micrometers wider than the longer bars 108, as shown in FIG. 5.

In embodiments, the connection point of the interconnect 104 to the device island 102 may be anywhere along the device island edge, or may be at a point on the surface of the device island 102 (in which case the interconnect may be located just above the plane of the device island).

In embodiments, device islands 102 may be made on any suitable material substrate, provided that a top membrane layer of said substrate that contains the ICs can be freed from the bulk of the substrate and transfer printed onto an elastomeric substrate.

Figure 6:
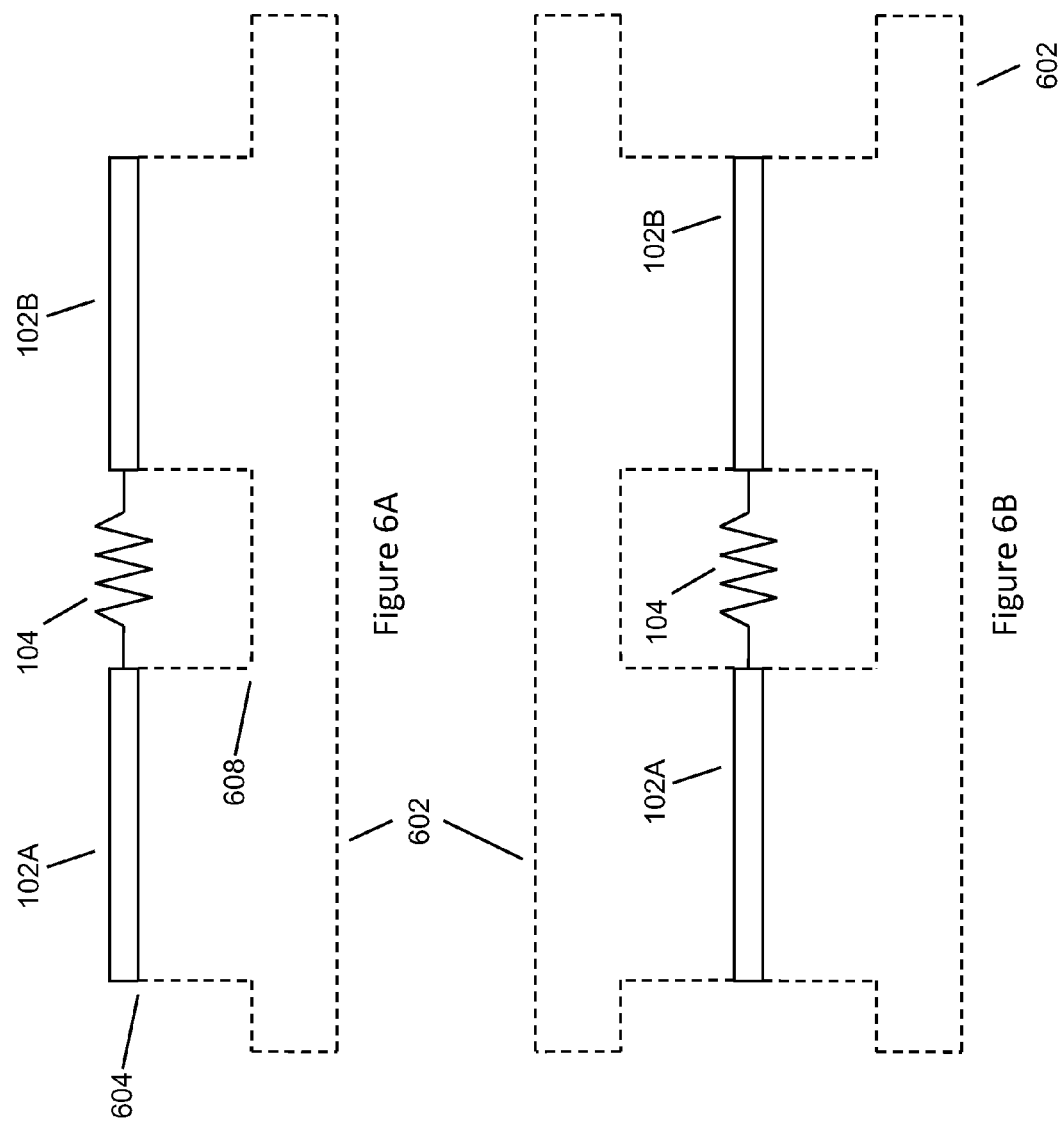
FIG. 6 depicts embodiments of the present invention, where (a) is a side view of device islands and extremely stretchable interconnects transferred onto an elastomeric substrate. In this case, the substrate has been molded to have posts that are of the same area as the device islands (note that in embodiments these could be smaller or larger than the device islands). The height "h" of the molded post regions may range from, but is not limited to, about 1-1000 μm. The interconnects are located in between these regions as shown. (b) Side view as before, with a similarly shaped elastomeric superstrate to serve as an encapsulation layer protecting the devices from direct mechanical contact.

In the present invention, the interconnects 104 (as described herein) may be formed either monolithically (i.e., out of the same semiconductor material as the device islands) or may be formed out of another material. In one non-limiting example embodiment, the stretchable electronics are fabricated on a silicon-on-insulator (SOI) wafer, having a 1 µm thick top silicon layer and a 1 µm thick buried oxide layer. Devices are formed on the top silicon wafer, and arranged into a square pattern of islands 102A-D and interconnects 104 of the general form shown in FIG. 4, in which the islands 102 are 100 µm on an edge, and the interconnects 104 are 1 µm wide, and the space between each long bar is 1 µm, and the interconnects 104 comprise 10 long bars 108, all about 100 µm long. The islands 102 and interconnects 104 are formed in an etching step which removes the excess silicon. The islands 102 and interconnects 104 are coated with a 1 um layer of polyimide that is patterned to only cover the islands 102 and interconnects 104. Next, the islands 102 and interconnects 104 are released in an HF etch which undercuts the underlying buried oxide. After drying, the islands 102 and interconnects 104 are transfer printed with a Polydimethylsiloxane (PDMS) stamp onto an elastomeric substrate 602. After being picked up by the transfer stamp, and prior to being placed onto the elastomeric substrate 602, the backsides of the islands 102 may be coated with a layer of polyimide (patterned to only cover the islands 102 and interconnects 104), and an additional layer of evaporated 3 nm chromium and 30 nm silicon dioxide selectively over the island regions to improve adhesion to the elastomeric substrate 602 at those locations, and not along the interconnects 102. The elastomeric substrate 602 may be PDMS or another highly compliant material. The elastomeric substrate 602 may additionally be molded or etched into the shape shown in FIG. 6A-B, to further increase selective adhesion in the device island region but not the interconnect region, and to reduce the amount of material strain in the elastomeric substrate 602 that is transferred to the device islands 102. In this example, the interconnects may accommodate stretching the device islands apart by approximately up to 800 µm. In addition, the interconnects 104 of this example may be capable of accommodating lateral shear displacements of about 800 µm. In general, they may be capable of accommodating any relative displacement of the two islands such that they remain approximately within 800 µm of each other. In addition, the interconnects 104 may accommodate corkscrew type rotations of one island relative to another about any of the three axes of rotation. This feature may be limited only by the interconnects becoming entangled within each other. In any practical application, the completed stretchable device may not be so severely rotated, and the interconnect may easily accommodate rotations of up to 180°. It is noted that by increasing the number of long bars 108 used in the interconnect 104, or by increasing the length of the long bars 108, the interconnect may be able to accommodate even larger displacement strains. In embodiments, there may be no practical upper limit to the amount of displacement enabled through the present invention.

Figure 7:
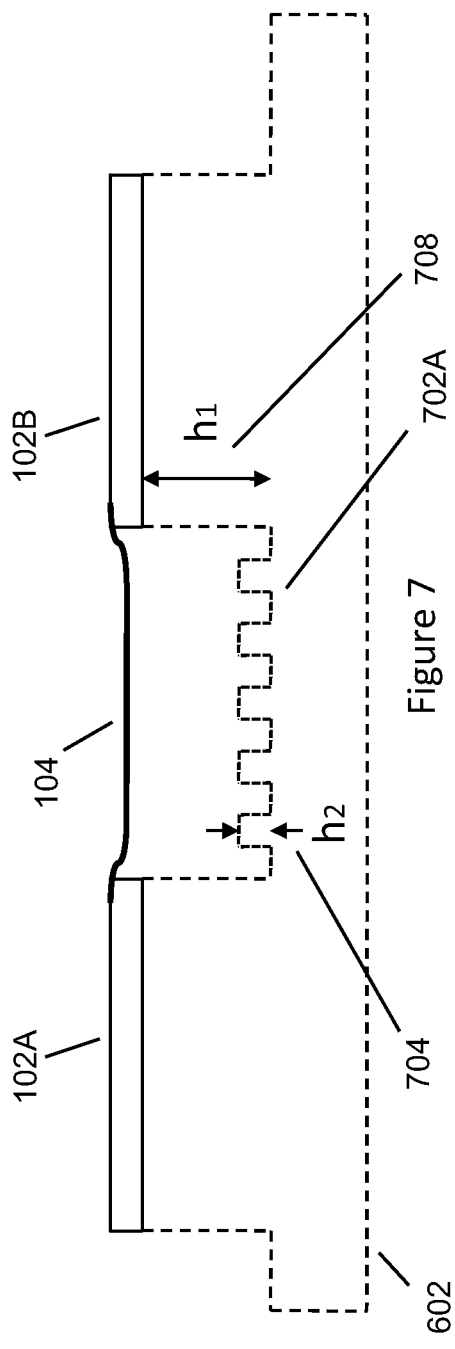
FIG. 7 depicts a side view of a two-layer PDMS substrate in an embodiment of the present invention comprising silicon device islands adhered to top layer, free-standing interconnects, and square wave ripples in the lower layer PDMS to promote increased stretching through the substrate.
Figure 8:
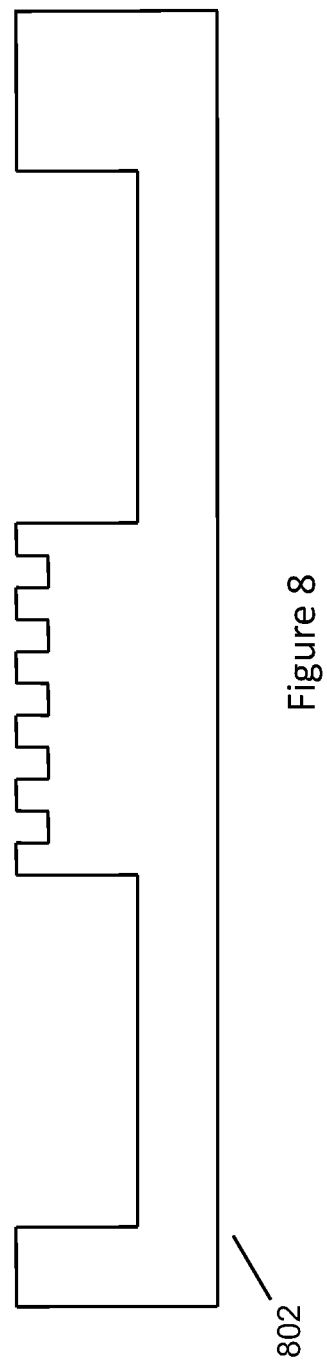
FIG. 8 depicts an embodiment of the present invention with a side view of two layers of cured photoresist (SU-8 50 and SU-8 2002) used to make the two-layer PDMS substrate described in FIG. 7.

In another embodiment the elastomeric substrate 602 may comprise two layers separated by a height. The top "contact" layer contacts the device island 102 as in the embodiment illustrated in FIG. 6. In addition, FIG. 7 shows the bottom layer 702 may be a "wavy" layer containing ripples or square waves molded into the substrate 602 during elastomer fabrication. These square waves enable additional stretching, whose extent depends on the amplitude and wavelength of the waves pattern-molded in the elastomer 602. FIG. 7 shows one non-limiting layout and topology of an elastomeric substrate 602 relative to the position of the interconnects 104 and device islands 102A-B. In an example, a two layer molded substrate can be fabricated using two step process consisting of two types of negative photoresist (SU-8 50 and SU-8 2002; Microchem Corporation). The negative resists can be spin-coated on a transfer silicon wafer with spin speeds of 3000 rpm. The SU-8 50 layer can be spun on the wafer, and subsequently cured with UV radiation. Once the SU-8 50 layer has hardened, the SU-8 2002 can be spun and cured with a photo-mask and an alignment tool. In this example, the thickness of the SU-8 50 and SU-8 2002 are 40-50 µm 708 and 2-10 µm 704, respectively. The 40-50 µm thick regions of SU-8 50 contain ripples 702 of SU-8 2002 (in this instance in the form of square waves) on their surfaces. Upon curing of the SU-8 2002 layer, liquid PDMS can be poured over the SU-8 patterns to form a substrate in the shape of the SU-8 molds 802, as shown in FIG. 8. The amplitude of the ripples in the SU-8 mold 802 can be varied by changing the spin speed used for spinning the thin layer of SU-8 2002. In this configuration, the interconnects 104 are free-standing. The entire substrate-device configuration can be immersed in non-cured elastomer (fluid layer) layer followed by a cured layer of PDMS to encapsulate the fluid and devices.

Figure 9:
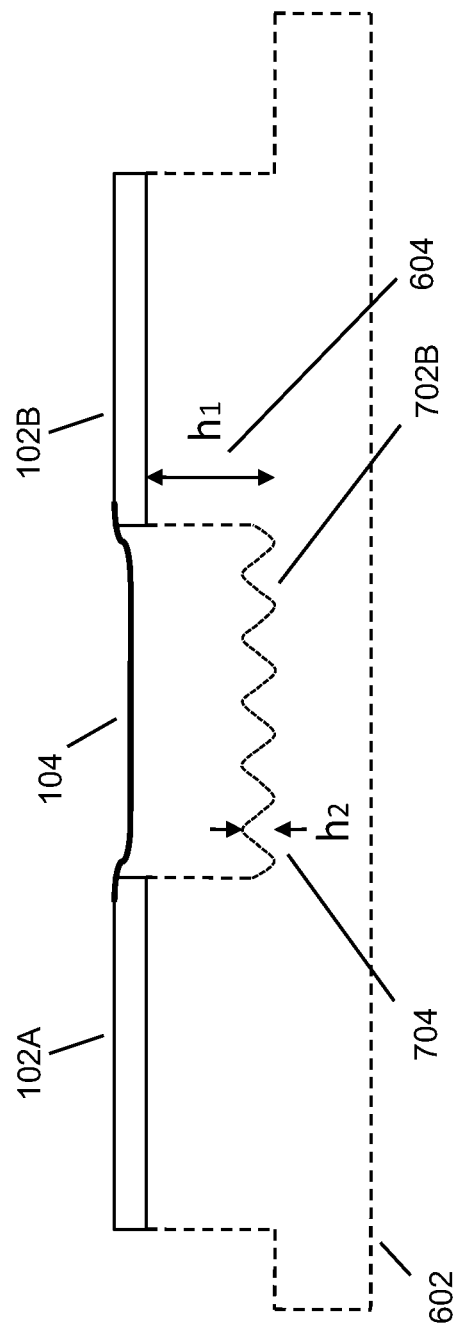
FIG. 9 depicts an embodiment of the present invention with a side view of a two-layer PDMS substrate consisting of sinusoidal waves in the lower layer of PDMS to promote increased stretching through the substrate.

In another embodiment, the PDMS in the lower layer may be designed with periodic sinusoidal ripples 702B. In embodiments, this ripple configuration may be achieved by bonding Si nanoribbons on the surface of pre-strained PDMS in a uniform parallel pattern. The release of the prestrain in the PDMS substrate generates sinusoidal waves along the thin Si-nanoribbons (caused by buckling) and the surface of the PDMS substrate. The amplitude and wavelength of these waves 702B may depend on the extent of uniaxial pre-strain exerted on the PDMS and on the mechanical properties of the Si-nanoribbons. The wavy surface on the PDMS may be used as a transfer mold. Two-part liquid plastic solution can be poured over the wavy PDMS substrate and cured at room temperature over time (~2 hrs). Once the plastic hardens, the plastic substrate can be peeled away from the PDMS. This new plastic transfer substrate with wavy surface features can be used to produce more PDMS substrates containing wave features. The wavy PDMS may serve as the lower layer of PDMS as in the previous embodiment. To produce a two layer PDMS structure, a top layer of PDMS can be plasma bonded to this lower layer of PDMS using oxygen plasma surface activation to produce the substrate illustrated in FIG. 9.

In another embodiment, the PDMS transfer stamp is stretched after the islands 102A-B and interconnects 104 are picked up. A subsequent transfer to another elastomeric substrate 602 may place these pre-stretched devices in a configuration, which allows the new elastomeric substrate to undergo compression. The devices may be able to accommodate that compression because the interconnects are pre-stretched.

In another embodiment, the interconnects 104 are not made out of the same material as the device islands 102. In this case, the islands 102A-B are completely isolated from each other by etching, with no interconnects in between. In an example, a layer of polyimide may then be deposited, contact vias etched to various locations on the surface of the device island 102, and then metal interconnects 104 deposited and patterned into a boustrophedonic pattern, followed by another layer of polyimide. Both layers of polyimide may now be patterned and etched to leave a small border around the interconnects 104 (thereby fully encapsulating the interconnects). These interconnects may have the advantage that they are already fully encapsulated in polyimide and will not adhere as well to the elastomeric substrate as the device islands will. The other advantage is that these interconnects may not be limited to only connecting along the edge of an island. The contact via may be etched anywhere on the surface of the island 102, including near the center. This may allow for easier connections to devices, more connections than possible only along an edge, increased strain compliance, decreased strain at the contact vias, and multiple layers of interconnects made with polymer passivation layers in between, allowing even more interconnects, or allowing one device island 102A to connect to a non-neighboring device island 102B.

In another embodiment of the invention, the device islands 102 are fabricated and transfer printed onto the elastomeric substrate 602, or substrate comprising a polymeric release layer and polymeric non-release layer. After transfer printing, the interconnects 104 are formed as described above, which may be possible because they do not require any high temperature processing, and then in the latter case, the release layer is etched and the devices that are on the non-release layer, are transfer printed onto another elastomeric substrate 602. In the former case, the islands 102 may be transferred onto the elastomeric substrate using pick and place technology so that islands 102 that are initially fabricated very close to each other are spread apart when they are transfer printed. This allows the interconnects 104 to be fabricated in a pattern that resembles their stretched configuration (if desired), to allow compression.

In embodiments, the present invention may comprise a stretchable electrical interconnect 104, including an electrical interconnect 104 for connecting two electrical contacts 102A-B (e.g. device islands 102A-B), where the electrical interconnect 104 may be arranged boustrophedonicially to define rungs 108 (i.e. long bars 108) between the contacts 102A-B, and where the rungs 108 may be substantially parallel with one another and where a plurality of rungs 108 may have substantially the same length and displacement therebetween. In addition, the ratio of the length of the plurality of rungs 108 and the displacement between the plurality of rungs 108 may be large, such as at least 10:1, 100:1, 1000:1, and the like. The electrical integrity of the electrical interconnect 104 may be maintained as stretched, such as to displacements that are increased to 1000%, 10000%, 100000%, and the like during stretching. In embodiments, the rungs 108 may be substantially perpendicular to the contacts 102A-B, the interconnection 104 may have a trace width and/or inter-rung spacing ranging between 0.1-10 microns. In embodiments, the two electrical contacts 102A-B may be located on an elastomeric substrate 602, the electrical contacts 102A-B may be bonded to the substrate 602 and the interconnection 104 not bonded to the substrate 602, the electrical contacts 102A-B may be semiconductor circuits, metal contacts, and the like.

In embodiments, the present invention may comprise a stretchable electrical interconnect 104, including an electrical interconnect 104 for connecting two electrical contacts 102A-B, where the electrical interconnect 104 is arranged boustrophedonicially to define rungs 108 between the contacts 102A-B, and where the interconnect 104 maintains electrical conductivity and electrical integrity when a displacement between the contacts 102A-B is increased, such as by 1000%, 10000%, 100000%, and the like.

In embodiments, the present invention may electrically interconnect two electrical contacts 102A-B with a stretchable interconnection 104 that has the ability to twist between the two electrical contacts 102A-B by up to approximately 180 degrees while maintaining electrical integrity of the stretchable interconnection 104.

In embodiments, the present invention may be a device including a body having a stretchable surface (e.g. an elastomeric substrate 602), and a stretchable electronic circuit including (i) a first discrete operative device 102A, (ii) a second discrete operative device 102B, and (iii) a stretchable interconnect 104 connecting the first discrete operative device 102A to the second discrete operative device 102B, where the interconnect 104 may have a substantially boustrophedonic pattern and be able to maintain electrical conductivity when stretched, such as up to 1000%, 10000%, 100000%, and the like. The stretchable electronic circuit may be affixed to the stretchable surface of the body. In embodiments, the connection may be to a metal contact, to a semiconductor device, and the like. The first discrete operative device 102A, the second discrete operative device 102B, and the stretchable interconnect 104 may all be made from the same material, and that material may be a semiconductor material.

In embodiments, the present invention may attach at least two isolated electronic components (which in embodiments may be discrete operative devices) 102A-B to an elastomeric substrate 602, and arrange an electrical interconnection 104 between the components 102A-B in a boustrophedonic pattern interconnecting the two isolated electronic components 102A-B with the electrical interconnection 104. The elastomeric substrate 602 may then be stretched such that components 102A-B separate relative to one another, where the electrical interconnection 104 maintains substantially identical electrical performance characteristics that the electrical interconnection 104 had in a pre-stretched form. In embodiments, the stretching may be a translational stretching, where the separation between the isolated electronic components 102A-B increases by a percent as a result of the stretching, such as 10%, 100%, 1000%, 10000%, 100000%, and the like. The stretching may be a rotational stretching, where the rotation may be greater than a certain rotation angle, such as 90°, 180°, 270°, 360°, and the like, where the stretching may be in all three axes. In embodiments, the electrical interconnection 104 may be made from semiconducitve material. The electrical interconnection 104 may be made from the same semiconductor material as the isolated electronic components 102A-B, fabricated at the same time as the isolated electronic components 102A-B, and the like. The semiconductor material may be a single crystal semiconductor material. The electrical interconnection 104 may made of a different material than the isolated electronic components 102A-B, such as a metal. In embodiments, the interconnect material 104 may be loosely bound to the elastomeric substrate 602, not connected at all, raised above the surface of the elastomeric substrate 602, and the like. In embodiments, the at least two isolated semiconductor circuits may be fabricated on an upper surface 604 of the elastomeric substrate 602 separated by a lower surface 608 of the elastomeric substrate 602, and the electrical interconnection 104 may be fabricated at the level of the upper surface 604 of the elastomeric substrate 602. In this way, the electrical interconnection 104 may have no direct contact with the lower level 608, and thereby be substantially free from adhesion to the lower level 608 during stretching. In addition, the lower surface 608 of the elastomeric substrate 602 may include a wavy form 702, where the wavy form 704 may allow the elastomeric substrate 602 to expand during stretching.

While the invention has been described in connection with certain preferred embodiments, other embodiments would be understood by one of ordinary skill in the art and are encompassed herein.

All documents referenced herein are hereby incorporated by reference.

What is claimed is:

1. A stretchable electrical interconnect, comprising:
an electrical interconnect for coupling two electrical contacts, said electrical interconnect being arranged boustrophedonically to define rungs between said two electrical contacts, said rungs being substantially parallel with one another, and a plurality of said rungs having substantially the same length and displacement therebetween, wherein the ratio of said length of said plurality of said rungs and said displacement between said plurality of said rungs is at least about 10:1.

2. The stretchable electrical interconnect of claim 1, wherein said rungs are substantially perpendicular to said contacts.

3. The stretchable electrical interconnect of claim 1, wherein the ratio is at least 100:1.

4. The stretchable electrical interconnect of claim 1, wherein said electrical interconnect maintains electrical integrity when the stretchable electrical interconnect is stretched.

5. The stretchable electrical interconnect of claim 4, wherein said electrical interconnect maintains electrical integrity when said displacement between said contacts is increased by 1000%.

6. The stretchable electrical interconnect of claim 4, wherein said electrical interconnect maintains electrical integrity when said displacement between said contacts is increased by 10000%.

7. The stretchable electrical interconnect of claim 4, wherein said electrical interconnect maintains electrical integrity when said displacement between said contacts is increased by 100000%.

8. The stretchable electrical interconnect of claim 1, wherein the electrical interconnect has a trace width ranging between 0.1-10 microns.

9. The stretchable electrical interconnect of claim 1, wherein the two electrical contacts are located on an elastomeric substrate.

10. The stretchable electrical interconnect of claim 9, wherein the electrical contacts are bonded to the elastomeric substrate, and wherein the electrical interconnect is not bonded to the substrate.

11. The stretchable electrical interconnect of claim 9, wherein the electrical contacts are semiconductor circuits.

12. The stretchable electrical interconnect of claim 9, wherein the electrical contacts are metal contacts.

13. A stretchable electrical interconnect, comprising:
an electrical interconnect for coupling two electrical contacts, wherein said electrical interconnect is arranged boustrophedonically to define rungs between said two electrical contacts, wherein said electrical interconnect maintains electrical conductivity between the two electrical contacts when a displacement between the two electrical contacts is increased by about 1000%.

14. A device, comprising:
a body having a stretchable surface; and
a stretchable electronic circuit comprising:
  (i) a first discrete operative device;
  (ii) a second discrete operative device;
  (iii) a stretchable interconnect coupling said first discrete operative device to said second discrete operative device, said stretchable interconnect having a substantially boustrophedonic pattern, wherein said stretchable interconnect maintains electrical communication between the first discrete operative device and the second discrete operative device when said stretchable interconnect is stretched up to about 1000%, and wherein said stretchable electronic circuit is disposed on the stretchable surface of said body.

15. The device of claim 14, wherein the first discrete operative device or the second discrete operative device includes a metal contact.

16. The device of claim 14, wherein the first discrete operative device or the second discrete operative device is a semiconductor device.

17. The device of claim 14, wherein the first discrete operative device, the second discrete operative device, and the stretchable interconnect are all made from a same material.

18. The device of claim 17, wherein the same material is a semiconductor material.

19. The device of claim 14, wherein the stretchable interconnect is made from a semiconductor material.

20. The device of claim 19, wherein the first discrete operative device is formed from a semiconductor material, and wherein the stretchable interconnect is made from the same semiconductor material as the first discrete operative device.

21. The device of claim 20, wherein the semiconductor material is a single crystal semiconductor material.

22. The device of claim 14, wherein the stretchable interconnect is formed from a different material than the first discrete operative device.

23. The device of claim 14, wherein the first discrete operative device and the second discrete operative device are in contact with the stretchable surface, and wherein the stretchable interconnect is not in contact with the stretchable surface.

24. The device of claim 23, wherein a portion of the stretchable surface has a wavy profile.

* * * * *